(12) United States Patent
Youngblood et al.

(10) Patent No.: US 12,208,216 B2
(45) Date of Patent: *Jan. 28, 2025

(54) SYSTEM FOR ENHANCING SLEEP RECOVERY AND PROMOTING WEIGHT LOSS

(71) Applicant: Sleep Solutions Inc., Wilmington, DE (US)

(72) Inventors: Tara Youngblood, Mooresville, NC (US); Todd Youngblood, Mooresville, NC (US)

(73) Assignee: Sleep Solutions Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,715

(22) Filed: Feb. 8, 2024

(65) Prior Publication Data

US 2024/0173516 A1 May 30, 2024

Related U.S. Application Data

(63) Continuation of application No. 18/119,651, filed on Mar. 9, 2023, now Pat. No. 11,896,774, which is a continuation of application No. 17/861,887, filed on Jul. 11, 2022, now Pat. No. 11,602,611, which is a continuation-in-part of application No. 16/715,652, filed on Dec. 16, 2019, now Pat. No. 11,812,859,
(Continued)

(51) Int. Cl.
*A61M 21/02* (2006.01)
*A61B 5/00* (2006.01)
*A61B 5/11* (2006.01)
*A61M 21/00* (2006.01)

(52) U.S. Cl.
CPC ........... *A61M 21/02* (2013.01); *A61B 5/1115* (2013.01); *A61B 5/4812* (2013.01); *A61B 5/748* (2013.01); *A61M 2021/0066* (2013.01)

(58) Field of Classification Search
CPC .......... A61M 21/02; A61M 2021/0066; A61B 5/1115; A61B 5/4812; A61B 5/748
See application file for complete search history.

(56) References Cited

U.S. PATENT DOCUMENTS

| 2,753,435 A | 7/1956 | Ivar |
| 3,230,556 A | 1/1966 | Wiusor |

(Continued)

FOREIGN PATENT DOCUMENTS

| KR | 20060019762 A | 3/2006 |
| KR | 20110102637 A | 9/2011 |
| WO | 2014145436 A1 | 9/2014 |

OTHER PUBLICATIONS

Buysse, D.J., Reynolds, C.F., Monk, T.H., Berman, S.R., & Kupfer, D.J. (1989). The Pittsburgh Sleep Quality Index (PSQI): A new instrument for psychiatric research and practice. Psychiatry Research, 28(2), 193-213.
(Continued)

*Primary Examiner* — Nael N Babaa
(74) *Attorney, Agent, or Firm* — POLSINELLI PC

(57) ABSTRACT

The present invention provides systems, methods, and articles for stress reduction and sleep promotion. A stress reduction and sleep promotion system includes at least one remote device, at least one body sensor, and at least one remote server. In other embodiments, the stress reduction and sleep promotion system includes machine learning.

20 Claims, 42 Drawing Sheets

Related U.S. Application Data which is a continuation-in-part of application No. 15/848,816, filed on Dec. 20, 2017, now Pat. No. 11,013,883, which is a continuation-in-part of application No. 15/705,829, filed on Sep. 15, 2017, now Pat. No. 10,986,933, which is a continuation-in-part of application No. 14/777,050, filed on Sep. 15, 2015, now Pat. No. 10,278,511.

(60) Provisional application No. 62/780,637, filed on Dec. 17, 2018, provisional application No. 62/398,257, filed on Sep. 22, 2016.

(56) References Cited

U.S. PATENT DOCUMENTS

| | | | |
|---|---|---|---|
| 4,132,262 A | 1/1979 | Wibell | |
| 4,459,468 A | 7/1984 | Bailey | |
| 4,777,802 A | 10/1988 | Feher | |
| 4,858,609 A | 8/1989 | Cole | |
| 5,033,136 A | 7/1991 | Elkins | |
| 5,304,112 A | 4/1994 | Mrklas et al. | |
| 5,329,096 A | 7/1994 | Suematsu | |
| 5,448,788 A | 9/1995 | Wu | |
| 5,894,615 A | 4/1999 | Alexander | |
| 5,948,303 A | 9/1999 | Larson | |
| 6,163,907 A | 12/2000 | Larson | |
| 6,273,810 B1 | 8/2001 | Rhodes, Jr. et al. | |
| 6,371,976 B1 | 4/2002 | Vrzalik et al. | |
| 6,463,743 B1 | 10/2002 | Laliberté | |
| 6,484,062 B1 | 11/2002 | Kim | |
| 6,581,224 B2 | 6/2003 | Yoon | |
| 6,826,792 B2 | 12/2004 | Lin | |
| 7,041,049 B1 | 5/2006 | Raniere | |
| 7,238,289 B2 | 7/2007 | Suddath | |
| 7,248,915 B2 | 7/2007 | Rönnholm | |
| 7,306,567 B2 | 12/2007 | Loree | |
| 7,382,047 B2 | 6/2008 | Chen et al. | |
| 7,460,899 B2 | 12/2008 | Almen | |
| 7,524,279 B2 | 4/2009 | Auphan | |
| 7,546,653 B2 | 6/2009 | Ye | |
| 7,608,041 B2 | 10/2009 | Sutton | |
| 7,699,785 B2 | 4/2010 | Nemoto | |
| 7,868,757 B2 | 1/2011 | Radivojevic et al. | |
| 7,908,687 B2 | 3/2011 | Ward et al. | |
| 8,096,960 B2 | 1/2012 | Loree et al. | |
| 8,179,270 B2 | 5/2012 | Rai et al. | |
| 8,191,187 B2 | 6/2012 | Brykalski et al. | |
| 8,290,596 B2 | 10/2012 | Wei et al. | |
| 8,348,840 B2 | 1/2013 | Heit et al. | |
| 8,418,285 B2 | 4/2013 | Frias | |
| 8,529,457 B2 | 9/2013 | Devot et al. | |
| 8,617,044 B2 | 12/2013 | Pelgrim et al. | |
| 8,768,520 B2 | 7/2014 | Oexman et al. | |
| 8,979,730 B2 | 3/2015 | Naujokat et al. | |
| 9,044,101 B2 | 6/2015 | Garcia et al. | |
| 9,186,479 B1 | 11/2015 | Franceschetti et al. | |
| 9,196,479 B1 | 11/2015 | Cheng et al. | |
| 9,402,763 B2 | 8/2016 | Bledsoe | |
| 9,459,597 B2 | 10/2016 | Kahn et al. | |
| 9,750,415 B2 | 9/2017 | Breslow et al. | |
| 9,981,107 B2 | 5/2018 | Franceschetti et al. | |
| 9,993,195 B2 | 6/2018 | Van Vugt et al. | |
| 9,999,744 B2 | 6/2018 | Proud | |
| 10,154,932 B2 | 12/2018 | Franceschetti et al. | |
| 10,179,064 B2 | 1/2019 | Connor | |
| 10,188,222 B2 | 1/2019 | Veron | |
| 10,216,485 B2 | 2/2019 | Misra et al. | |
| 10,350,108 B1 | 7/2019 | Rittman, III et al. | |
| 10,391,009 B2 | 8/2019 | Bhai | |
| 10,398,357 B2 | 9/2019 | Chen et al. | |
| 10,401,807 B2 | 9/2019 | Jo et al. | |
| 10,675,434 B2 | 6/2020 | Van Driel et al. | |
| 10,686,626 B2 | 6/2020 | Sarwar et al. | |
| 10,709,335 B2 | 7/2020 | Matsuoka et al. | |
| 10,764,079 B2 | 9/2020 | Mahar et al. | |
| 10,764,374 B1 | 9/2020 | Marquardt et al. | |
| 10,824,634 B2 | 11/2020 | Siebel et al. | |
| 10,833,888 B2 | 11/2020 | Kim et al. | |
| 10,923,226 B2 | 2/2021 | Macary et al. | |
| 10,959,667 B2 | 3/2021 | Xin et al. | |
| 10,971,261 B2 | 4/2021 | Kahn et al. | |
| 11,040,169 B2 | 6/2021 | Jung et al. | |
| 11,097,079 B2 | 8/2021 | Shanmugam et al. | |
| 11,134,888 B2 | 10/2021 | Wright et al. | |
| 11,185,281 B2 | 11/2021 | Molina et al. | |
| 2002/0014951 A1 | 2/2002 | Kramer et al. | |
| 2002/0080035 A1 | 6/2002 | Youdenko | |
| 2002/0124574 A1 | 9/2002 | Guttman et al. | |
| 2004/0049132 A1 | 3/2004 | Barron et al. | |
| 2005/0143617 A1 | 6/2005 | Auphan | |
| 2005/0154330 A1 | 7/2005 | Loree | |
| 2006/0137099 A1 | 6/2006 | Feher | |
| 2006/0293602 A1 | 12/2006 | Clark | |
| 2006/0293608 A1 | 12/2006 | Rothman et al. | |
| 2007/0234741 A1 | 10/2007 | Lee et al. | |
| 2008/0016881 A1 | 1/2008 | Steffensen et al. | |
| 2008/0234785 A1 | 9/2008 | Nakayama et al. | |
| 2009/0112069 A1 | 4/2009 | Kanamori et al. | |
| 2009/0121826 A1 | 5/2009 | Song et al. | |
| 2009/0288800 A1 | 11/2009 | Kang et al. | |
| 2010/0011502 A1 | 1/2010 | Brykalski et al. | |
| 2010/0100004 A1 | 4/2010 | van Someren | |
| 2010/0174198 A1 | 7/2010 | Young et al. | |
| 2010/0197996 A1 | 8/2010 | Cornel | |
| 2010/0199687 A1 | 8/2010 | Woods et al. | |
| 2010/0293715 A1 | 11/2010 | Sakamoto et al. | |
| 2010/0324611 A1 | 12/2010 | Deming et al. | |
| 2011/0015327 A1 | 1/2011 | Bichler et al. | |
| 2011/0015495 A1 | 1/2011 | Dothie et al. | |
| 2011/0073292 A1 | 3/2011 | Datta et al. | |
| 2011/0107514 A1 | 5/2011 | Brykalski et al. | |
| 2011/0153274 A1 | 6/2011 | Ho et al. | |
| 2011/0181597 A1 | 7/2011 | Cardno et al. | |
| 2011/0230790 A1 | 9/2011 | Kozlov | |
| 2011/0247139 A1 | 10/2011 | Tallent et al. | |
| 2011/0252461 A1 | 10/2011 | Wetzer et al. | |
| 2011/0267196 A1 | 11/2011 | Hu et al. | |
| 2012/0054754 A1 | 3/2012 | Teichmann et al. | |
| 2012/0136666 A1 | 5/2012 | Corpier et al. | |
| 2012/0159968 A1 | 6/2012 | Doucet et al. | |
| 2012/0296402 A1 | 11/2012 | Kotter | |
| 2013/0019611 A1 | 1/2013 | Sims et al. | |
| 2013/0060306 A1 | 3/2013 | Colbauch | |
| 2013/0208576 A1 | 8/2013 | Loree, IV et al. | |
| 2013/0234823 A1 | 9/2013 | Kahn et al. | |
| 2013/0304768 A1 | 11/2013 | Basnight et al. | |
| 2014/0006001 A1 | 1/2014 | Kamhi et al. | |
| 2014/0208508 A1 | 7/2014 | Mikesell | |
| 2014/0277308 A1 | 9/2014 | Cronise et al. | |
| 2014/0316495 A1 | 10/2014 | Augustine et al. | |
| 2015/0093101 A1 | 4/2015 | Lee | |
| 2015/0203068 A1 | 7/2015 | Foo et al. | |
| 2015/0257697 A1 | 9/2015 | Sepah | |
| 2015/0289666 A1 | 10/2015 | Chandler et al. | |
| 2015/0351982 A1 | 12/2015 | Krenik | |
| 2015/0366703 A1 | 12/2015 | Du | |
| 2016/0015184 A1 | 1/2016 | Nunn et al. | |
| 2016/0015315 A1 | 1/2016 | Auphan et al. | |
| 2016/0029808 A1 | 2/2016 | Youngblood et al. | |
| 2016/0136385 A1 | 5/2016 | Scorcioni | |
| 2016/0151603 A1 | 6/2016 | Shouldice et al. | |
| 2016/0235610 A1 | 8/2016 | Drake | |
| 2016/0239624 A1 | 8/2016 | Short et al. | |
| 2016/0249842 A1 | 9/2016 | Lubelchick | |
| 2016/0310697 A1 | 10/2016 | Franceschetti et al. | |
| 2017/0003666 A1 | 1/2017 | Nunn et al. | |
| 2017/0017759 A1 | 1/2017 | MacNeice et al. | |
| 2017/0053068 A1 | 2/2017 | Pillai et al. | |
| 2017/0095196 A1 | 4/2017 | Oakhill | |
| 2017/0138663 A1 | 5/2017 | Wells | |
| 2017/0189641 A1 | 7/2017 | Moturu et al. | |
| 2017/0231812 A1 | 8/2017 | Boyden et al. | |
| 2018/0000255 A1 | 1/2018 | Youngblood et al. | |

(56) References Cited

U.S. PATENT DOCUMENTS

| | | |
|---|---|---|
| 2018/0082550 A1 | 3/2018 | Read et al. |
| 2018/0110960 A1 | 4/2018 | Youngblood et al. |
| 2018/0203744 A1 | 7/2018 | Wiesmaier et al. |
| 2018/0226155 A1 | 8/2018 | Mahoney et al. |
| 2018/0260387 A1 | 9/2018 | Ben-Kiki et al. |
| 2018/0285528 A1 | 10/2018 | Healey et al. |
| 2018/0325450 A1 | 11/2018 | Huang |
| 2018/0344517 A1 | 12/2018 | Nofzinger |
| 2019/0099009 A1 | 4/2019 | Connor |
| 2019/0203983 A1 | 7/2019 | Jeon et al. |
| 2019/0209405 A1 | 7/2019 | Sayadi et al. |
| 2019/0231081 A1 | 8/2019 | Youngblood et al. |
| 2019/0265971 A1 | 8/2019 | Behzadi et al. |
| 2019/0349254 A1 | 11/2019 | Nolan et al. |
| 2020/0027552 A1 | 1/2020 | Lee |
| 2020/0046134 A1 | 2/2020 | Youngblood et al. |
| 2020/0077942 A1 | 3/2020 | Youngblood et al. |
| 2020/0100682 A1 | 4/2020 | Abreu et al. |
| 2020/0113344 A1 | 4/2020 | Youngblood et al. |
| 2020/0171268 A1 | 6/2020 | Zhang |
| 2020/0178887 A1 | 6/2020 | Ramírez et al. |
| 2020/0205727 A1 | 7/2020 | Shen et al. |
| 2020/0215295 A1 | 7/2020 | LaPorte et al. |
| 2020/0229967 A1 | 7/2020 | Drew |
| 2020/0236907 A1 | 7/2020 | Nilsson et al. |
| 2020/0281521 A1 | 9/2020 | Cail |
| 2020/0289052 A1 | 9/2020 | Gross |
| 2020/0315368 A1 | 10/2020 | Tsern et al. |
| 2020/0337470 A1 | 10/2020 | Sayadi et al. |
| 2020/0397379 A1 | 12/2020 | Franceschetti et al. |
| 2021/0031000 A1 | 2/2021 | Lee et al. |
| 2021/0146091 A1 | 5/2021 | Kansagra |
| 2021/0178113 A1 | 6/2021 | Bresch et al. |
| 2021/0267379 A1 | 9/2021 | Youngblood et al. |
| 2021/0267380 A1 | 9/2021 | Stusynski |
| 2021/0314405 A1 | 10/2021 | Demirli et al. |
| 2022/0134050 A1 | 5/2022 | Moriyasu |
| 2022/0176065 A1 | 6/2022 | Youngblood et al. |
| 2022/0339398 A1 | 10/2022 | Youngblood et al. |
| 2023/0248934 A1 | 8/2023 | Youngblood et al. |

OTHER PUBLICATIONS

Quan, S. F. et al; "Healthy Sleep The Characteristics of Sleep" (Sep. 21, 2016) pp. 1-4, retrieved from http://healthysleep.med.harvard.edu/healthy/science/what/characteristics.

Tobaldini, E. et al; "Heart rate variability in normal and pathological sleep", Frontiers in Physiology, (Oct. 16, 2013), p. 1-11, vol. 4, Article 294, doi: 10.3389/fphys.2013.00294.

U.S. Appl. No. 61/800,768 Youngblood, Thermo electric heating and cooling device, filed Mar. 15, 2013, Drawings and Specification.

U.S. Appl. No. 62/398,257, Youngblood, Bed Pad With Custom Modulated Temperature Adjustment, filed Sep. 22, 2016, Drawings and Specification.

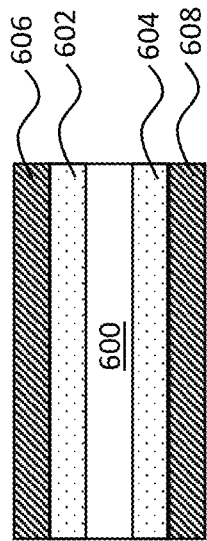
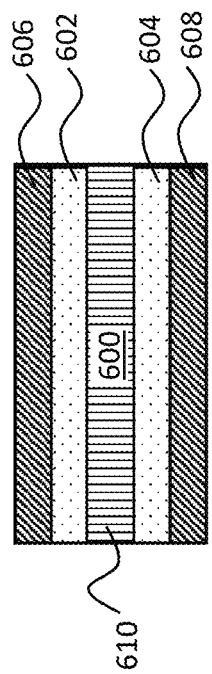
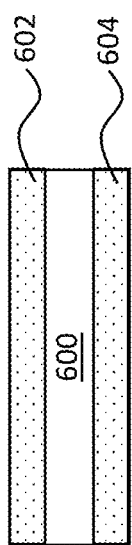
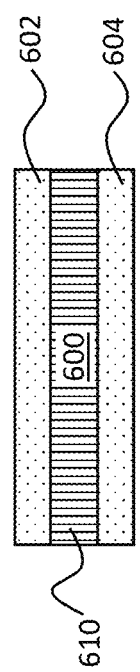
FIG. 9A
FIG. 9B
FIG. 9C
FIG. 9D

| Age | Average Deep Sleep Percentage |
|---|---|
| 20-29 | 20% |
| 30-39 | 15% |
| 40-49 | 12% |
| 50-59 | 10% |
| 60-69 | 8% |
| 70-89 | <5% |

FIG. 29

| Target Deep Sleep Percentage | | | | | |
|---|---|---|---|---|---|
| Age | Athletes | Excellent | Good | Average | Poor |
| 18-25 | 22-25 | 24-26 | 19-22 | 19-21 | ≤18 |
| 26-35 | 20-22 | 22-24 | 18-21 | 17-19 | ≤16 |
| 36-45 | 18-21 | 19-23 | 17-19 | 14-18 | ≤13 |
| 46-55 | 17-21 | 18-23 | 15-17 | 12-16 | ≤11 |
| 56-65 | 17-21 | 18-23 | 14-16 | 10-14 | ≤9 |
| 65+ | 17-21 | 17-23 | 12-15 | 8-12 | ≤7 |

FIG. 30

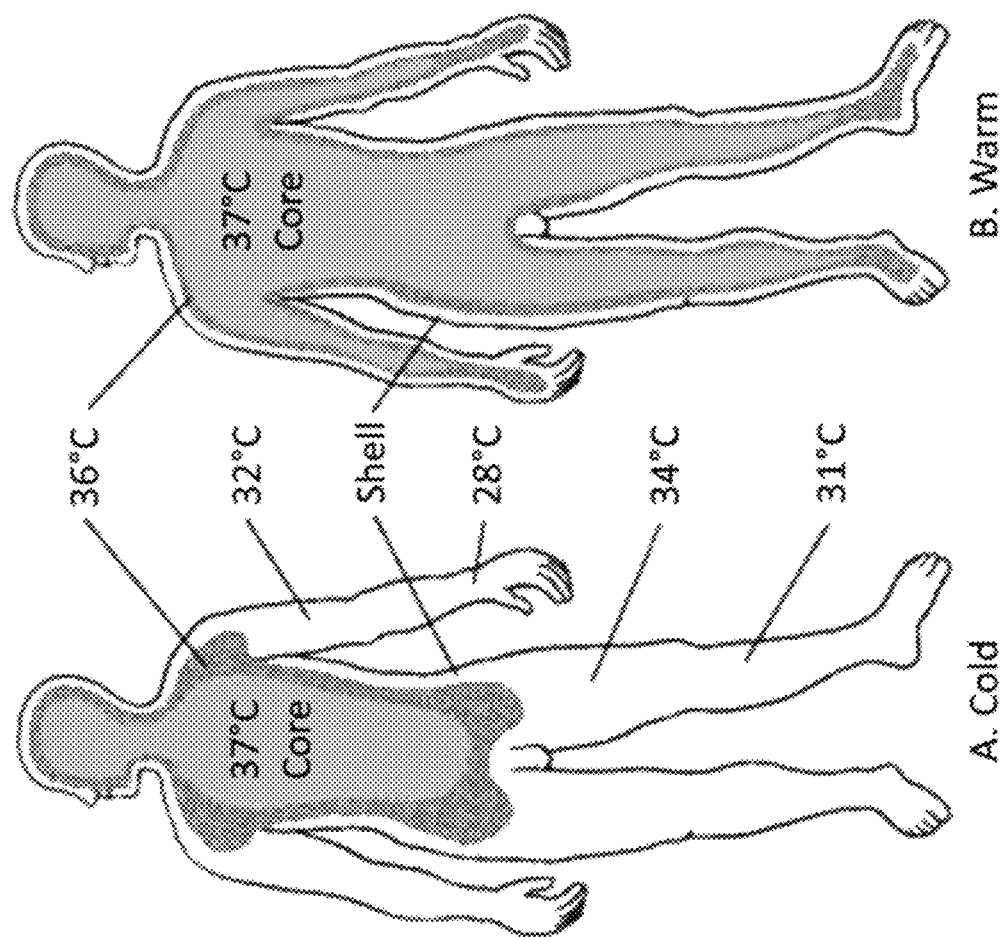
PRIOR ART FIG. 31

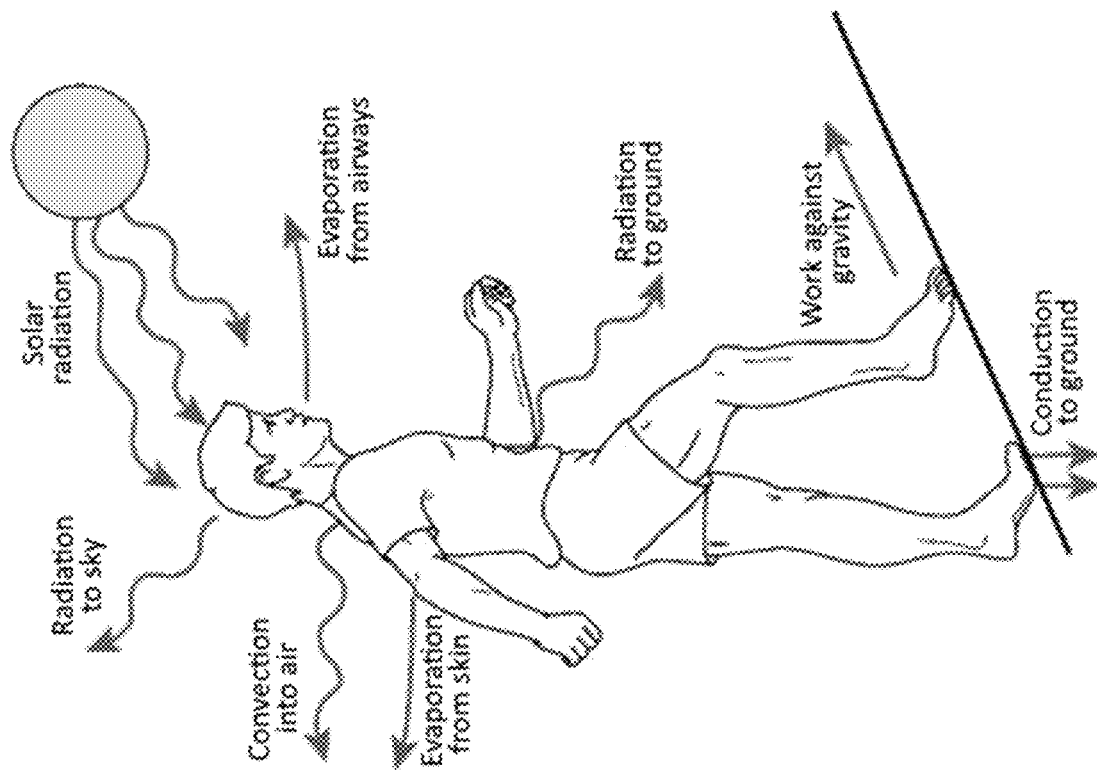
PRIOR ART FIG. 32

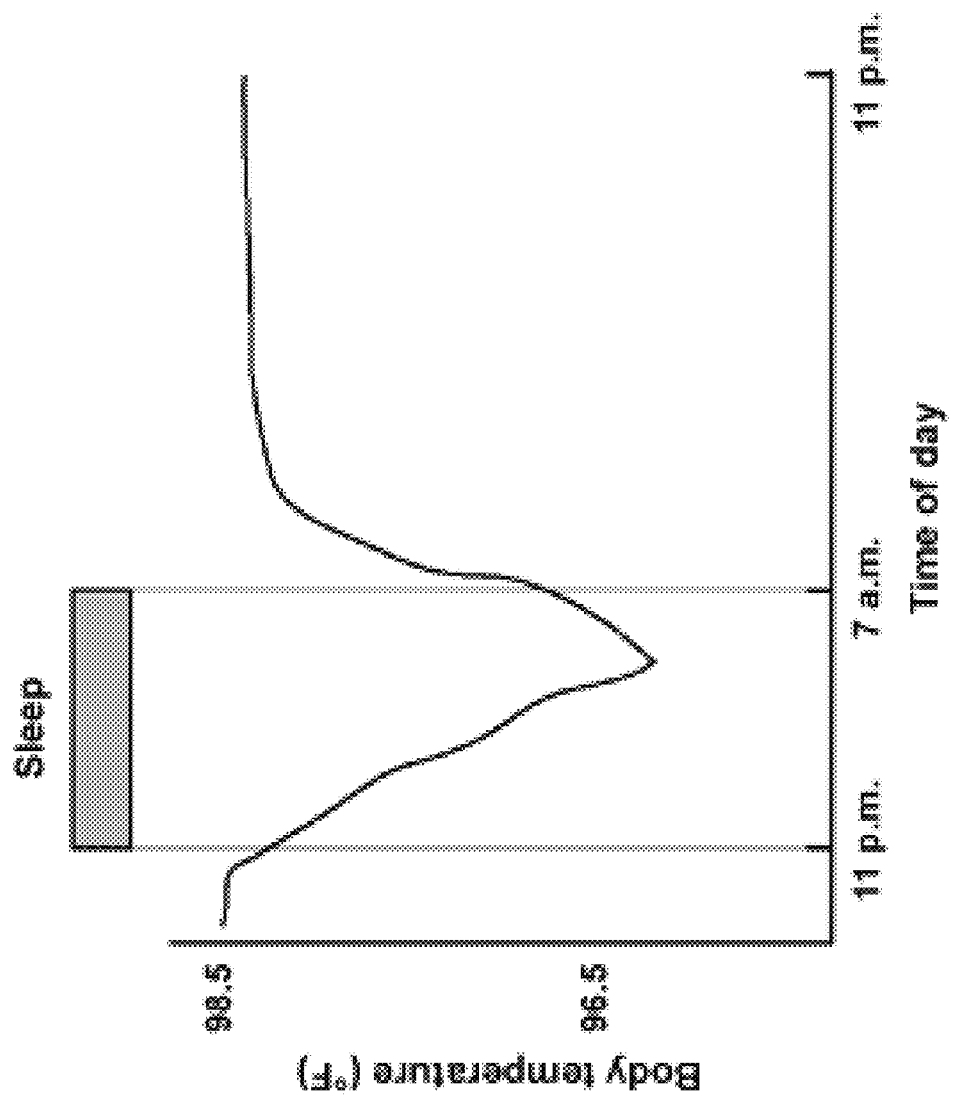
PRIOR ART FIG. 33

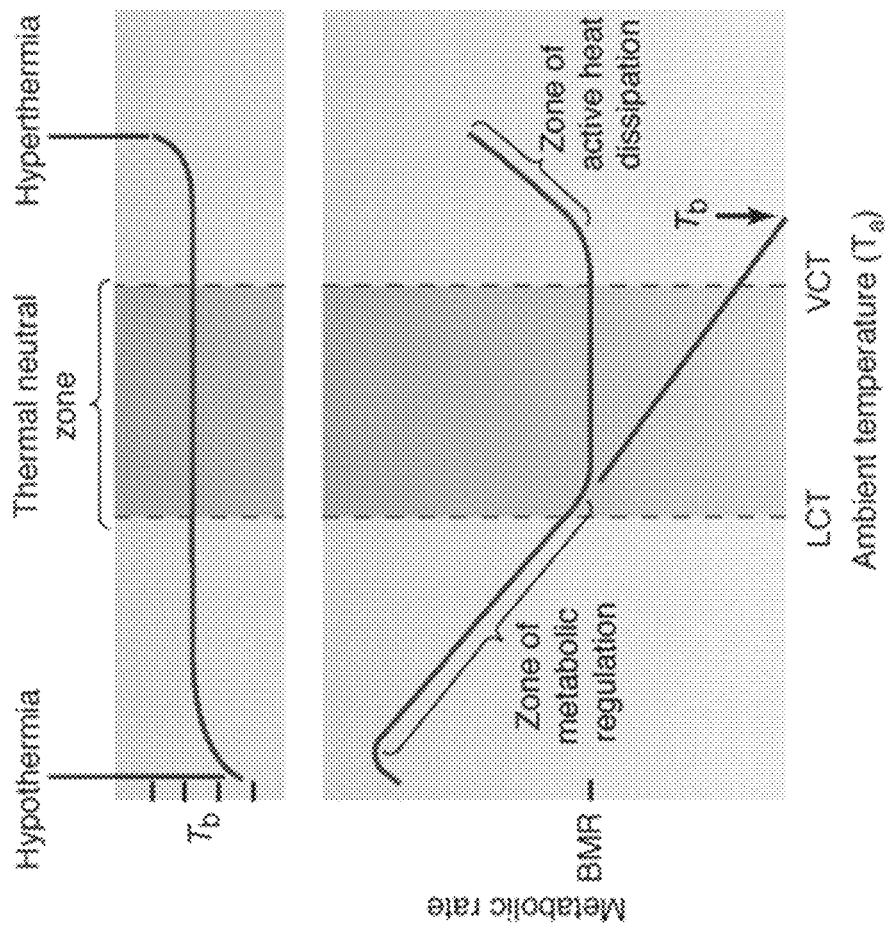
PRIOR ART FIG. 34

Resting Heart Rate Chart for Men

| Age | Athletes | Excellent | Good | Above Ave. | Ave. | Below Ave. | Poor |
|---|---|---|---|---|---|---|---|
| 18-25 | 49-55 | 56-61 | 62-65 | 66-69 | 70-73 | 74-81 | 82+ |
| 26-35 | 49-54 | 55-61 | 62-65 | 66-70 | 71-74 | 75-81 | 82+ |
| 36-45 | 50-56 | 57-62 | 63-66 | 67-70 | 71-75 | 76-82 | 83+ |
| 46-55 | 50-57 | 58-63 | 64-67 | 68-71 | 72-76 | 77-83 | 84+ |
| 56-65 | 51-56 | 57-61 | 62-67 | 68-71 | 72-75 | 76-81 | 82+ |
| 65+ | 50-55 | 56-61 | 62-65 | 66-69 | 70-73 | 74-79 | 80+ |

Resting Heart Rate Chart for Women

| Age | Athletes | Excellent | Good | Above Ave. | Ave. | Below Ave. | Poor |
|---|---|---|---|---|---|---|---|
| 18-25 | 54-60 | 61-65 | 66-69 | 70-73 | 74-78 | 79-84 | 85+ |
| 26-35 | 54-59 | 60-64 | 65-68 | 69-72 | 73-76 | 77-82 | 83+ |
| 36-45 | 54-59 | 60-64 | 65-69 | 70-73 | 74-78 | 79-84 | 85+ |
| 46-55 | 54-60 | 61-65 | 66-69 | 70-73 | 74-77 | 78-83 | 84+ |
| 56-65 | 54-59 | 60-64 | 65-68 | 69-73 | 74-77 | 78-83 | 84+ |
| 65+ | 54-59 | 60-64 | 65-68 | 69-72 | 73-76 | 77-84 | 84+ |

PRIOR ART FIG. 35

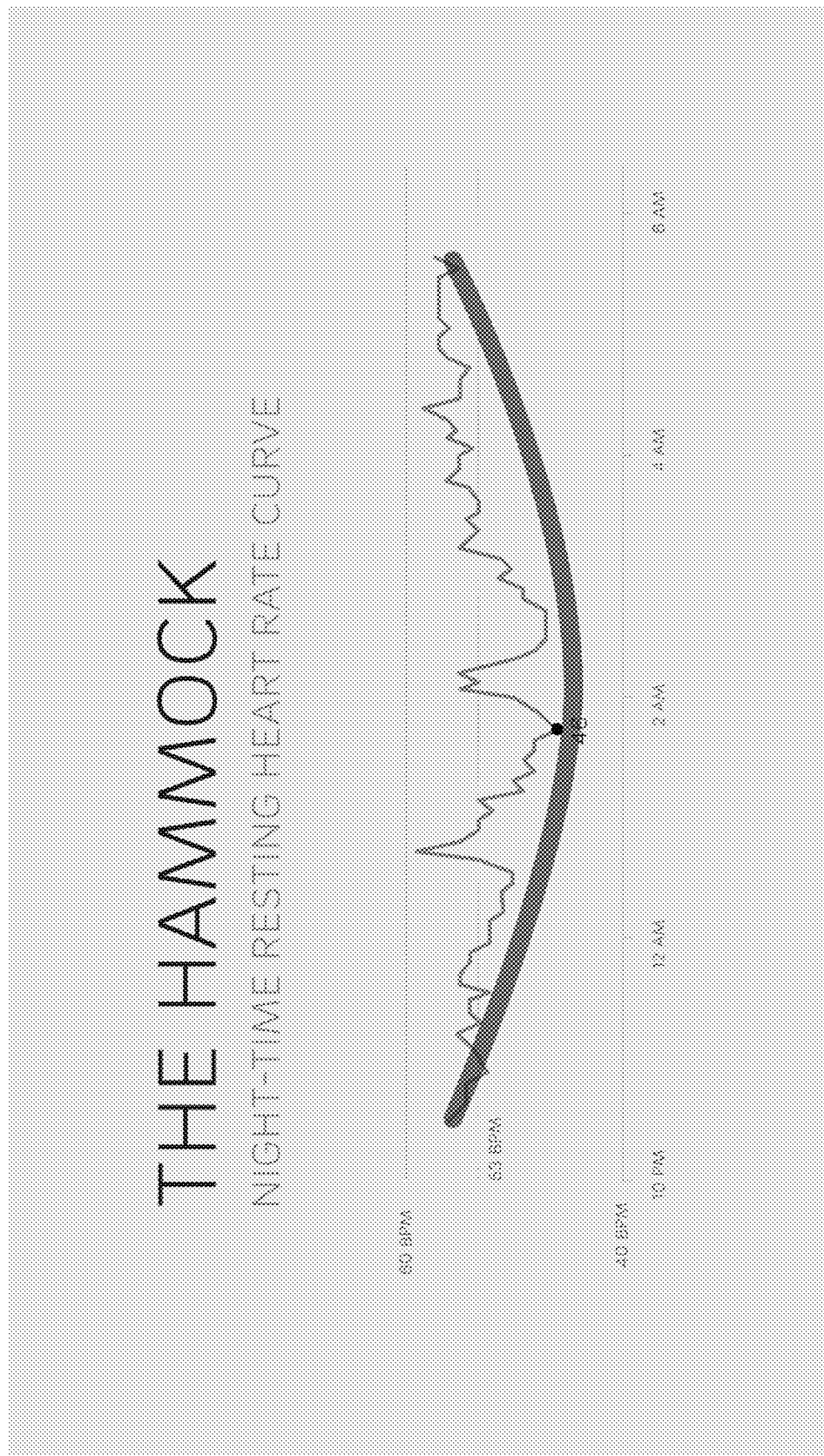
PRIOR ART FIG. 36

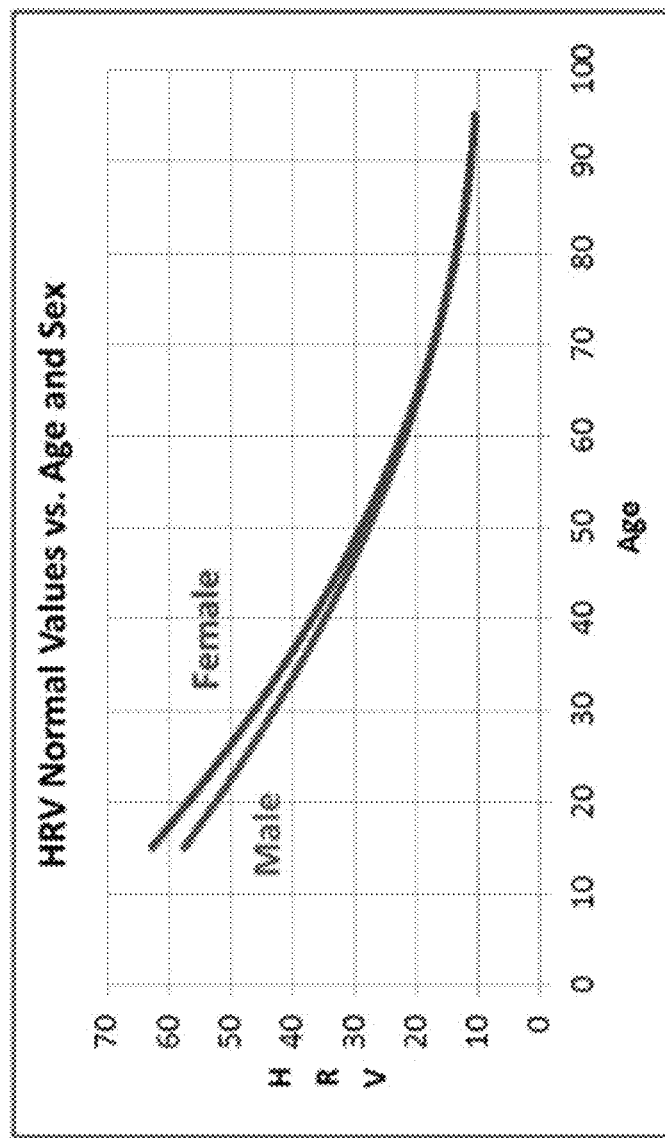
PRIOR ART FIG. 37

SYSTEM FOR ENHANCING SLEEP RECOVERY AND PROMOTING WEIGHT LOSS

CROSS REFERENCE TO RELATED APPLICATIONS

This application relates to and claims priority from the following applications. This application is a continuation of U.S. patent application Ser. No. 18/119,651, filed Mar. 9, 2023, which is a continuation of U.S. patent application Ser. No. 17/861,887, filed Jul. 11, 2022 and issued as U.S. Pat. No. 11,602,611, which is a continuation-in-part of U.S. patent application Ser. No. 16/715,652, filed Dec. 16, 2019 and issued as U.S. Pat. No. 11,812,859, which claims the benefit of U.S. Provisional Patent Application No. 62/780,637, filed Dec. 17, 2018. U.S. patent application Ser. No. 16/715,652 is also a continuation-in-part of U.S. patent application Ser. No. 15/848,816, filed Dec. 20, 2017 and issued as U.S. Pat. No. 11,013,883, which is a continuation-in-part of U.S. application Ser. No. 15/705,829, filed Sep. 15, 2017 and issued as U.S. Pat. No. 10,986,933, which is a continuation-in-part of U.S. application Ser. No. 14/777,050, filed Sep. 15, 2015 and issued as U.S. Pat. No. 10,278,511, which is the National Stage of International Application No. PCT/US2014/030202, filed Mar. 17, 2014, which claims the benefit of U.S. Provisional Application No. 61/800,768, filed Mar. 15, 2013. U.S. application Ser. No. 15/705,829 also claims the benefit of U.S. Provisional Application No. 62/398,257, filed Sep. 22, 2016. Each of the above applications is incorporated herein by reference in its entirety.

BACKGROUND OF THE INVENTION

1. Field of the Invention

This invention relates broadly and generally to articles, methods, and systems for non-shivering thermogenesis to enhance sleep recovery and/or promote weight loss.

2. Description of the Prior Art

Humans are homeothermic and require a nearly constant core body temperature (e.g., 36.5-37.5° C. (97.7-99.5° F.) to maintain normal physiological functions. The core body temperature remains constant even while the environmental temperature fluctuates.

Humans have two methods of regulating core body temperature: behavioral thermoregulation and physiological thermoregulation. Behavioral thermoregulation includes the use of shelter, devices (e.g., heating, air conditioning), and adjusting clothing layers to be comfortable in the environment. Physiological thermoregulation is the body using excess heat produced as waste from metabolic processes to maintain the core body temperature. However, physiological thermoregulation only is effective within a specific environmental temperature range.

The body uses physiological thermoregulation to increase metabolic output (e.g., heat) to match heat lost to the environment as a means of maintaining core body temperature. One method of physiological thermoregulation is non-shivering thermogenesis. Non-shivering thermogenesis results in an increase in metabolic heat without shivering, which can damage muscles and cause exhaustion. Advantageously, this increase in metabolic heat leads to an increased caloric burn, which leads to weight loss when combined with diet and/or exercise. Thus, cold therapy including non-shivering thermogenesis can be used for weight loss.

Further, cold therapy is able to be used to treat insomnia. The core body temperature naturally decreases by 0.56-1.1° C. (1-2° F.) as a person falls asleep. If the core body temperature does not drop or does not remain low, a person will have difficulty falling asleep or staying asleep, respectively.

Various methods and systems for cold therapy to treat insomnia and/or promote weight loss are known. These systems often include a physical device to cool the body.

Prior art patent documents include the following:

U.S. Pat. No. 7,041,049 for sleep guidance system and related methods by inventor Raniere, filed Nov. 21, 2003 and issued May 9, 2006, discloses a sleep efficiency monitor and methods for pacing and leading a sleeper through an optimal sleep pattern. Embodiments of the invention include a physiological characteristic monitor for monitoring the sleep stages of a sleeper, a sensory stimulus generator for generating stimulus to affect the sleep stages of a sleeper, and a processor for determining what sleep stage the sleeper is in and what sensory stimulus is needed to cause the sleeper to move to another sleep stage. A personalized sleep profile may also be established for the sleeper and sleep guided in accordance with the profile parameters to optimize a sleep session. By providing sensory stimulus to a sleeper, the sleeper may be guided through the various sleep stages in an optimal pattern so that the sleeper awakens refreshed even if sleep is disrupted during the night or the sleeper's allotted sleep period is different than usual. Embodiments of the invention also involve calibration of the sleep guidance system to a particular sleeper.

U.S. Patent Publication No. 2006/0293602 for sleep management device by inventor Clark, filed Apr. 8, 2004 and published Dec. 28, 2006, discloses a short sleep/nap management apparatus and method. The apparatus has sensor means to detect one or more physiological parameters associated with a transition in sleep stages from wakefulness, processing means to process the parameters to determine when the transition is reached and start the timer to run for a predetermined period, and alarm means to actuate at the end of said predetermined period to awaken the user.

U.S. Patent Publication No. 2006/0293608 for device for and method of predicting a user's sleep state by inventors Rothman et al., filed Feb. 28, 2005 and published Dec. 28, 2006, discloses a device and a method for waking a user in a desired sleep state. The device may predict an occurrence when the user will be in the desired sleep state, such as light sleep, and wake the user during that predicted occurrence. In one embodiment, a user may set a wake-up time representing the latest possible time that the user would like to be awakened. The occurrence closest to the wake-up time when the user will be in light sleep may be predicted, thereby allowing the user to sleep as long as possible, while awakening in light sleep. To predict when the user will be in the desired sleep state, the user's sleep state may be monitored during the night or sleep experience and the monitored information may be used in predicting when the user will be in the desired sleep state.

U.S. Patent Publication No. 2008/0234785 for sleep controlling apparatus and method, and computer program product thereof by inventors Nakayama et al., filed Sep. 13, 2007 and published Sep. 25, 2008, discloses a sleep controlling apparatus that includes a measuring unit that measures biological information of a subject; a first detecting unit that detects a sleeping state of the subject selected from the group consisting of a falling asleep state, a REM sleep state, a light non-REM sleep state and a deep non-REM sleep state, based on the biological information measured by the measuring unit; a first stimulating unit that applies a first stimulus of an intensity lower than a predetermined threshold value to the subject when the light non-REM sleep state is detected by the first detecting unit; and a second stimulating unit that applies a second stimulus of an intensity higher than the first stimulus after the first stimulus is applied to the subject.

U.S. Pat. No. 7,460,899 for apparatus and method for monitoring heart rate variability by inventor Almen, filed Feb. 25, 2005 and issued Dec. 2, 2008, discloses a wrist-worn or arm band worn heart rate variability monitor. Heart rate variability ("HRV") refers to the variability of the time interval between heartbeats and is a reflection of an individual's current health status. Over time, an individual may use the results of HRV tests to monitor either improvement or deterioration of specific health issues. Thus, one use of the HRV test is as a medical motivator. When an individual has a poor HRV result, it is an indicator that they should consult their physician and make appropriate changes where applicable to improve their health. If an individual's HRV results deviate significantly from their normal HRV, they may be motivated to consult their physician. In addition, the inventive monitor is capable of monitoring the stages of sleep by changes in the heart rate variability and can record the sleep (or rest) sessions with the resulting data accessible by the user or other interested parties. Alternate embodiments of the invention allow assistance in the diagnosis and monitoring of various cardiovascular and sleep breathing disorders and/or conditions. Other embodiments allow communication with internal devices such as defibrillators or drug delivery mechanisms. Still other embodiments analyze HRV data to assist the user in avoiding sleep.

U.S. Pat. No. 7,524,279 for sleep and environment control method and system by inventor Auphan, filed Dec. 29, 2004 and issued Apr. 28, 2009, discloses a sleep system that includes sensors capable of gathering sleep data from a person and environmental data during a sleep by the person. A processor executes instructions that analyze this data and control the sleep of the person and the environment surrounding the person. Typically, the instructions are loaded in a memory where they execute to generate an objective measure of sleep quality from the sleep data from the person and gather environmental data during the sleep by the person. Upon execution, the instructions receive a subjective measure of sleep quality from the person after the sleep, create a sleep quality index from the objective measure of sleep quality and subjective measure of sleep quality, correlate the sleep quality index and a current sleep system settings with a historical sleep quality index and corresponding historical sleep system settings. The instructions then may modify the current set of sleep system settings depending on the correlation between the sleep quality index and the historic sleep quality index. These sleep system settings control and potentially change one or more different elements of an environment associated with the sleep system.

U.S. Patent Publication No. 2009/0112069 for trend prediction device by inventors Kanamori et al., filed Sep. 25, 2008 and published Apr. 30, 2009, discloses a trend prediction device that is versatile and capable of improving the accuracy of predicting a trend in a user's physical condition. The trend prediction device includes: a sensor-data converter configured to convert sensor data detected by a sleep sensor into a sleep-related parameter for making a physical-data-trend judgment; a parameter acquisition unit configured to acquire a lifestyle-related parameter that indicates an action of the user during a non-sleeping period, and possibly changing the physical-data trend; and a parameter comparator configured to compare the sleep-related and the lifestyle-related parameters with respective reference parameters. The trend prediction device is configured to judge whether the physical data has an increase or a decrease in trend on the basis of the comparison result of the sleep-related and the lifestyle-related parameters with their respective reference parameters.

U.S. Pat. No. 7,608,041 for monitoring and control of sleep cycles by inventor Sutton, filed Apr. 20, 2007 and issued Oct. 27, 2009, discloses a system including: a monitor for monitoring a user's sleep cycles; a processor which counts the sleep cycles to provide a sleep cycle count and which selects an awakening time according to a decision algorithm including the sleep cycle count as an input; and an alarm for awakening the user at the awakening time. Use of the sleep cycle count as an input to the decision algorithm advantageously enables a user to more fully control and optimize his or her personal sleeping behavior.

U.S. Pat. No. 7,699,785 for method for determining sleep stages by inventor Nemoto, filed Feb. 23, 2005 and issued Apr. 20, 2010, discloses a method for determining sleep stages of an examinee, including detecting signals of the examinee with a biosignal detector, calculating a signal strength deviation value that indicates deviation of a signal strength of the detected signals, and determining a sleep stage by using the signal strength deviation value or a value of a plurality of values based on the signal strength deviation value as an indicator value.

U.S. Patent Publication No. 2010/0100004 for skin temperature measurement in monitoring and control of sleep and alertness by inventor van Someren, filed Dec. 15, 2008 and published Apr. 22, 2010, discloses a method of an arrangement for monitoring sleep in a subject by measuring within a prescribed interval skin temperature of a predetermined region of the subject's body and a motion sensor for sensing motion of the subject, comparing the measured skin temperature of the predetermined region with a predetermined temperature threshold, and classifying the subject as being asleep or awake based on whether the skin temperature of the predetermined region is above or below the temperature threshold and on the motion data. In alternative aspects the invention relates to methods of and arrangements for manipulating sleep, as well as monitoring or manipulating alertness.

U.S. Pat. No. 7,868,757 for method for the monitoring of sleep using an electronic device by inventors Radivojevic et al., filed Dec. 29, 2006 and issued Jan. 11, 2011, discloses a method where sleep sensor signals are obtained to a mobile communication device from sensor devices. The mobile communication device checks the sleep sensor signals for a sleep state transition, determines the type of the sleep state transition, forms control signals based on the type of the sleep state transition and sends the control signals to at least one electronic device.

U.S. Patent Publication No. 2011/0015495 for method and system for managing a user's sleep by inventors Dothie et al., filed Jul. 16, 2010 and published Jan. 20, 2011, discloses a sleep management method and system for improving the quality of sleep of a user which monitors one or more objective parameters relevant to sleep quality of the user when in bed and receives from the user in waking hours via a portable device such as a mobile phone feedback from objective test data on cognitive and/or psychomotor performance.

U.S. Patent Publication No. 2011/0230790 for method and system for sleep monitoring, regulation and planning by inventor Kozlov, filed Mar. 27, 2010 and published Sep. 22, 2011, discloses a method for operating a sleep phase actigraphy synchronized alarm clock that communicates with a remote sleep database, such as an internet server database, and compares user physiological parameters, sleep settings, and actigraphy data with a large database that may include data collected from a large number of other users with similar physiological parameters, sleep settings, and actigraphy data. The remote server may use "black box" analysis approach by running supervised learning algorithms to analyze the database, producing sleep phase correction data which can be uploaded to the alarm clock, and be used by the alarm clock to further improve its REM sleep phase prediction accuracy.

U.S. Patent Publication No. 2011/0267196 for system and method for providing sleep quality feedback by inventors Hu et al., filed May 3, 2011 and published Nov. 3, 2011, discloses a system and method for providing sleep quality feedback that includes receiving alarm input on a base device from a user; the base device communicating an alarm setting based on the alarm input to an individual sleep device; the individual sleep device collecting sleep data based on activity input of a user; the individual sleep device communicating sleep data to the base device; the base device calculating sleep quality feedback from the sleep data; communicating sleep quality feedback to a user; and the individual sleep device activating an alarm, wherein activating the alarm includes generating tactile feedback to the user according to the alarm setting.

U.S. Pat. No. 8,179,270 for methods and systems for providing sleep conditions by inventors Rai et al., filed Jul. 21, 2009 and issued May 15, 2012, discloses a method for monitoring a sleep condition with a sleep scheduler wherein the method includes receiving a sleep parameter via an input receiver on the sleep scheduler. The method further includes associating the sleep parameter with an overall alertness and outputting a determined sleep condition based on the overall alertness. A system for providing a sleep condition is further disclosed therein the system comprising includes a display, an input receiver operable to receive a sleep parameter, and a processor in communication with the display. The processor may be operable to determine an overall alertness associated with the sleep parameter and wherein the processor is operable to output a determined sleep condition based on the overall alertness.

U.S. Pat. No. 8,290,596 for therapy program selection based on patient state by inventors Wei et al., filed Sep. 25, 2008 and issued Oct. 16, 2012, discloses selecting a therapy program based on a patient state, where the patient state comprises at least one of a movement state, sleep state or speech state. In this way, therapy delivery is tailored to the patient state, which may include specific patient symptoms. The therapy program is selected from a plurality of stored therapy programs that comprise therapy programs associated with a respective one at least two of the movement, sleep, and speech states. Techniques for determining a patient state include receiving volitional patient input or detecting biosignals generated within the patient's brain. The biosignals are nonsymptomatic and may be incidental to the movement, sleep, and speech states or generated in response to volitional patient input.

U.S. Publication No. 20120296402 for device and method for brown adipose tissue activation by inventor Kotter, filed May 17, 2011 and published Nov. 22, 2012, discloses devices and methods of activating brown adipose tissue. One method comprises applying a cooling device on a subject at a supraclavicular region or paravertebral region of skin overlying brown adipose tissue; and maintaining the cooling device in contact with the skin at a temperature from 45° F. to 70° F. for a duration of at least 90 minutes so as to cool the region sufficiently to activate the brown adipose tissue.

U.S. Pat. No. 8,348,840 for device and method to monitor, assess and improve quality of sleep by inventors Heit et al., filed Feb. 4, 2010 and issued Jan. 8, 2013, discloses a medical sleep disorder arrangement that integrates into current diagnosis and treatment procedures to enable a health care professional to diagnose and treat a plurality of subjects suffering from insomnia. The arrangement may include both environmental sensors and body-worn sensors that measure the environmental conditions and the condition of the individual patient. The data may be collected and processed to measure clinically relevant attributes of sleep quality automatically. These automatically determined measures, along with the original sensor data, may be aggregated and shared remotely with the health care professional. A communication apparatus enables the healthcare professional to remotely communicate with and further assess the patient and subsequently administer the treatment. Thus, a more accurate diagnosis and more effective treatment is provided while reducing the required clinician time per patient for treatment delivery.

U.S. Pat. No. 8,529,457 for system and kit for stress and relaxation management by inventors Devot et al., filed Aug. 20, 2010 and issued Sep. 10, 2013, discloses a system and a kit for stress and relaxation management. A cardiac activity sensor is used for measuring the heart rate variability (HRV) signal of the user and a respiration sensor for measuring the respiratory signal of the user. The system contains a user interaction device having an input unit for receiving user specific data and an output unit for providing information output to the user. A processor is used to assess the stress level of the user by determining a user related stress index. The processor is also used to monitor the user during a relaxation exercise by means of determining a relaxation index based on the measured HRV and respiratory signals, the relaxation index being continuously adapted to the incoming measured signals and based thereon the processor instructs the output unit to provide the user with biofeedback and support messages. Finally, the processor uses the user specific data as an input in generating a first set of rules defining an improvement plan for self-management of stress and relaxation. The first set of rules is adapted to trigger commands instructing the output unit to provide the user with motivation related messages. Also, at least a portion of said user specific data is further used to define a second set of rules indicating the user's personal goals.

U.S. Patent Publication No. 2013/0234823 for method and apparatus to provide an improved sleep experience by selecting an optimal next sleep state for a user by inventors Kahn et al., filed Feb. 28, 2013 and published Sep. 12, 2013, discloses a sleep sensing system comprising a sensor to obtain real-time information about a user, a sleep state logic to determine the user's current sleep state based on the real-time information. The system further comprising a sleep stage selector to select an optimal next sleep state for the user, and a sound output system to output sounds to guide the user from the current sleep state to the optimal next sleep state.

U.S. Pat. No. 8,768,520 for systems and methods for controlling a bedroom environment and for providing sleep data by inventors Oexman et al., filed Nov. 14, 2008 and issued Jul. 1, 2014, discloses a system for controlling a bedroom environment that includes an environmental data collector configured to collect environmental data relating to the bedroom environment; a sleep data collector configured to collect sleep data relating to a person's state of sleep; an analysis unit configured to analyze the collected environmental data and the collected sleep data and to determine an adjustment of the bedroom environment that promotes sleep of the person; and a controller configured to effect the adjustment of the bedroom environment. A method for controlling a bedroom environment includes collecting environmental data relating to the bedroom environment; collecting sleep data relating to a person's state of sleep; analyzing the collected environmental data and the collected sleep data; determining an adjustment to the bedroom environment that promotes sleep; and communicating the adjustment to a device that effects the bedroom environment.

U.S. Patent Publication No. 2014/0277308 for adaptive thermodynamic therapy system by inventors Cronise et al., filed Mar. 17, 2014 and published Sep. 18, 2014, discloses an adaptive thermodynamic therapy system capable of comfortably increasing metabolic expenditure to facilitate excess weight loss, including one or more sensors for measuring a subject user's body temperature, current activity/metabolic level and providing data representative of said body temperature to a computer-based controller, and then actively controlling a thermal load in contact with subject user's body and responsive to the computer-based controller. In one embodiment, the controller is configured to receive input from at least one computer-based device configured to provide user body data and calculate a state value representative of the user body data and to adjust the thermal load to obtain a desired physiological response from the user by modifying the state values.

U.S. Pat. No. 9,186,479 for methods and systems for gathering human biological signals and controlling a bed device by inventors Franceschetti et al., filed Jun. 5, 2015 and issued Nov. 17, 2015, discloses methods and systems for an adjustable bed device configured to: gather biological signals associated with multiple users, such as heart rate, breathing rate, or temperature; analyze the gathered human biological signals; and heat or cool a bed based on the analysis.

U.S. Patent Publication No. 2016/0151603 for methods and systems for sleep management by inventors Shouldice et al., filed Dec. 21, 2015 and published Jun. 2, 2016, discloses a processing system including methods to promote sleep. The system may include a monitor such as a non-contact motion sensor from which sleep information may be determined. User sleep information, such as sleep stages, hypnograms, sleep scores, mind recharge scores and body scores, may be recorded, evaluated and/or displayed for a user. The system may further monitor ambient and/or environmental conditions corresponding to sleep sessions. Sleep advice may be generated based on the sleep information, user queries and/or environmental conditions from one or more sleep sessions. Communicated sleep advice may include content to promote good sleep habits and/or detect risky sleep conditions. In some versions of the system, any one or more of a bedside unit sensor module, a smart processing device, such as a smart phone or smart device, and network servers may be implemented to perform the methodologies of the system.

U.S. Patent Publication No. 2017/0053068 for methods for enhancing wellness associated with habitable environments, filed Aug. 26, 2016 and published Feb. 23, 2017, discloses controlling environmental characteristics of habitable environments (e.g., hotel or motel rooms, spas, resorts, cruise boat cabins, offices, hospitals and/or homes, apartments or residences) to eliminate, reduce or ameliorate adverse or harmful aspects and introduce, increase or enhance beneficial aspects in order to improve a "wellness" or sense of "wellbeing" provided via the environments. Control of intensity and wavelength distribution of passive and active illumination addresses various issues, symptoms or syndromes, for instance to maintain a circadian rhythm or cycle, adjust for "jet lag" or season affective disorder, etc. Air quality and attributes are controlled. Scent(s) may be dispersed. Noise is reduced and sounds (e.g., masking, music, natural) may be provided. Environmental and biometric feedback is provided. Experimentation and machine learning are used to improve health outcomes and wellness standards.

U.S. Patent Publication No. 2017/0231812 for method, device and system for modulating an activity of brown adipose tissue in a vertebrate subject by inventors Boyden et al., filed May 4, 2017 and published Aug. 17, 2017, discloses devices, systems, and methods for treatment of a disease, disorder, or condition in a vertebrate subject. A device is provided that includes one or more cooling elements configured to be applied to one or more tissues of a vertebrate subject to modulate at least one activity of brown adipose tissue of the vertebrate subject, and a programmable controller configured to provide instructions to the one or more cooling elements in response to information regarding one or more physiological conditions of the vertebrate subject.

U.S. Pat. No. 9,750,415 for heart rate variability with sleep detection by inventors Breslow et al., filed Jul. 12, 2016 and issued Sep. 5, 2017, discloses a system using continuous tracking of sleep activity and heart rate activity to evaluate heart rate variability immediately before transitioning to an awake state, e.g., at the end of the last phase of deep sleep. In particular, a wearable, continuous physiological monitoring system includes one or more sensors to detect sleep states, the transitions between sleep states, and the transitions from a sleep state to an awake state for a user. This information can be used in conjunction with continuously monitored heart rate data to calculate heart rate variability of the user at the end of the last phase of sleep preceding the user waking up. By using the history of heart rate data in conjunction with sleep activity in this manner, an accurate and consistent recovery score can be calculated based on heart rate variability.

U.S. Patent Publication No. 2018/0325450 for system for monitoring sleep efficiency by inventor Huang, filed May 7, 2018 and published Nov. 15, 2018, discloses a system for monitoring sleep efficiency includes a measuring device and a data processing device. The measuring device is for measuring body temperature of a subject and for outputting temperature data associated with the body temperature. The data processing device receives the temperature data, and is programmed to process the temperature data so as to determine sleep efficiency. The processing of the temperature data includes constructing a curve of the body temperature over asleep episode, finding a saddle point of the curve occurring for a first time, treating a time instance at which the saddle point occurs as a sleep-onset time point at which the subject falls asleep, and determining the sleep efficiency according to the sleep-onset time point.

U.S. Patent Publication No. 2018/0344517 for methods and apparatuses for the thermal treatment of neurologic and psychiatric disorders by inventor Nofzinger, filed Jun. 6, 2018 and published Dec. 6, 2018, discloses methods and apparatuses for applying region cooling to modulate the autonomic nervous system (and particularly the parasympathetic nervous systems) to treat a medical disorder. Described within are methods and apparatuses for modulating a patient's parasympathetic nervous system by simulating a diving reflex using localized cooling.

U.S. Patent Publication No. 2022/0134050 for Environment Control System And Method For Controlling Environment by inventor Moriyasu, filed Apr. 25, 2019 and published May 5, 2022, discloses an environment control system including: an environment control apparatus installed in a room; a human body state detection unit configured to detect human body sensor information; an environmental state detection unit configured to detect environmental sensor information; a sleep state determination unit configured to determine whether a sleep state is any one of a hypnagogic state, a sleeping state or a wakefulness state; a learning unit configured to learn a predicted sleep rhythm of the human body based on the human body sensor information, the environmental sensor information, and a determination result of the sleep state; a control content determination unit configured to determine control content of the environment control apparatus such that the predicted sleep rhythm obtained by learning approaches an ideal sleep rhythm; and an apparatus control unit configured to control the environment control apparatus based on the control content determined.

U.S. Patent Publication No. 2020/0315368 for Adaptive sleep system using data analytics and learning techniques to improve individual sleep conditions by inventors Tsern et al., filed Feb. 5, 2020 and published Oct. 8, 2020, discloses a bed integrating sensors and other inputs to detect specific sleep environment conditions including point-specific pressure and/or temperature conditions. The bed includes a controller for commanding actuator or other devices to adjust these conditions. The controller may do so based on reference patterns for conditions and profiles of desired conditions. Information regarding the conditions may be provided to a remote computer, which may analyze the conditions and provide revised profiles of desired conditions.

U.S. Patent Publication No. 2009/0121826 for Apparatus and method of managing quality of sleep by inventors Song et al., filed Feb. 5, 2020 and published Oct. 8, 2020, discloses an apparatus of managing quality of sleep including a weight sensor unit including a plurality of pressure sensors, which detect pressures in response to a presence and a movement of a user; an environment sensor including multiple sensors, which detect an environment surrounding the user in a sleep; and a controller for collecting and analyzing information, detected by the weight sensor unit and the environment sensor unit, and classifying and managing the analyzed information according to quality of sleep. The apparatus provides an optimized sleep environment adequate for a subject by learning various sleep environments, and provides a comfortable and cozy sleep environment to the subject to restore energy and be refreshed, so that the subject can enjoy energetic and effective daytime life.

U.S. Pat. No. 11,097,079 for Cognitively inducing sleep cycles by leveraging wearables by inventors Shanmugam et al., filed Nov. 28, 2017 and issued Aug. 24, 2021 discloses a computer-implemented method, system, and computer program product to optimize sleep quality by inducing sleep stages. The method includes: determining a total sleep time; calculating, using the total sleep time, a cycle duration for a sleep cycle, where the sleep cycle includes a first, second, third, fourth, and fifth sleep stage; calculating a first, second, third, fourth, and fifth stage time for the first, second, third, fourth, and fifth sleep stages respectively; generating a first, second, third, fourth, and fifth external parameter for the first, second, third, fourth, and fifth sleep stages respectively, where the external parameters are parameters to facilitate a transition between sleep stages; and executing the first, second, third, fourth, and fifth external parameters upon reaching the calculated stage time for the corresponding sleep stages.

U.S. Patent Publication No. 2021/0146091 for Devices And Systems For Promoting Continuous Sleep Of A Subject And Methods Of Using Same by inventor Kansagra, filed Jan. 28, 2021 and published May 20, 2021, discloses a method for promoting continuous sleep of a subject by eliminating and/or preventing sleep associations including: (a) providing an apparatus including at least one sensor and at least one output device; (b) monitoring a state of the subject using the apparatus; (c) determining the subject is in an awake state using the at least one sensor; (d) in response to determining the subject is in the awake state, initiating and maintaining an output using the at least one output device; (e) determining the subject is in a sleep state using the at least one sensor; (f) halting the output in response to determining that the subject is in the sleep state such that the apparatus does not produce any output; (g) repeating at least step (b) during a sleep session. The method further includes modifying an intensity of the output over time until the intensity reaches zero.

U.S. Pat. No. 11,040,169 for Method and apparatus for controlling temperature adjustment device by inventors Jung et al., filed May 21, 2019 and issued Jun. 22, 2021, discloses a method and an apparatus for controlling a temperature adjustment device using a sensing device. The method includes setting a test temperature, transmitting a temperature adjustment instruction corresponding to the test temperature to a temperature adjustment device, calculating a sleep score based on bio information received from the sensor, when applying the test temperature, and determining a sleep optimal temperature based on the calculated sleep score.

U.S. Patent Publication No. 2020/0027552 for Method for predicting comfortable sleep based on artificial intelligence by inventor Lee, filed Sep. 30, 2019 and published Jan. 23, 2020, discloses a method of analyzing sleep and an AI server having a sleep analysis function. The method of analyzing sleep using an AI server includes receiving sleep state data obtained through a monitoring device; determining factors affecting a sleep time by applying the sleep state data to a previously trained sleep analysis model; and determining an appropriate sleep time by applying the factors affecting the sleep time to the previously trained sleep time estimation model. Therefore, by easily estimating an appropriate sleep time of a user, the method can contribute to a user's health promotion. Artificial intelligent device according to the invention may be linked with an artificial intelligence module, a drone (unmanned aerial vehicle (UAV)), a robot, an augmented reality (AR) device, a virtual reality (VR) device, devices related to 5G services, and the like.

U.S. Patent Publication No. 2020/0205727 for Personalized parameter learning method, sleep-aid device and non-transitory computer readable medium by inventors Shen et al., filed Dec. 26, 2018 and published Jul. 2, 2020, discloses a personalized parameter learning method, a sleep-aid device and a non-transitory computer readable medium. The personalized parameter learning method for a sleep-aid device is provided. The personalized parameter learning method includes the following steps. A process device computes a measured sleep quality of a user after operating a sleep-aid device with an inputted parameter setting at least according to a subjective feedback from the user. The processing device generates a plurality of candidate parameter settings according to the measured sleep quality. The processing device generates a plurality of predicting sleep qualities corresponding the candidate parameter settings. The processing device obtains a recommending parameter setting by selecting one of the candidate parameters according to the predicting sleep qualities.

U.S. Pat. No. 9,993,195 for Personalized sleep disturbance monitoring apparatus and method with correlation of sleep signals and ambiance disturbance signal by inventors Van Vugt et al., filed Nov. 28, 2011 and issued Jun. 12, 2018, discloses a sleep disturbance monitoring apparatus for monitoring a sleep disturbance of a person. An ambience disturbance profile, which describes which levels and/or changes of an ambient signal, which is, for example, a temperature signal or a noise signal, are related to disturbed sleep, is amended depending on a correlation between the ambience signal and a sleep signal which is indicative of the quality of the sleep of the person. After the ambience disturbance profile has been amended, an environmental disturbance factor, which disturbs the sleep, is determined based on a comparison of an actual ambient signal with the amended ambience disturbance profile, wherein information regarding the determined environmental disturbance factor is output to the person on an output unit. This allows providing personalized information regarding environmental sleep disturbance factors, i.e. the information considers the individual susceptibility of a person for environmental disturbances during sleep.

U.S. Patent Publication No. 2021/0031000 for Sleeping Environment Control Device Using Reinforcement Learning by inventors Lee et al., filed Mar. 7, 2019 and published Feb. 4, 2021, discloses a sleeping environment control device using reinforcement learning. The sleeping environment control device using reinforcement learning includes: a main body on which a user is located; a sensor unit configured to measure a biometric signal of the user and generate current state information and post-operation state information; an operation unit configured to control a temperature and humidity of the main body in order to change a sleeping state of the user based on a control signal of a processor; a processor including one or more cores; and a memory configured to store program codes executable in the processor, in which the processor may include: a sleeping adequacy information generation module which generates current sleeping adequacy information of the user based on the current state information and generates post-operation sleeping adequacy information of the user based on the post-operation state information; an operation information determination module which determines operation information controlling an operation of the operation unit by using an operation determination algorithm based on the current sleeping adequacy information; and an operation adequacy determination module which updates the operation determination algorithm by comparing the post-operation sleeping adequacy information with reference sleeping adequacy information and determining adequacy for the operation.

U.S. Pat. No. 11,185,281 for System and method for delivering sensory stimulation to a user based on a sleep architecture model by inventors Molina et al., filed Feb. 19, 2019 and issued Nov. 30, 2021, discloses a system and method for providing sensory stimulation (e.g., tones and/or other sensory stimulation) during sleep. The delivery of the sensory stimulation is timed based on a combination of output from a trained time dependent sleep stage model and output from minimally obtrusive sleep monitoring devices (e.g. actigraphy devices, radar devices, video actigraphy devices, an under mattress sensor, etc.). The disclosure describes determining whether a user is in deep sleep based on this information and delivering sensory stimulation responsive to the user being in deep sleep. In some embodiments, the system comprises one or more sensory stimulators, one or more hardware processors, and/or other components.

U.S. Patent Publication No. 2010/0197996 for System and method for manipulating sleep architecture by sub-awakening non-intrusive stimulations by inventor Cornel, filed Apr. 7, 2010 and published Aug. 5, 2010, discloses a new system and method employing stimulation control to treat sleep disorders, and improve sleep states operating in a dynamic, adaptable manner without causing a premature state of arousal. Stimulation is achieved by controlling a wide variety of environmental factors around the sleeping person. The invention is based on a real-time, self-adaptive feedback system including a sleep and environment monitoring unit or a preset adjustable protocol, an integrating, controlling and deciding unit and a stimulation unit. The system and method take into account individual variability and sensitivity to sensory stimulation and phenomena as adaptation and sensitization. The system and method are aimed at improving the overall sleep architecture, and correcting specific disorders. Alternatively the same invention may be used to promote alertness, specific moods and conditions in the awake subject. The invention may be used by professional in sleep laboratories or by individuals in a home environment. It may be adjusted to operate on groups of people and on non-human subjects.

U.S. Patent Publication No. 2021/0178113 for Systems and methods for audible sleep therapy by inventors Bresch et al., filed Dec. 9, 2020 and published Jun. 17, 2021, discloses a system for providing an audio stimulus to a sleeping user. The system includes a user sensor adapted to acquire user sleep data from the sleeping user and a processor, which is adapted to determine a sleep stage of the sleeping user based on the user sleep data. The processor is further adapted to determine a predicted influence of an audio stimulus on the sleep stage of the sleeping user and generate a control signal based on the predicted influence of the audio stimulus. The system further comprises an audio output device, adapted to receive the control signal and generate an audio stimulus based on the control signal.

U.S. Patent Publication No. 2020/0215295 for Systems and methods for managing ambient conditions by inventors LaPorte et al., filed Aug. 19, 2019 and published Jul. 9, 2020, discloses a system for generating ambient conditions to improve sleep comprising an ambient condition controller. The ambient condition controller may control a light, a speaker, and multiple diffusers. The system may include a computer-readable non-transitory storage medium having instructions that, when executed by a processor, cause the processor to implement a sleep program. The sleep program may cause the ambient condition controller to be configured in a variety of states over a period of time.

SUMMARY OF THE INVENTION

The present invention relates to articles, methods, and systems for non-shivering thermogenesis to enhance sleep recovery and/or promote weight loss.

In one embodiment, the present invention is directed to a system for improving sleep, including a server platform in network communication with at least one regulating device and at least one sensor, wherein the at least one regulating device is operable to adjust parameters of at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module and wherein the artificial intelligence module is operable to recommend an adjustment to parameters of the at least one sleeping article by the at least one regulating device based on the real-time sensor data, wherein the server platform is operable to receive commands to adjust parameters of the at least one sleeping article from at least one user device, wherein the server platform is operable to detect contradictions between the received commands and the recommended adjustments and automatically transmits real-time commands to the at least one regulating device to execute the recommended adjustments if no contradiction is detected, and wherein the at least one regulating device adjusts parameters of the at least one sleeping article based on the real-time commands from the server platform.

In another embodiment, the present invention is directed to a system for improving sleep, including a server platform in network communication with at least one regulating device and at least one sensor, wherein the at least one regulating device is operable to adjust a temperature of at least one sleeping article, wherein the at least one regulating device includes at least one fluid reservoir including thermoelectric modules for heating and/or cooling fluid, and wherein the at least one regulating device is operable to circulate the fluid into and out of the at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module and wherein the artificial intelligence module is operable to recommend an adjustment to the temperature of the at least one sleeping article by the at least one regulating device based on the real-time sensor data, wherein the server platform automatically transmits real-time commands to the at least one regulating device to execute the recommended adjustments, and wherein the at least one regulating device adjusts parameters of the at least one sleeping article based on the real-time commands from the server platform.

In yet another embodiment, the present invention is directed to a system for improving sleep, including a server platform in network communication with at least one regulating device and at least one sensor, wherein the at least one regulating device is operable to adjust parameters of at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module, wherein the artificial intelligence module is trained using global sensor data obtained from a plurality of users, wherein the artificial intelligence module selects a machine learning model for each individual user based on the global sensor data, historical sensor data associated with each individual user and real-time sensor data from each individual user, wherein the artificial intelligence module is operable to recommend an adjustment to parameters of the at least one sleeping article by the at least one regulating device based on the real-time sensor data, wherein the server platform automatically transmits real-time commands to the at least one regulating device to execute the recommended adjustments, and wherein the at least one regulating device adjusts parameters of the at least one sleeping article based on the real-time commands from the server platform.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 9A illustrates a cross-section of a mattress pad with two layers of waterproof material.

FIG. 9B illustrates a cross-section of a mattress pad with two layers of waterproof material and two layers of a second material.

FIG. 9C illustrates a cross-section of a mattress pad with two layers of waterproof material and a spacer layer.

FIG. 9D illustrates a cross-section of a mattress pad with two layers of waterproof material, two layers of a second material, and a spacer layer.

FIG. 29 is a table of average deep sleep percentages by age.

FIG. 30 is a table of target deep sleep percentages by age.

PRIOR ART FIG. 31 illustrates a body with a core and a shell both in a cold environment and a warm environment.

PRIOR ART FIG. 32 illustrates mechanisms of heat loss of the body.

PRIOR ART FIG. 33 illustrates a decrease in core body temperature during a sleep period.

PRIOR ART FIG. 34 illustrates the thermal neutral zone.

PRIOR ART FIG. 35 is a table of resting heart rates for men and women.

PRIOR ART FIG. 36 is an optimal heart rate curve during sleep.

PRIOR ART FIG. 37 is a graph of normal heart rate variability (HRV) values versus age and sex.

DETAILED DESCRIPTION

Figure 1:
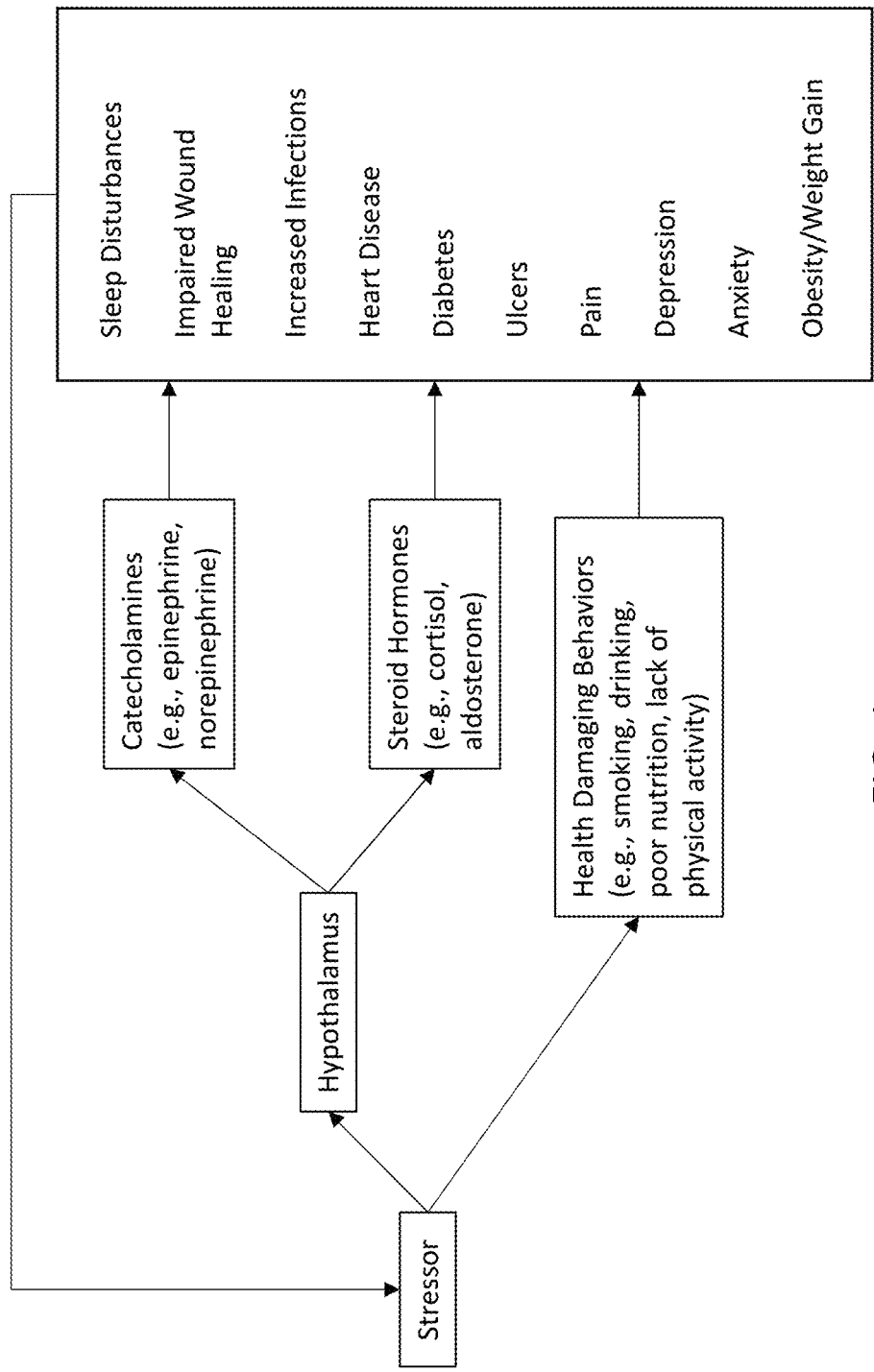
FIG. 1 illustrates the effects of a stressor on the body.

The present invention is generally directed to articles, methods, and systems for non-shivering thermogenesis to enhance sleep recovery and/or promote weight loss.

In one embodiment, the present invention is directed to a system for improving sleep, including a server platform in network communication with at least one regulating device and at least one sensor, wherein the at least one regulating device is operable to adjust parameters of at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module and wherein the artificial intelligence module is operable to recommend an adjustment to parameters of the at least one sleeping article by the at least one regulating device based on the real-time sensor data, wherein the server platform is operable to receive commands to adjust parameters of the at least one sleeping article from at least one user device, wherein the server platform is operable to detect contradictions between the received commands and the recommended adjustments and automatically transmits real-time commands to the at least one regulating device to execute the recommended adjustments if no contradiction is detected, and wherein the at least one regulating device adjusts parameters of the at least one sleeping article based on the real-time commands from the server platform.

In another embodiment, the present invention is directed to a system for improving sleep, including a server platform in network communication with at least one regulating device and at least one sensor, wherein the at least one regulating device is operable to adjust a temperature of at least one sleeping article, wherein the at least one regulating device includes at least one fluid reservoir including thermoelectric modules for heating and/or cooling fluid, and wherein the at least one regulating device is operable to circulate the fluid into and out of the at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module and wherein the artificial intelligence module is operable to recommend an adjustment to the temperature of the at least one sleeping article by the at least one regulating device based on the real-time sensor data, wherein the server platform automatically transmits real-time commands to the at least one regulating device to execute the recommended adjustments, and wherein the at least one regulating device adjusts parameters of the at least one sleeping article based on the real-time commands from the server platform.

In yet another embodiment, the present invention is directed to a system for improving sleep, including a server platform in network communication with at least one regulating device and at least one sensor, wherein the at least one regulating device is operable to adjust parameters of at least one sleeping article, wherein the at least one sleeping article includes at least one mattress, at least one mattress pad, and/or at least one blanket, wherein the server platform receives sensor data from the at least one sensor in real time, wherein the server platform includes an artificial intelligence module, wherein the artificial intelligence module is trained using global sensor data obtained from a plurality of users, wherein the artificial intelligence module selects a machine learning model for each individual user based on the global sensor data, historical sensor data associated with each individual user and real-time sensor data from each individual user, wherein the artificial intelligence module is operable to recommend an adjustment to parameters of the at least one sleeping article by the at least one regulating device based on the real-time sensor data, wherein the server platform automatically transmits real-time commands to the at least one regulating device to execute the recommended adjustments, and wherein the at least one regulating device adjusts parameters of the at least one sleeping article based on the real-time commands from the server platform.

Several studies show a link between stress and illness. Stress often causes physiological changes and lead individuals to adopt health damaging behaviors (e.g., smoking, drinking, poor nutrition, lack of physical activity). These physiological changes and health damaging behaviors cause illnesses, such as sleep disturbances, impaired wound healing, increased infections, heart disease, diabetes, ulcers, pain, depression, and obesity or weight gain.

The body reacts to stress through two systems: the autonomic nervous system and the hypothalamic-pituitary-adrenal (HPA) axis. The autonomic nervous system, which consists of the sympathetic nervous system and the parasympathetic nervous system, is responsible for reacting to short term ("acute") stress. In response to short term stress, the sympathetic nervous system activates the "fight or flight response" through the sympathoadrenal medullary (SAM) axis. This causes the adrenal medulla to secrete catecholamines (e.g., epinephrine and norepinephrine), which causes blood glucose levels to rise, blood vessels to constrict, heart rate to increase, and blood pressure to rise. Blood is diverted from nonessential organs to the heart and skeletal muscles, which leads to decreased digestive system activity and reduced urine output. Additionally, the metabolic rate increases and bronchioles dilate. The parasympathetic nervous system then returns the body to homeostasis.

The HPA axis is responsible for reacting to long term ("chronic") stress. This causes the adrenal cortex to secrete steroid hormones (e.g., mineralocorticoids and glucocorticoids). Mineralocorticoids (e.g., aldosterone) cause retention of sodium and water by the kidneys, increased blood pressure, and increased blood volume. Glucocorticoids (e.g., cortisol) cause proteins and fats to be converted to glucose or broken down for energy, increased blood glucose, and suppression of the immune system.

Thus, stress impacts the body on a cellular level and is a precursor to many disease states. Therefore, it is important to manage and treat stress to maintain health. However, as a result of modern lifestyles, most people are busy, tired, and stressed out. Most people also lack the time and energy to obtain treatments for minor ailments or treatments to prevent disease. What is needed is a convenient treatment that reduces stress and inflammation and promotes healing.

Energy medicine (e.g., biofield therapies, bioelectromagnetic therapies, acupuncture, homeopathy) focuses on the principle that small changes repeated over time change the dynamics of the body and stimulate healing. The present invention utilizes that principle to reduce stress, promote sleep, and stimulate healing. Further, the present invention reduces stress and stimulates healing while a user is resting or sleeping, which is convenient for the user and allows a focused time (e.g., 6-9 hours during a sleeping period) for the user to heal while at home.

Referring now to the drawings in general, the illustrations are for the purpose of describing a preferred embodiment of the invention and are not intended to limit the invention thereto.

FIG. 1 illustrates the effects of a stressor on the body. The body releases catecholamines or steroid hormones as a physiological response to the stressor. Stress also often leads individuals to adopt health damaging behaviors (e.g., smoking, drinking, poor nutrition, lack of physical activity). This sometimes leads to illnesses, such as sleep disturbances, impaired wound healing, increased infections, heart disease, diabetes, ulcers, pain, depression, anxiety, and/or obesity or weight gain. These illnesses themselves frequently become a stressor, which triggers the cycle to continue and causes further physical and mental problems.

Figure 2:
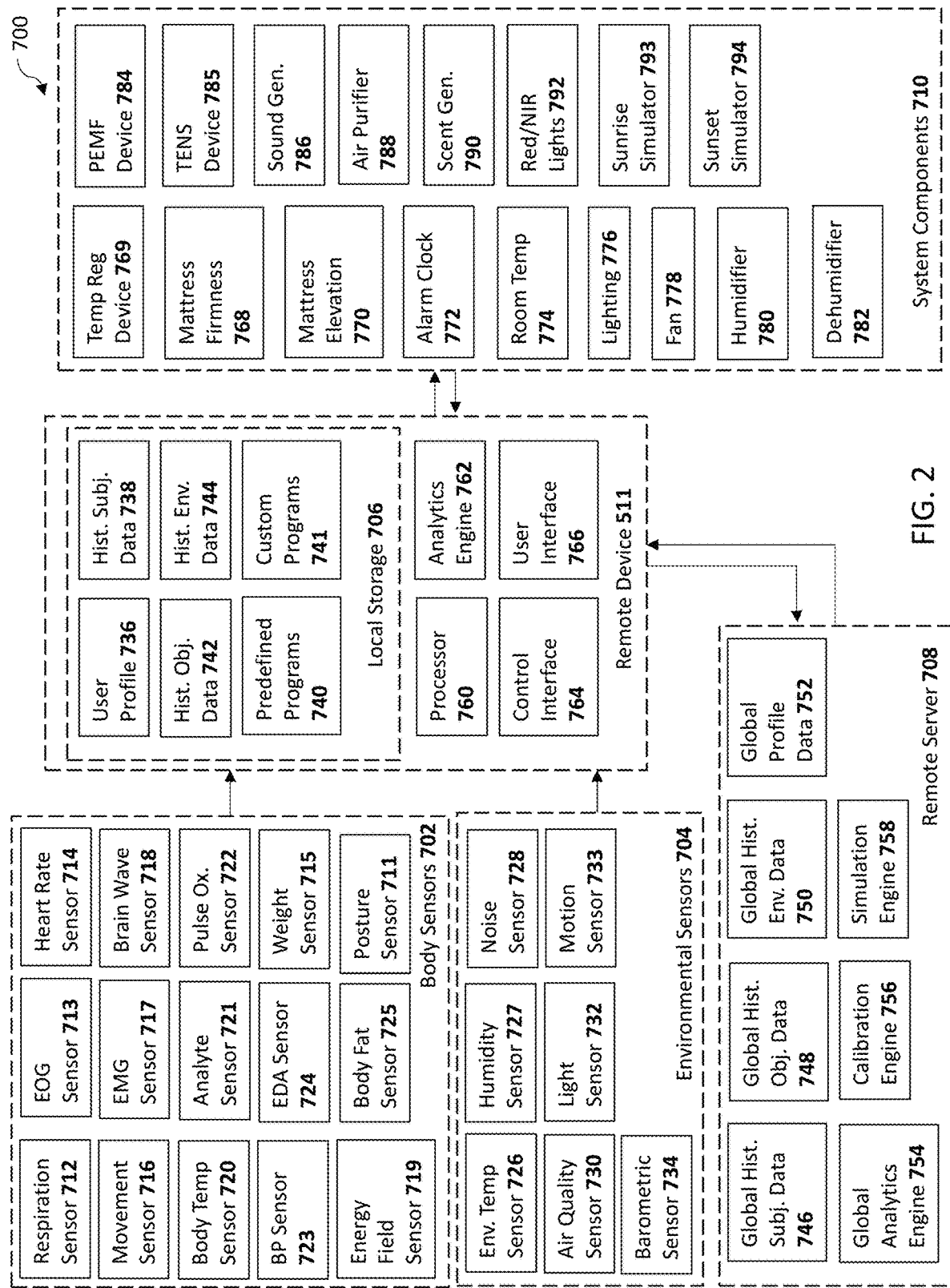
FIG. 2 is a block diagram of one embodiment of a stress reduction and sleep promotion system.

FIG. 2 is a block diagram of one embodiment of the stress reduction and sleep promotion system. The stress reduction and sleep promotion system 700 includes body sensors 702, environmental sensors 704, a remote device 511 with local storage 706, a remote server 708, and system components 710. The body sensors 702 include a posture sensor 711, a respiration sensor 712, an electrooculography (EOG) sensor 713, a heart sensor 714, a body weight sensor 715, a movement sensor 716, an electromyography (EMG) sensor 717, a brain wave sensor 718, a body temperature sensor 720, an analyte sensor 721, a pulse oximeter sensor 722, a blood pressure (BP) sensor 723, an electrodermal activity (EDA) sensor 724, and/or a body fat sensor 725. In one embodiment, at least one body sensor 702 is implanted in the body of a user. In a preferred embodiment, at least one body sensor 702 is operable to transmit data to the remote device 511 and/or the remote server 708 in real time.

The posture sensor 711 measures a posture of an individual. In one embodiment, the posture sensor 711 includes at least one pressure sensor. The at least one pressure sensor is preferably embedded in a seat and/or seat cushion (e.g., DARMA, SENSIMAT). In another embodiment, the posture sensor 711 is a wearable device (e.g., LUMOback Posture Sensor). In another embodiment, the posture sensor 711 includes at least one camera. The at least one camera is operable to detect a posture of the individual using, e.g., computer vision.

The respiration sensor 712 measures a respiratory rate. In one embodiment, the respiration sensor 712 is incorporated into a wearable device (e.g., a chest strap). In another embodiment, the respiration sensor 712 is incorporated into a patch or a bandage. Alternatively, the respiratory rate is estimated from an electrocardiogram, a photoplethysmogram (e.g., a pulse oximeter), and/or an accelerometer. In yet another embodiment, the respiratory sensor 712 uses a non-contact motion sensor to monitor respiration.

The electrooculography (EOG) sensor 713 measures the corneo-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position.

The heart sensor 714 is preferably incorporated into a wearable device (e.g., Apple Watch®, Fitbit®, Jawbone®). Alternatively, the heart sensor 714 is attached to the user with a chest strap. In another embodiment, the heart sensor 714 is incorporated into a patch or a bandage. In yet another embodiment, the heart sensor 714 is incorporated into a sensor device on or under the mattress (e.g., Beddit®, Emfit® QS™). A heart rate is determined using electrocardiogramalse oximetry, ballistocardiography, or seismocardiography. In one embodiment, the heart sensor 714 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincaré plot is generated to display HRV on a device such as a smartphone. In another embodiment, the heart sensor 714 is an electrocardiogram.

The body weight sensor 715 is preferably a smart scale (e.g., Fitbit® Aria®, Nokia® Body+, Garmin® Index™, Under Armour® Scale, Pivotal Living® Smart Scale, iHealth® Core). Alternatively, the body weight sensor 715 is at least one pressure sensor embedded in a mattress or a mattress topper. In one embodiment, the stress reduction and sleep promotion system 700 is also operable to determine a height of a user using the at least one pressure sensor embedded in a mattress or a mattress topper. In another embodiment, a body mass index (BMI) of the user is calculated using the body weight of the user and the height of the user as measured by the at least one pressure sensor.

The movement sensor 716 is an accelerometer and/or a gyroscope. In one embodiment, the accelerometer and/or the gyroscope are incorporated into a wearable device (e.g., Fitbit®, Jawbone®, actigraph). In another embodiment, the accelerometer and/or the gyroscope are incorporated into a smartphone. In alternative embodiment, the movement sensor 716 is a non-contact sensor. In one embodiment, the movement sensor 716 is at least one piezoelectric sensor. In another embodiment, the movement sensor 716 is a pyroelectric infrared sensor (i.e., a "passive" infrared sensor). In yet another embodiment, the movement sensor 716 is at least one pressure sensor embedded in a mattress or mattress topper. Alternatively, the movement sensor 716 is incorporated into a smart fabric. In still another embodiment, the movement sensor 716 is operable to analyze a gait of a user.

The electromyography (EMG) sensor 717 records the electrical activity produced by skeletal muscles. Impulses are recorded by attaching electrodes to the skin surface over the muscle. In a preferred embodiment, three electrodes are placed on the chin. One in the front and center and the other two underneath and on the jawbone. These electrodes demonstrate muscle movement during sleep, which is used to detect REM or NREM sleep. In another embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg are used to detect movement of the legs during sleep, which occurs with Restless Leg Syndrome or Periodic Limb Movements of Sleep.

The brain wave sensor 718 is preferably an electroencephalogram (EEG) with at least one channel. In a preferred embodiment, the EEG has at least two channels. Multiple channels provide higher resolution data. The frequencies in EEG data indicate particular brain states. The brain wave sensor 718 is preferably operable to detect delta, theta, alpha, beta, and gamma frequencies. In another embodiment, the brain wave sensor 718 is operable to identify cognitive and emotion metrics, including focus, stress, excitement, relaxation, interest, and/or engagement. In yet another embodiment, the brain wave sensor 718 is operable to identify cognitive states that reflect the overall level of engagement, attention and focus and/or workload that reflects cognitive processes (e.g., working memory, problem solving, analytical reasoning).

The energy field sensor 719 measures an energy field of a user. In one embodiment, the energy field sensor 719 is a gas discharge visualization (GDV) device. Examples of a GDV device are disclosed in U.S. Pat. Nos. 7,869,636 and 8,321,010 and U.S. Publication No. 20100106424, each of which is incorporated herein by reference in its entirety. The GDV device utilizes the Kirlian effect to evaluate an energy field. In a preferred embodiment, the GDV device utilizes a high-intensity electric field (e.g., 1024 Hz, 10 kV, square pulses) input to an object (e.g., human fingertips) on an electrified glass plate. The high-intensity electric field produces a visible gas discharge glow around the object (e.g., fingertip). The visible gas discharge glow is detected by a charge-coupled detector and analyzed by software on a computer. The software characterizes the pattern of light emitted (e.g., brightness, total area, fractality, density). In a preferred embodiment, the software utilizes Mandel's Energy Emission Analysis and the Su-Jok system of acupuncture to create images and representations of body systems. The energy field sensor 719 is preferably operable to measure stress levels, energy levels, and/or a balance between the left and right sides of the body.

The body temperature sensor 720 measures core body temperature and/or skin temperature. The body temperature sensor 720 is a thermistor, an infrared sensor, or thermal flux sensor. In one embodiment, the body temperature sensor 720 is incorporated into an armband or a wristband. In another embodiment, the body temperature sensor 720 is incorporated into a patch or a bandage. In yet another embodiment, the body temperature sensor 720 is an ingestible core body temperature sensor (e.g., CorTemp®). The body temperature sensor 720 is preferably wireless.

The analyte sensor 721 monitors levels of an analyte in blood, sweat, or interstitial fluid. In one embodiment, the analyte is an electrolyte, a small molecule (molecular weight<900 Daltons), a protein (e.g., C-reactive protein), and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). The analyte sensor 721 is preferably non-invasive. Alternatively, the analyte sensor 721 is minimally invasive or implanted. In one embodiment, the analyte sensor 721 is incorporated into a wearable device. Alternatively, the analyte sensor 721 is incorporated into a patch or a bandage.

The pulse oximeter sensor 722 monitors oxygen saturation. In one embodiment, the pulse oximeter sensor 722 is worn on a finger, a toe, or an ear. In another embodiment, the pulse oximeter sensor 722 is incorporated into a patch or a bandage. The pulse oximeter sensor 722 is preferably wireless. Alternatively, the pulse oximeter sensor 722 is wired. In one embodiment, the pulse oximeter sensor 722 is connected by a wire to a wrist strap or a strap around a hand. In another embodiment, the pulse oximeter sensor 722 is combined with a heart rate sensor 714. In yet another embodiment, the pulse oximeter sensor 722 uses a camera lens on a smartphone or a tablet.

The blood pressure (BP) sensor 723 is a sphygmomanometer. The sphygmomanometer is preferably wireless. Alternatively, the blood pressure sensor 723 estimates the blood pressure without an inflatable cuff (e.g., Salu™ Pulse+). In one embodiment, the blood pressure sensor 723 is incorporated into a wearable device.

The electrodermal activity sensor 724 measures sympathetic nervous system activity. Electrodermal activity is more likely to have high frequency peak patterns (i.e., "storms") during deep sleep. In one embodiment, the electrodermal activity sensor 724 is incorporated into a wearable device. Alternatively, the electrodermal activity sensor 724 is incorporated into a patch or a bandage.

The body fat sensor 725 is preferably a bioelectrical impedance device. In one embodiment, the body fat sensor 725 is incorporated into a smart scale (e.g., Fitbit® Aria®, Nokia® Body+, Garmin® Index™, Under Armour® Scale, Pivotal Living® Smart Scale, iHealth® Core). Alternatively, the body fat sensor 725 is a handheld device.

The environmental sensors 704 include an environmental temperature sensor 726, a humidity sensor 727, a noise sensor 728, an air quality sensor 730, a light sensor 732, a motion sensor 733, and/or a barometric sensor 734. In one embodiment, the environmental temperature sensor 726, the humidity sensor 727, the noise sensor 728, the air quality sensor 730, the light sensor 732, the motion sensor 733, and/or the barometric sensor 734 are incorporated into a home automation system (e.g., Amazon® Alexa®, Apple® HomeKit™, Google® Home™, IF This Then That® (IF-TTT®), Nest®). Alternatively, the environmental temperature sensor 726, the humidity sensor 727, the noise sensor 728, and/or the light sensor 732 are incorporated into a smartphone or tablet. In one embodiment, the noise sensor 728 is a microphone. In one embodiment, the air quality sensor 730 measures carbon monoxide, carbon dioxide, nitrogen dioxide, sulfur dioxide, particulates, and/or volatile organic compounds (VOCs). In another embodiment, at least one environmental sensor 704 is operable to transmit data to the remote device 511 and/or the remote server 708 in real time.

The remote device 511 is preferably a smartphone or a tablet. Alternatively, the remote device 511 is a laptop or a desktop computer. The remote device 511 includes a processor 760, an analytics engine 762, a control interface 764, and a user interface 766. The remote device 511 accepts data input from the body sensors 702 and/or the environmental sensors 704. The remote device also accepts data input from the remote server 708. The remote device 511 stores data in a local storage 706.

The local storage 706 on the remote device 511 includes a user profile 736, historical subjective data 738, predefined programs 740, custom programs 741, historical objective data 742, and historical environmental data 744. The user profile 736 stores stress reduction and sleep promotion system preferences and information about the user, including but not limited to, age, weight, height, gender, medical history (e.g., sleep conditions, medications, diseases), fitness (e.g., fitness level, fitness activities), sleep goals, stress level, and/or occupational information (e.g., occupation, shift information). The medical history includes caffeine consumption, alcohol consumption, tobacco consumption, use of prescription sleep aids and/or other medications, blood pressure, restless leg syndrome, narcolepsy, headaches, heart disease, sleep apnea, depression, stroke, diabetes, insomnia, anxiety or post-traumatic stress disorder (PTSD), and/or neurological disorders.

In one embodiment, the medical history incorporates information gathered from the Epworth Sleepiness Scale (ESS), the Insomnia Severity Index (ISI), Generalized Anxiety Disorder 7-item (GAD-7) Scale, and/or Patient Heath Questionanaire-9 (PHQ-9) (assessment of depression). The ESS is described in Johns M W (1991). "A new method for measuring daytime sleepiness: the Epworth sleepiness scale", *Sleep,* 14 (6). 540-5, which is incorporated herein by reference in its entirety. The ISI is described in Morin et al. (2011). "The Insomnia Severity Index: Psychometric Indicators to Detect Insomnia Cases and Evaluate Treatment Response", Sleep. 34(5): 601-608, which is incorporated herein by reference in its entirety. The GAD-7 is described in Spitzer et al., "A brief measure for assessing generalized anxiety disorder: the GAD-T", *Arch Intern Med.,* 2006 May 22; 166(1): 1092-7, which is incorporated herein by reference in its entirety. The PHQ-9 is described in Kroenke et al., "The PHQ-9: Validity of a Brief Depression Severity Measure", *J. Gen. Intern. Med.,* 2001 September; 16(9): 606-613, which is incorporated herein by reference in its entirety.

In one embodiment, the weight of the user is automatically uploaded to the local storage from a third-party application. In one embodiment, the third-party application obtains the information from a smart scale (e.g., Fitbit® Aria®, Nokia® Body+™, Garmin® Index™, Under Armour® Scale, Pivotal Living® Smart Scale, iHealth® Core). In another embodiment, the medical history includes information gathered from a Resting Breath Hold test.

The historical objective data 742 includes information gathered from the body sensors 702. This includes information from the respiration sensor 712, the electrooculography sensor 713, the heart rate sensor 714, the movement sensor 716, the electromyography sensor 717, the brain wave sensor 718, the energy field sensor 719, the body temperature sensor 720, the analyte sensor 721, the pulse oximeter sensor 722, the blood pressure sensor 723, and/or the electrodermal activity sensor 724. In another embodiment, the historical objective data 742 includes information gathered from the Maintenance of Wakefulness Test, the Digit Symbol Substitution Test, and/or the Psychomotor Vigilance Test. The Maintenance of Wakefulness Test is described in Doghramji, et al., "A normative study of the maintenance of wakefulness test (MWT)", *Electroencephalogr. Clin. Neurophysiol.,* 1997 November; 103(5): 554-562, which is incorporated herein by reference in its entirety. The Digit Symbol Substitution Test is described in Wechsler, D. (1997). Wechsler Adult Intelligence Scale-Third edition (WAIS-III). San Antonio, TX: Psychological Corporation and Wechsler, D. (1997). Wechsler Memory Scale-Third edition (WMS-III). San Antonio, TX: Psychological Corporation, each of which is incorporated herein by reference in its entirety. The Psychomotor Vigilance Test is described in Basner et al., "Maximizing sensitivity of the psychomotor vigilance test (PVT) to sleep loss", Sleep, 2011 May 1; 34(5): 581-91, which is incorporated herein by reference in its entirety.

The historical environmental data 744 includes information gathered from the environmental sensors 704. This includes information from the environmental temperature sensor 726, the humidity sensor 727, the noise sensor 728, the air quality sensor 730, the light sensor 732, and/or the barometric sensor 734.

The historical subjective data 738 includes information regarding sleep and/or stress. In one embodiment, the information regarding sleep is gathered from manual sleep logs (e.g., Pittsburgh Sleep Quality Index). The manual sleep logs include, but are not limited to, a time sleep is first attempted, a time to fall asleep, a time of waking up, hours of sleep, number of awakenings, times of awakenings, length of awakenings, perceived sleep quality, use of medications to assist with sleep, difficulty staying awake and/or concentrating during the day, difficulty with temperature regulation at night (e.g., too hot, too cold), trouble breathing at night (e.g., coughing, snoring), having bad dreams, waking up in the middle of the night or before a desired wake up time, twitching or jerking in the legs while asleep, restlessness while asleep, difficulty sleeping due to pain, and/or needing to use the bathroom in the middle of the night. The Pittsburgh Sleep Quality Index is described in Buysse, et al., "The Pittsburgh sleep quality index: A new instrument for psychiatric practice and research". *Psychiatry Research.* 28 (2). 193-213 (May 1989), which is incorporated herein by reference in its entirety.

In another embodiment, the historical subjective data 738 includes information gathered regarding sleepiness (e.g., Karolinska Sleepiness Scale, Stanford Sleepiness Scale, Epworth Sleepiness Scale). The Karolinska Sleepiness Scale is described in Åkerstedt, et al., "Subjective and objective sleepiness in the active individual", *Int J Neurosc.,* 1990; 52:29-37 and Baulk et al., "Driver sleepiness-evaluation of reaction time measurement as a secondary task", Sleep, 2001; 24(6):695-698, each of which is incorporated herein by reference in its entirety. The Stanford Sleepiness Scale is described in Hoddes E. (1972). "The development and use of the Stanford sleepiness scale (SSS)". *Psychophysiology* 9 (150) and Maclean, et al. (1992-03-01). "Psychometric evaluation of the Stanford Sleepiness Scale". *Journal of Sleep Research.* 1 (1): 35-39, each of which is incorporated herein by reference in its entirety.

In yet another embodiment, the historical subjective data 738 includes information regarding tension or anxiety, depression or dejection, anger or hostility, and/or fatigue or inertia gathered from the Profile of Mood States. The Profile of Mood States is described in the Profile of Mood States, $2^{nd}$ Edition published by Multi-Health Systems (2012) and Curran et al., "Short Form of the Profile of Mood States (POMS-SF): Psychometric information", *Psychological Assessment.* 7 (1): 80-83 (1995), each of which is incorporated herein by reference in its entirety. In another embodiment, the historical subjective data 738 includes information gathered from the Ford Insomnia Response to Stress Test (FIRST), which asks how likely a respondent is to have difficulty sleeping in nine different situations. The FIRST is described in Drake et al., "Vulnerability to stress-related sleep disturbance and hyperarousal", *Sleep,* 2004; 27:285-91 and Drake et al., "Stress-related sleep disturbance and polysomnographic response to caffeine", *Sleep Med.,* 2006; 7:567-72, each of which is incorporated herein by reference in its entirety. In still another embodiment, the historical subjective data 738 includes information gathered from the Impact of Events, which assesses the psychological impact of stressful life events. A subscale score is calculated for intrusion, avoidance, and/or hyperarousal. The Impact of Events is described in Weiss, D. S., & Marmar, C. R. (1996). The Impact of Event Scale—Revised. In J. Wilson & T. M. Keane (Eds.), Assessing psychological trauma and PTSD (pp. 399-411). New York: Guilford, which is incorporated herein by reference in its entirety. In one embodiment, the historical subjective data 738 includes information gathered from the Social Readjustment Rating Scale (SRRS). The SRRS lists 52 stressful life events and assigns a point value based on how traumatic the event was determined to be by a sample population. The SRRS is described in Holmes et al., "The Social Readjustment Rating Scale", *J. Psychosom. Res.* 11(2): 213-8 (1967), which is incorporated herein by reference in its entirety.

In one embodiment, the predefined programs 740 are general sleep settings for various conditions and/or body types (e.g., weight loss, comfort, athletic recovery, hot flashes, bed sores, depression, multiple sclerosis, alternative sleep cycles). In one embodiment, a weight loss predefined program sets a surface temperature at a very cold setting (e.g., 15.56-18.89° C. (60-66° F.)) to increase a metabolic response, resulting in an increase in calories burned, which then leads to weight loss. Temperature settings are automatically adjusted to be as cold as tolerable by the user after the first sleep cycle starts to maximize the caloric burn while having the smallest impact on sleep quality. The core temperature of an overweight individual sometimes fails to drop due to a low metabolism. In one example, the surface temperature is 20° C. (68° F.) at the start of a sleep period, 18.89° C. (66° F.) during N1-N2 sleep, 18.33° C. (65° F.) during N3 sleep, 19.44° C. (67° F.) during REM sleep, and 20° C. (68° F.) to wake the user.

In one embodiment, the custom programs 741 are sleep settings defined by the user. In one example, the user creates a custom program by modifying a predefined program (e.g., the weight loss program above) to be 1.11° ° C. (2° F.) cooler during the N3 stage. In another example, the user creates a custom program by modifying a predefined program to have a start temperature of 37.78° C. (100° F.). The custom programs 741 allow a user to save preferred sleep settings.

The remote server 708 includes global historical subjective data 746, global historical objective data 748, global historical environmental data 750, global profile data 752, a global analytics engine 754, a calibration engine 756, a simulation engine 758, and a reasoning engine 759. The global historical subjective data 746, the global historical objective data 748, the global historical environmental data 750, and the global profile data 752 include data from multiple users.

The system components 710 include a mattress pad 11 with adjustable temperature control, a mattress with adjustable firmness 768, a mattress with adjustable elevation 770, an alarm clock 772, a thermostat to adjust the room temperature 774, a lighting system 776, a fan 778, a humidifier 780, a dehumidifier 782, a pulsed electromagnetic field (PEMF) device 784, a transcutaneous electrical nerve stimulation (TENS) device 785, a sound generator 786, an air purifier 788, a scent generator 790, a red light and/or near-infrared lighting device 792, a sunrise simulator 793, and/or a sunset simulator 794. In other embodiments, the system components include a blanket, a pillow, a cap, a head wrap, a vest, a sleeping bag, a cocoon, and/or a body wrap with adjustable temperature control. In yet another embodiment, temperature is controlled with a mattress with temperature control (e.g., temperature adjusted with a fluid, such as water or air). Although temperature is described herein as being adjusted or controlled by a mattress pad, it is equally likely that temperature is adjusted or controlled by the blanket, the pillow, the cap, the head wrap, the vest, the sleeping bag, the cocoon, the body wrap, and/or the mattress with temperature control.

The body sensors 702, the environmental sensors 704, the remote device 511 with local storage 706, the remote server 708, and the system components 710 are designed to connect directly (e.g., Universal Serial Bus (USB) or equivalent) or wirelessly (e.g., Bluetooth®, Wi-Fi®, ZigBee®) through systems designed to exchange data between various data collection sources. In a preferred embodiment, the body sensors 702, the environmental sensors 704, the remote device 511 with local storage 706, the remote server 708, and the system components 710 communicate wirelessly through Bluetooth®. Advantageously, Bluetooth® emits lower electromagnetic fields (EMFs) than Wi-Fi® and cellular signals.

Additional information regarding the stress reduction and sleep promotion system in in U.S. Publication Nos. 20180000255 and 20180110960 and U.S. application Ser. No. 16/686,394, filed Nov. 18, 2019, each of which is incorporated herein by reference in its entirety. U.S. Application No. 62/792,572, filed Jan. 15, 2019, discusses a health data exchange platform and is incorporated herein by reference in its entirety.

Figure 3:
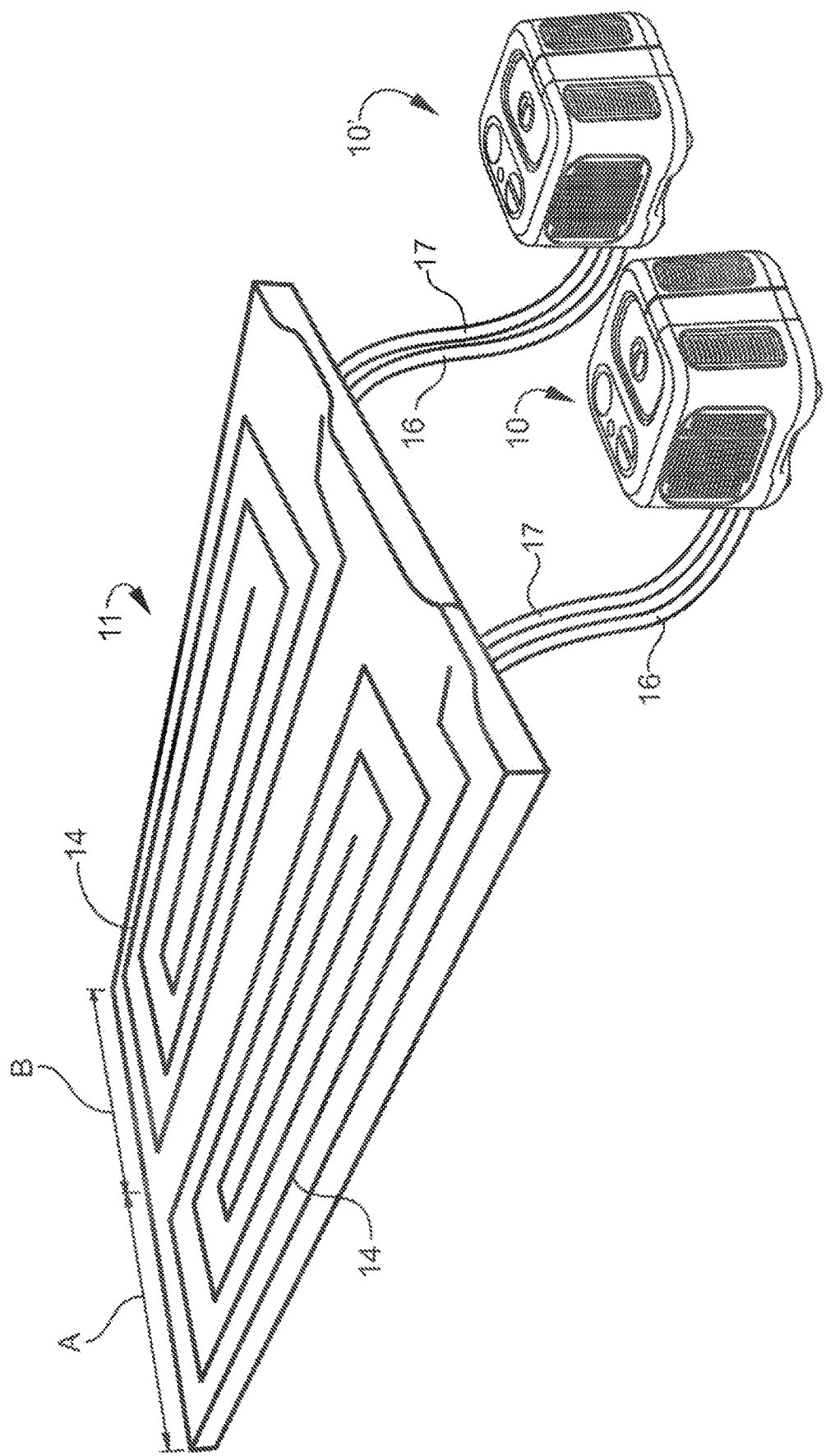
FIG. 3 is an environmental perspective view of a temperature-regulated mattress pad having two surface temperature zones connected to respective thermoelectric control units according to one exemplary embodiment of the present invention.
Figure 4:
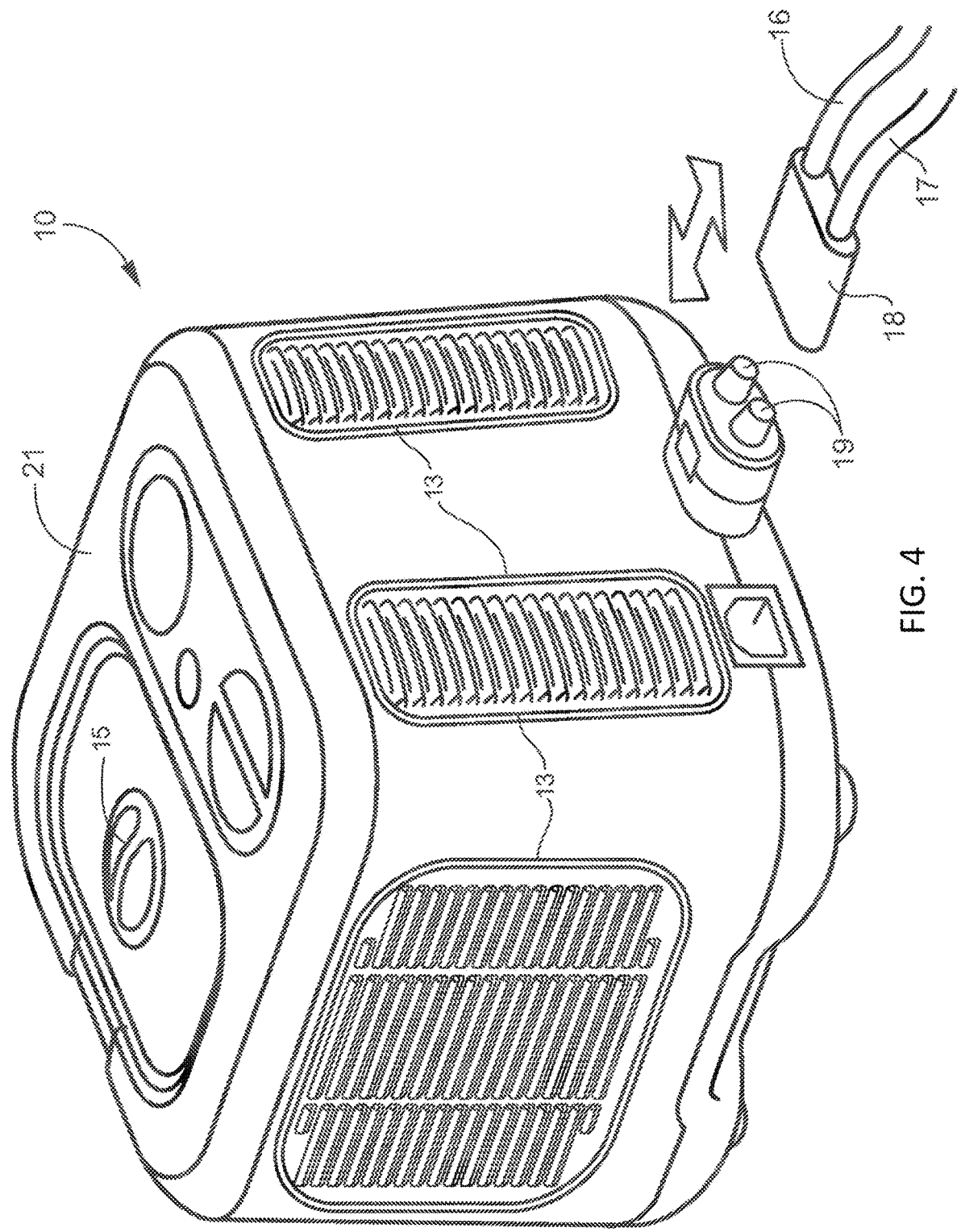
FIG. 4 is a perspective view of the exemplary control unit demonstrating the quick connection/disconnection of the flexible fluid supply and return lines.

In a preferred embodiment, the stress reduction and sleep promotion system 700 includes a mattress pad 11 to change the temperature of the sleep surface. FIG. 3 illustrates a thermoelectric control unit 10 according to the present invention. As shown, a pair of identical control units 10, 10' attach through flexible conduit to a temperature-conditioned article, such as mattress pad 11. The mattress pad 11 has two independent thermally regulated surface zones "A" and "B", each containing internal flexible (e.g., silicon) tubing 14 designed for circulating heated or cooled fluid within a hydraulic circuit between the control unit 10 and the mattress pad 11. As best shown in FIGS. 3 and 4, the flexible conduit assembly for each control unit 10 includes separate fluid supply and return lines 16, 17 connected to tubing 14, and a quick-release female connector 18 for ready attachment and detachment to external male connectors 19 of the control unit 10. Advantageously, the mattress pad 11 allows a user to retrofit an existing mattress.

In one embodiment, the thermoelectric control unit 10 is operatively connected (e.g., by flexible conduit) to a mattress, such that the temperature-conditioned surface is embedded in the mattress itself. In alternative exemplary embodiments, the thermoelectric control unit 10 is operatively connected (e.g., by flexible conduit) to any other temperature regulated article, such as a blanket or other bedding or covers, seat pad, sofa, chair, or the like.

Figure 5:
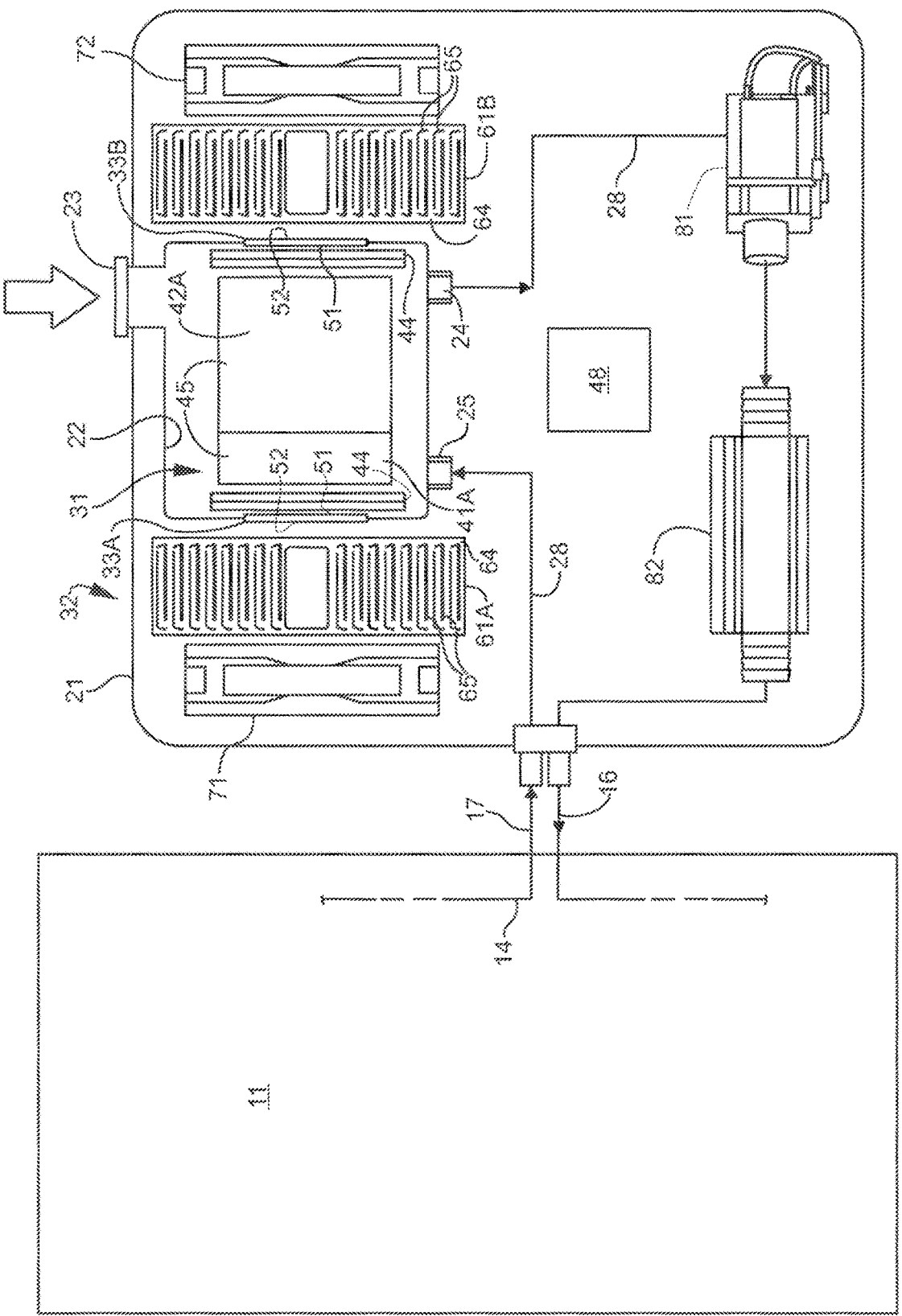
FIG. 5 is a side schematic view showing various internal components of the exemplary control unit fluidly connected to the mattress pad.
Figure 6:
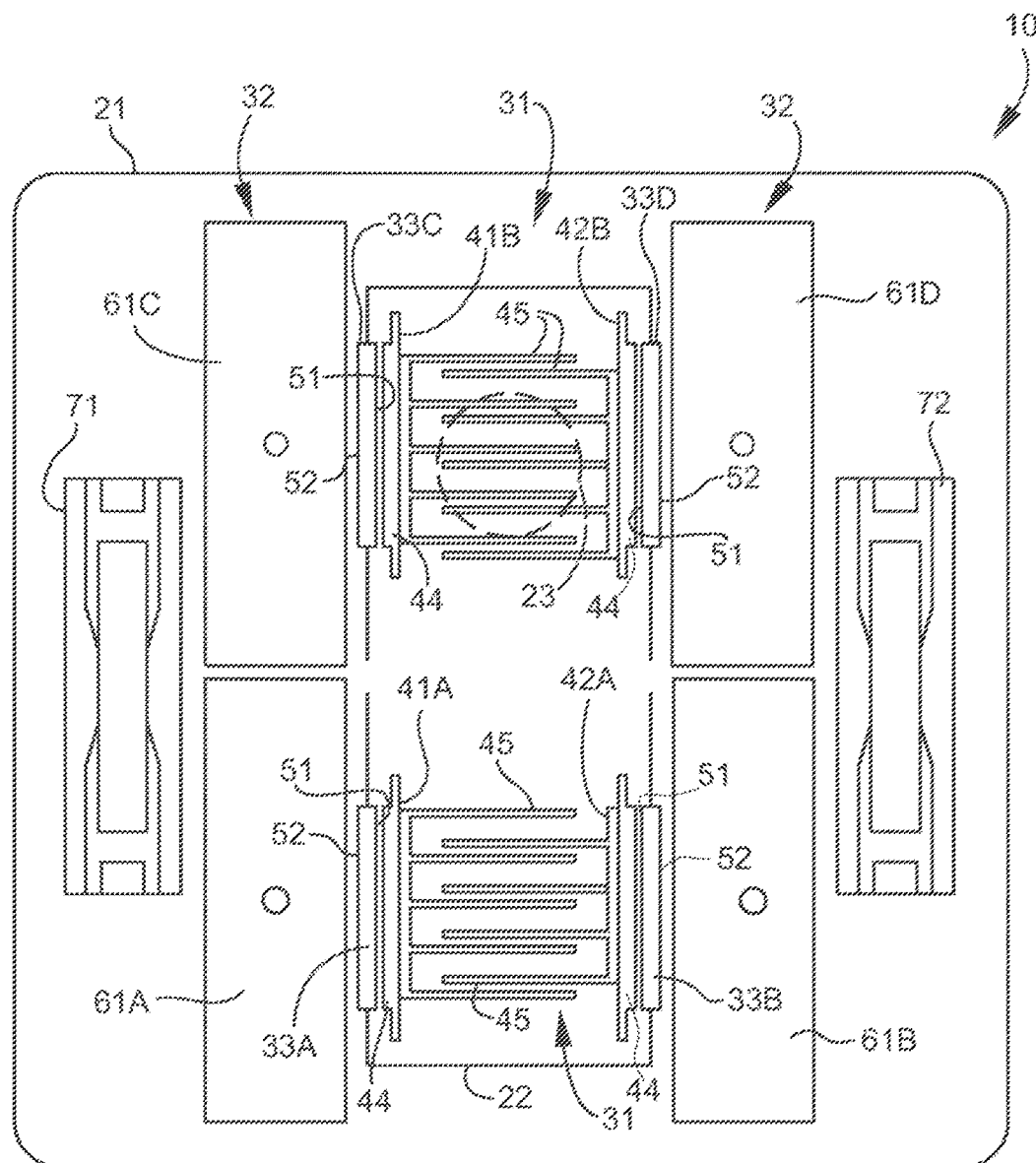
FIG. 6 is a top schematic view of the exemplary control unit.

As illustrated in FIGS. 5 and 6, the exemplary control unit 10 has an external housing 21, and a fluid reservoir 22 located inside the housing 21. The reservoir 22 has a fill opening 23 accessible through a removably capped opening 15 (FIG. 4) in housing 21, a fluid outlet 24, and a fluid return 25. Fluid contained in the reservoir 22 is moved in a circuit through a conduit assembly formed from in-housing tubes 28, the flexible supply and return lines 16, 17, and flexible silicone tubing 14 within the temperature-regulated pad 11. The fluid is selectively cooled, as described further below, by cooperating first and second heat exchangers 31, 32 and thermoelectric cooling modules 33A-33D. The cooling modules 33A-33D reside at an electrified junction between the first and second heat exchangers 31, 32, and function to regulate fluid temperature from a cool point of as low as 7.78° C. (46° F.), or cooler. The housing 21 and reservoir 22 are either separately or integrally constructed of any suitable material, such as an anti-flammable ABS, polypropylene, or other molded polymer.

Referring to FIGS. 5 and 6, the first heat exchanger 31 is formed of pairs of oppositely directed internal heat sinks 41A, 42A and 41B, 42B communicating with an inside of the reservoir 22, and cooperating with thermoelectric cooling modules 33A-33D to cool the fluid inside the reservoir 22 to a selected (set) temperature. Each heat sink 41A, 42A, 41B, 42B has a substantially planar metal base 44 adjacent an exterior side wall of the reservoir 22, and a plurality of planar metal fins 45 extending substantially perpendicular to the base 44 and vertically inward towards a center region of the reservoir 22. In the exemplary embodiment, each pair of heat sinks 41A, 42A and 41B, 42B is formed from one 4-fin sink and one 5-fin sink arranged such that their respective fins 45 are facing and interleaved as shown in FIG. 6. The exemplary cooling modules 33A-33D are operatively connected to an internal power supply/main control board 48, and are formed from respective thin Peltier chips having opposing planar inside and outside major surfaces 51, 52. The inside major surface 51 of each cooling module 33A-33D resides in direct thermal contact with the planar base 44 of its corresponding heat sink 41A, 42A, 41B, 42B. A thermal pad or compound (not shown) resides between each cooling module 33A-33D and heat sink 41A, 42A, 41B, 42B to promote thermal conduction from base 44 outwardly across the fins 45.

The second heat exchanger 32 is formed from external heat sinks 61A-61D located outside of the fluid reservoir 22, and arranged in an opposite-facing direction to respective internal heat sinks 41A, 42A, 41B, 42B. Each external heat sink 61A-61D has a planar metal base 64 in direct thermal contact with the outside major surface 52 of an associated adjacent cooling module 33A-33D, and a plurality of planar metal fins 65 extending substantially perpendicular to the base 64 and horizontally outward away from the fluid reservoir 22. Heat generated by the cooling modules 33A-33D is conducted by the external heat sinks 61A-61D away from the modules 33A-33D and dissipated to a surrounding environment outside of the fluid reservoir 22. Electric case fans 71 and 72 are operatively connected to the power supply/main control board 48 and mounted inside the housing 21 adjacent respective heat sinks 61A, 61B and 61C, 61D. The exemplary fans 71, 72 promote air flow across the sink fins 65, and outwardly from the control unit 10 through exhaust vents 13 formed with the sides and bottom of the housing 21. In one embodiment, each external heat sink 61A-61D has a substantially larger base 64 (as compared to the 4-fin and 5-fin internal sinks 41A, 42A, 41B, 42B) and a substantially greater number of fins 65 (e.g., 32 or more). Both internal and external heat sinks are active or passive, and are constructed of any suitable conductive material, including aluminum, copper, and other metals. In one embodiment, the heat sinks have a thermal conductivity of 400 watts per meter-Kelvin (W/(m·K)), or more. In one embodiment, the case fans 71, 72 automatically activate and shut off as needed.

From the reservoir 22, the temperature conditioned fluid exits through the outlet 24 and enters the conduit assembly formed from an arrangement of in-housing Z-, L-, 7-, and S-shaped tubes 28 (and joints). A pump 81 is operatively connected to the reservoir 22 and functions to circulate the fluid through the control unit 10 in a circuit including the in-housing tubes 28 (and joints), flexible fluid supply line 16, silicone pad tubes 14, fluid return line 17, and back into the reservoir 22 through fluid return 25. As shown in FIG. 5, an insulated linear heat tube 82 is located outside of the fluid reservoir 22 and inside the housing 21, and communicates with the conduit assembly to selectively heat fluid moving from the control unit 10 to the mattress pad 11. The exemplary heat tube 82 heats fluid moving in the hydraulic circuit to a desired temperature of as warm as 47.78° C. (118° F.).

The control unit has at least one fluid reservoir. In one embodiment, the control unit includes two fluid reservoirs. A first fluid reservoir is used to heat and/or cool fluid that circulates through the temperature-regulated pad. The first fluid reservoir includes at least one sensor to measure a level of the fluid. A second fluid reservoir is used to store fluid. In a preferred embodiment, fluid from the second fluid reservoir is automatically used to fill the first fluid reservoir when the at least one sensor indicates that the level of the fluid is below a minimum value. Advantageously, this optimizes the temperature in the first fluid reservoir because only a small amount of stored fluid is introduced into the first fluid reservoir when needed. Additionally, this embodiment reduces the refilling required for the control unit, saving the user time and effort. In one embodiment, the at least one fluid reservoir is formed of metal. In another embodiment, the metal of the at least one fluid reservoir is electrically connected to ground.

Figure 7:
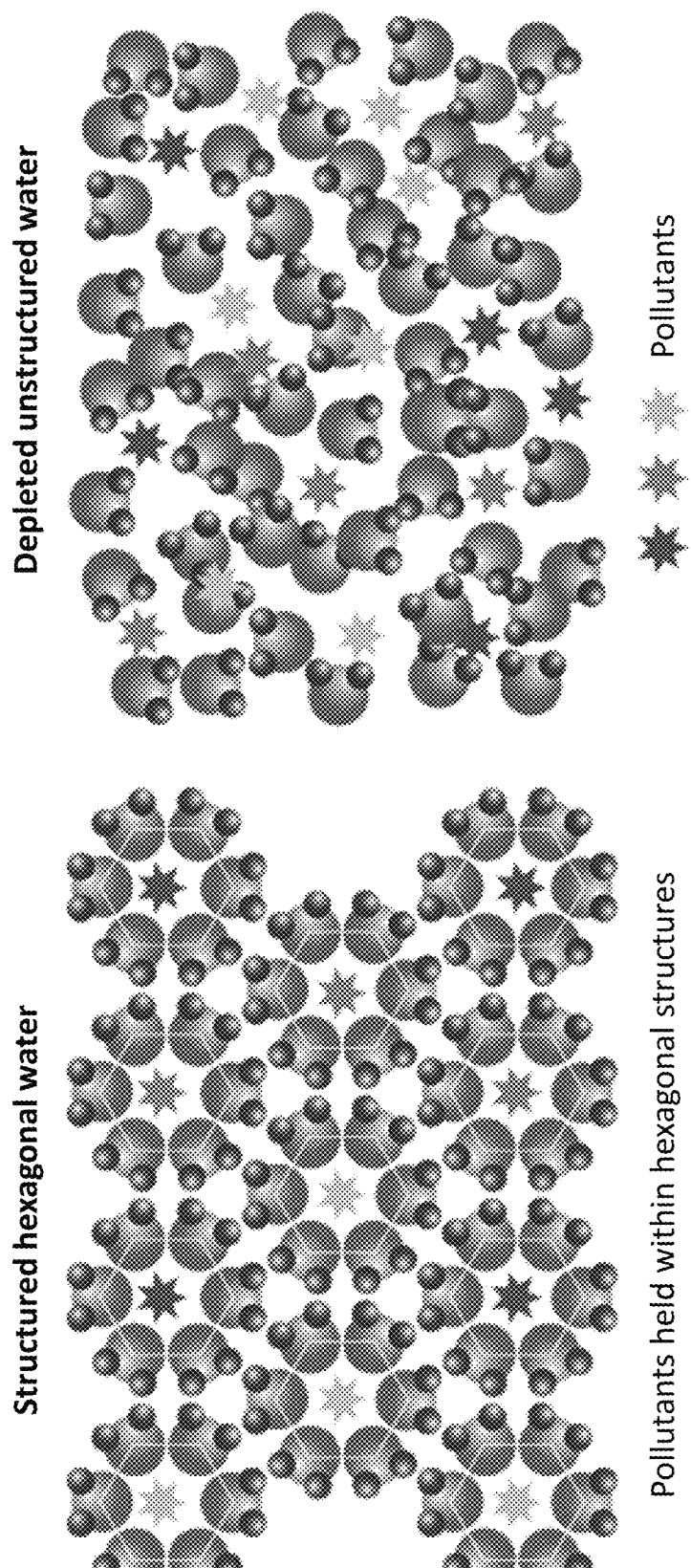
FIG. 7 illustrates the difference between structured water and unstructured water.

In a preferred embodiment, the control unit includes at least one mechanism for forming structured water. FIG. 7 illustrates the difference between structured water and unstructured water. In one embodiment, the control unit includes at least one vortex to treat the fluid. The at least one vortex reduces bacteria, algae, and fungus in the fluid without using additional chemicals. In one embodiment, the at least one vortex includes at least one left spin vortex and at least one right spin vortex. The at least one left spin vortex and the at least one right spin vortex mimics the movement of water in nature. One example of utilizing vortex technologies to treat fluids is described in U.S. Pat. No. 7,238,289, which is incorporated herein by reference in its entirety. Alternatively, the fluid flows or tumbles over or through a series of balls and/or rocks. In one embodiment, the rocks are in a hexagonal shape. A tumbling action or vortex aligns the molecules in the structured water to retain energy (i.e., cooling or heating) for a longer period of time. Surprisingly, the aligned or structured water molecules produce a 20% increase in the heating and cooling capacity of the water.

In a preferred embodiment, the fluid is water. In one embodiment, the water is treated with an ultraviolet (UV) purification system to kill microorganisms (e.g., bacteria, viruses, molds). The UV purification system includes at least one UV light bulb to expose microorganisms to UV radiation, which prevents the microorganisms from reproducing. This reduces the number of microorganisms in the water without using additional chemicals. In one embodiment, the at least one UV light bulb is a UV-C light emitting diode (LED). In another embodiment, the at least one UV light bulb is a mercury vapor bulb.

Additionally or alternatively, the water is treated with at least one filter to remove contaminants and/or particles. In a preferred embodiment, the at least one filter clarifies the water before exposure to the at least one UV light bulb. Contaminants and/or particles in the water are larger than the microorganisms, so contaminants and/or particles block the UV rays from reaching the microorganisms. In one embodiment, the at least one filter is a sediment filter, an activated carbon filter, a reverse osmosis filter, and/or a ceramic filter. In another embodiment, one or more of the at least one filter includes copper and/or silver (e.g., nanoparticles, ions, colloidal) to suppress the growth of microorganisms. Contaminants and/or particles that are removed from the water include sediment, rust, calcium carbonate, organic compounds, chlorine, and/or minerals.

The at least one filter preferably removes contaminants and/or particles with a diameter greater than 0.3 µm. Alternatively, the at least one filter removes contaminants and/or particles with a diameter greater than 0.5 µm. In another embodiment, the at least one filter removes contaminants and/or particles with a diameter greater than 0.05 µm. In another embodiment, the at least one filter removes contaminants and/or particles with a diameter greater than 1 nm.

In one embodiment, the water is treated with copper and/or silver ions. The copper and/or silver ions are positively charged and bond with negative sites on cell walls of microorganisms. This leads to the deactivation of proteins and ultimately to cell death. Copper and/or silver ions also are able to destroy biofilms and slimes. In one embodiment, the copper and/or silver ions are created through electrolysis.

Alternatively, the water is treated with at least one chemical to inhibit growth of bacteria and microorganisms or to remove lime and calcium buildup. In one embodiment, the water is treated with a compound containing iodine or chlorine. In another embodiment, the water is treated with salt and/or a peroxide solution. In yet another embodiment, the water is treated with citric acid.

The thermoelectric control unit further includes other features and electronics not shown. In one embodiment, the control unit includes a touch control and display board, overheat protectors, fluid level sensor, thermostat, additional case fans, and/or at least one speaker. The control unit also includes an external power cord designed to plug into standard household electrical outlets, or is powered using rechargeable or non-rechargeable batteries. In one embodiment, the touch control and display board includes a power button, temperature selection buttons (e.g., up arrow and down arrow), and/or an LCD to display the temperature. In another embodiment, the touch control and display board includes a program selection menu.

The control unit preferably has at least one processor. By way of example, and not limitation, the processor is a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that performs calculations, process instructions for execution, and/or other manipulations of information. In one embodiment, one or more of the at least one processor is operable to run predefined programs stored in at least one memory of the control unit.

The control unit preferably includes at least one antenna, which allows the control unit to receive and process input data (e.g., temperature settings, start and stop commands) from at least one remote device (e.g., smartphone, tablet, laptop computer, desktop computer, remote control). In a preferred embodiment, the at least one remote device is in wireless network communication with the control unit. The wireless communication is, by way of example and not limitation, radiofrequency, Bluetooth®, ZigBee®, Wi-Fi®, wireless local area networking, near field communication (NFC), or other similar commercially utilized standards. Alternatively, the at least one remote device is in wired communication with the control unit through USB or equivalent.

In a preferred embodiment, the at least one remote device is operable to set target temperatures for the mattress pad. The at least one remote device preferably has a user interface (e.g., a mobile application for a smartphone or tablet, buttons on a remote control) that allows a user to select target temperatures for the mattress pad or independent zones within the mattress pad. In one embodiment, the mattress pad includes temperature probes in each zone that provide temperature data for that zone to the at least one processor, which compares a target temperature set using the at least one device to an actual measured temperature to determine whether to heat or cool the fluid and determine where to distribute the heated or cooled fluid in order to make the actual temperature match the target temperature.

Those skilled in the art will recognize that programmatic control of the target temperatures over time, such as over the course of a night's sleep, is possible using the at least one remote device. Because the target temperatures can be set at any time, those target temperatures can be manipulated through the sleeping period in order to match user preferences or a program to correlate with user sleep cycles to produce a deeper, more restful sleep.

Figure 8A:
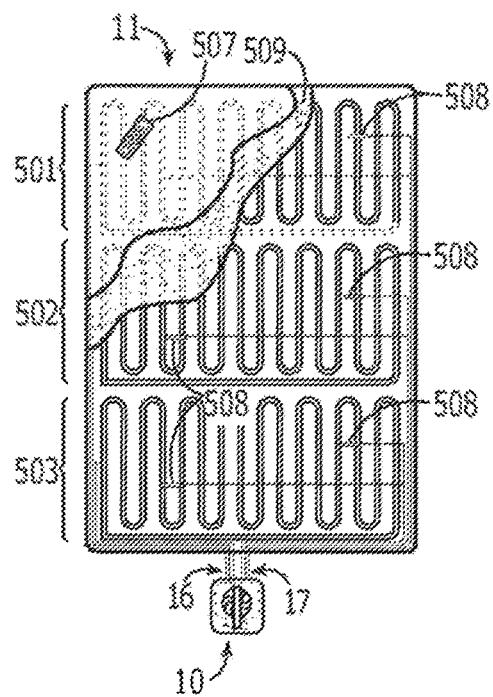
FIG. 8A illustrates one embodiment of a mattress pad with three independent temperature zones.

FIG. 8A illustrates one embodiment of a mattress pad with three independent temperature zones. The three independent temperature zones 501, 502, 503 generally correspond to the head, body and legs, and feet, respectfully, of a user. Although only three zones are shown, it is equally possible to have one, two, four, or more independent temperature zones. A wireless remote control 507 is used to set the target temperatures for each of the zones 501, 502, 503. Fluid is delivered to the mattress pad 11 from the control unit 10 via a fluid supply line 16 that enters the continuous perimeter via an opening sized to sealingly receive the fluid supply line 16. Fluid is removed from the mattress pad 11 and returned to the control unit 10 via a fluid return line 17 that exits the continuous perimeter via an opening sized to sealingly receive the fluid return line 17.

Temperature probes 508 in each zone provide actual measured temperature data for that zone to the control unit 10. The control unit 10 compares the target temperature set using the wireless remote control 507 and the actual measured temperature to determine whether to heat or cool the fluid and determine to which conduit or circuits the heated or cooled fluid should be distributed in order to make the actual temperature match the target temperature.

In one embodiment, a larger number of temperature probes are in the independent temperature zones corresponding to the core body region, and a smaller number of temperature probes are in the independent temperature zones not corresponding to the core body region. In one example, zone 501 contains three temperature probes, zone 502 contains five temperature probes, and zone 503 contains three temperature probes. This embodiment provides the advantage of more closely monitoring the temperature of the pad in the core body region, which is important because core body temperature impacts how well a user sleeps.

In another embodiment, an independent temperature zone contains three temperature probes. In one example, zone 501 contains a temperature probe in the center of the mattress pad 11, a temperature probe on the left side of the mattress pad 11, and a temperature probe on the right side of the mattress pad 11. Advantageously, this embodiment provides information about the left, center, and right of the mattress pad. In yet another embodiment, an independent temperature zone contains at least three temperature probes.

The mattress pad includes padding 509 between the conduit circuits and the resting surface, in order to improve the comfort of a user and to prevent the concentrated heat or cold of the conduit circuits from being applied directly or semi-directly to the user's body. Instead, the conduit circuits heat or cool the padding 509, which provides more gentle temperature modulation for the user's body.

Figure 8B:
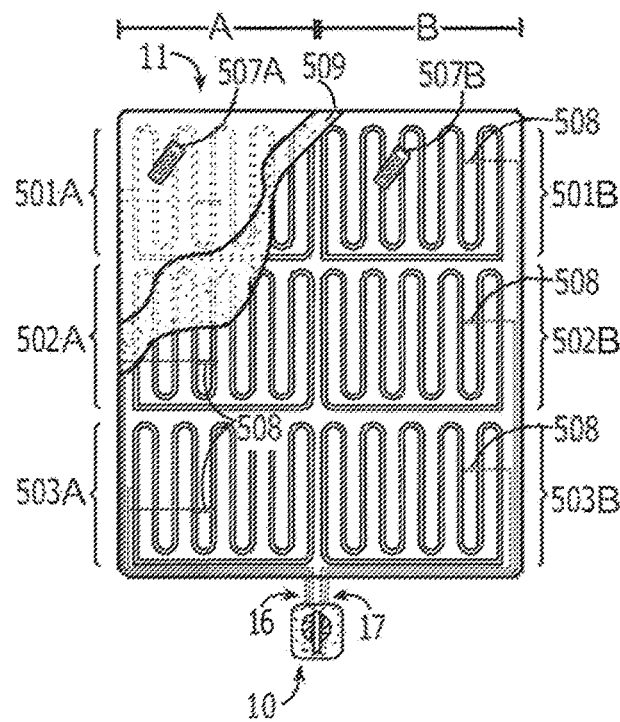
FIG. 8B illustrates one embodiment of a double mattress pad with three independent temperature zones for both users.

FIG. 8B illustrates one embodiment of a double mattress pad. Three independent temperature zones 501A, 502A, 503A generally correspond to the head, body and legs, and feet, respectfully, of a first user who utilizes surface zone "A". Three independent temperature zones 501B, 502B, 503B generally correspond to the head, body and legs, and feet, respectfully, of a second user who utilizes surface zone "B". Although only three zones are shown for each user, it is equally possible to have one, two, four, or more independent temperature zones. A first wireless remote control 507A is used to set the target temperatures for each of the zones 501A, 502A, 503A. A second wireless remote control 507B is used to set the target temperatures for each of the zones 501B, 502B, 503B. Temperature probes 508 in each zone provide actual measured temperature data for that zone to the control unit 10. The control unit 10 compares the target temperature set using the wireless remote control 507A, 507B and the actual measured temperature to determine whether to heat or cool the fluid and determine to which conduit or circuits the heated or cooled fluid should be distributed in order to make the actual temperature match the target temperature.

In this embodiment, despite the presence of two separate controls, a single control unit 10 is utilized to control the temperature of the fluid. In another embodiment, a first control unit is utilized to control the temperature of the fluid for the first user and a second control unit is utilized to control the temperature of the fluid for the second user. Alternatively, each user has at least two control units to control the temperature of the fluid.

Figure 8C:
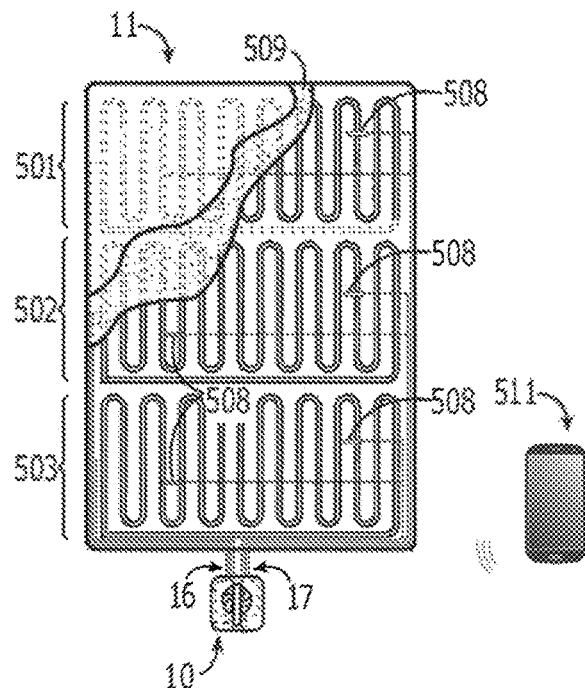
FIG. 8C illustrates one embodiment of a mattress pad with three independent temperature zones connected to at least one remote device.

FIG. 8C illustrates one embodiment of a mattress pad with three independent temperature zones connected to at least one remote device 511. In a preferred embodiment, the at least one remote device is a smartphone or a tablet. The at least one remote device preferably has a mobile application that allows for the control unit 10 to vary the temperature of the mattress pad 11 according to a schedule of target temperatures selected to correlate with sleep cycles of the user. Such an arrangement promotes deeper, more restful sleep by altering body temperature at critical points.

Preferably, the mattress pad is sized to fit standard mattress sizes. For example, twin (about 97 cm by about 191 cm (about 38 inches by about 75 inches)), twin XL (about 97 cm by about 203 cm (about 38 inches by about 80 inches)), full (about 137 cm by about 191 cm (about 54 inches by about 75 inches)), queen (about 152 cm by about 203 cm (about 60 inches by about 80 inches)), king (about 193 cm by about 203 cm (about 76 inches by about 80 inches), and California king (about 183 cm by about 213 cm (about 72 inches by about 84 inches)). In one embodiment, the mattress pad is about 76 cm by about 203 cm (about 30 inches by about 80 inches). This allows a single user of a full, queen, or king size bed to use the mattress pad without affecting a sleeping partner. In one embodiment, the mattress pad is sized to fit a crib mattress (about 71 cm by about 132 cm (about 28 inches by about 52 inches)). In a preferred embodiment, the single mattress pad (e.g., twin, twin XL, sized to fit a single user of a larger bed, crib) attaches to one control unit and the double mattress pad (e.g., full, queen, king, California king) attaches to two control units.

In an alternative embodiment, the mattress pad contains a conductive fiber to heat one section of the mattress pad and water circulation to cool another section of the mattress pad. In one example, this allows the temperature of the main body or body core region to be lower than the temperature for the feet. The feet play an active role in the regulation of body temperature. The feet have a large surface area and specialized blood vessels, which allow the feet to release heat from the body. If the feet become too cold, excess heat cannot be released from the body and an individual will not be able to sleep.

In one embodiment, the mattress pad is grounded, which provides the human body with electrically conductive contact with the surface of the earth. Grounding is based on the theory that the earth is a source of negatively charged free electrons, and, when in contact with the earth, the body uses these free electrons as antioxidants to neutralize free radicals within the body. Grounding the body during sleep helps normalize cortisol levels, improve sleep, and decrease pain and stress levels. In a preferred embodiment, the mattress pad has a conductive material on at least one exterior surface of the mattress pad. In one embodiment, the mattress pad is attached to a wire that is electrically connected to an electrical outlet ground port. Alternatively, the mattress pad is attached to a wire that is connected to a ground rod.

The mattress pad includes at least two layers of a waterproof material that are laminated, affixed to each other, adhered to each other, attached to each other, secured to each other, or welded together to prevent separation or delamination of the layers. In a preferred embodiment, the waterproof material is a urethane or a mixture of urethane and ethylene-vinyl acetate (EVA). A first layer of the waterproof material is permanently affixed to a second layer of the waterproof material. The first layer of the waterproof material has an exterior surface and an interior surface. The second layer of the waterproof material has an exterior surface and an interior surface. In a preferred embodiment, the first layer of the waterproof material is welded (e.g., using high frequency/radio frequency (RF) welding or heat welding) to the second layer of the waterproof material along a continuous perimeter, creating at least one interior chamber constructed and configured to retain fluid without leaking between the interior surface of the first layer of the waterproof material and the interior surface of the second layer of the waterproof material. Fluid is delivered to the at least one interior chamber via a fluid supply line that enters the continuous perimeter via an opening sized to sealingly receive the fluid supply line. Fluid is removed from the at least one interior chamber via a fluid return line that exits the continuous perimeter via an opening sized to sealingly receive the fluid return line.

In a preferred embodiment, the waterproof material is covered on the exterior surfaces with an interlock or knit fabric. The interlock or knit fabric on the exterior surface of the mattress pad preferably contains a copper or a silver ion thread for antimicrobial protection. Alternatively, the interlock or knit fabric on the exterior surface of the mattress pad is treated with an antibacterial or an antimicrobial agent (e.g., Microban®). In one embodiment, the waterproof material is covered on the exterior surface with a moisture wicking material.

In one embodiment, the mattress pad includes a spacer layer positioned within the interior chamber between the interior surface of the first layer of the waterproof material and the interior surface of the second layer of the waterproof material. The spacer layer provides separation between the first layer of the waterproof material and the second layer of the waterproof material, ensuring that the fluid flows through the mattress pad when a body is on the mattress pad. The spacer layer advantageously provides structural support to maintain partial channels through the interior chamber or fluid passageways, which are important to ensure constant and consistent fluid flow through the interior chamber with heavy users on firm mattresses. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

FIG. 9A illustrates a cross-section of a mattress pad with two layers of waterproof material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

FIG. 9B illustrates a cross-section of a mattress pad with two layers of waterproof material and two layers of a second material. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

FIG. 9C illustrates a cross-section of a mattress pad with two layers of waterproof material and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding).

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties. In another embodiment, the spacer layer 610 is in a honeycomb shape.

FIG. 9D illustrates a cross-section of a mattress pad with two layers of waterproof material, two layers of a second material, and a spacer layer. In this embodiment, a first layer of a waterproof material 602 and a second layer of a waterproof material 604 are affixed or adhered together to form an interior chamber 600. The interior chamber 600 is constructed and configured to retain fluid without leaking. In a preferred embodiment, the first layer of the waterproof material 602 and the second layer of the waterproof material 604 are welded together (e.g., using high frequency/radio frequency (RF) welding or heat welding). A first layer of a second material 606 is on an exterior surface of the first layer of the waterproof material 602. A second layer of the second material 608 is on an exterior surface of the second layer of the waterproof material 604. In a preferred embodiment, the second material is a knit or interlock material. Alternatively, the second material is a woven or non-woven material. In yet another embodiment, the second material is formed of plastic.

A spacer layer 610 is positioned within the interior chamber 600 between an interior surface of the first layer of the waterproof material 602 and an interior facing of the second layer of the waterproof material 604. The spacer layer 610 is configured to provide structural support to maintain partial channels for fluid flow through the interior chamber. In one embodiment, the fluid flows through the spacer layer. In a preferred embodiment, the spacer layer is laminated, affixed, adhered, attached, secured, or welded to the first layer of the waterproof material and/or the second layer of the waterproof material. The spacer layer is preferably made of a foam mesh or a spacer fabric. In one embodiment, the spacer layer has antimicrobial properties.

As previously described, the mattress pad includes two layers of a waterproof material and at least one additional layer of a second material in one embodiment. Although FIGS. 9B and 9D illustrate a first layer of the second material 606 and a second layer of the second material 608, in one embodiment, the first layer of the second material 606 is present without the second layer of the second material 608. Alternatively, the second layer of the second material 608 is present without the first layer of the second material 606.

In another embodiment, the mattress pad includes at least one layer of a thermally reflective and/or an insulating material (e.g., lyocell, such as TENCEL). In one embodiment, the first layer of the second material 606 and/or the second layer of the second material 608 is a thermally reflective and/or the insulating material. In another embodiment, the thermally reflective and/or the insulating material is positioned between the second layer of the waterproof material 604 and the second layer of the second material 608. In yet another embodiment, the thermally reflective and/or the insulating material is positioned between the first layer of the waterproof material 602 and the first layer of the second material 606.

In one embodiment, the mattress pad absorbs heat from the mattress. Advantageously, providing the thermally reflective and/or the insulating material between the waterproof layer of the mattress pad and the mattress reduces the thermal demand on the cooling unit without impacting the rate of heat transfer from the occupant.

Figure 10:
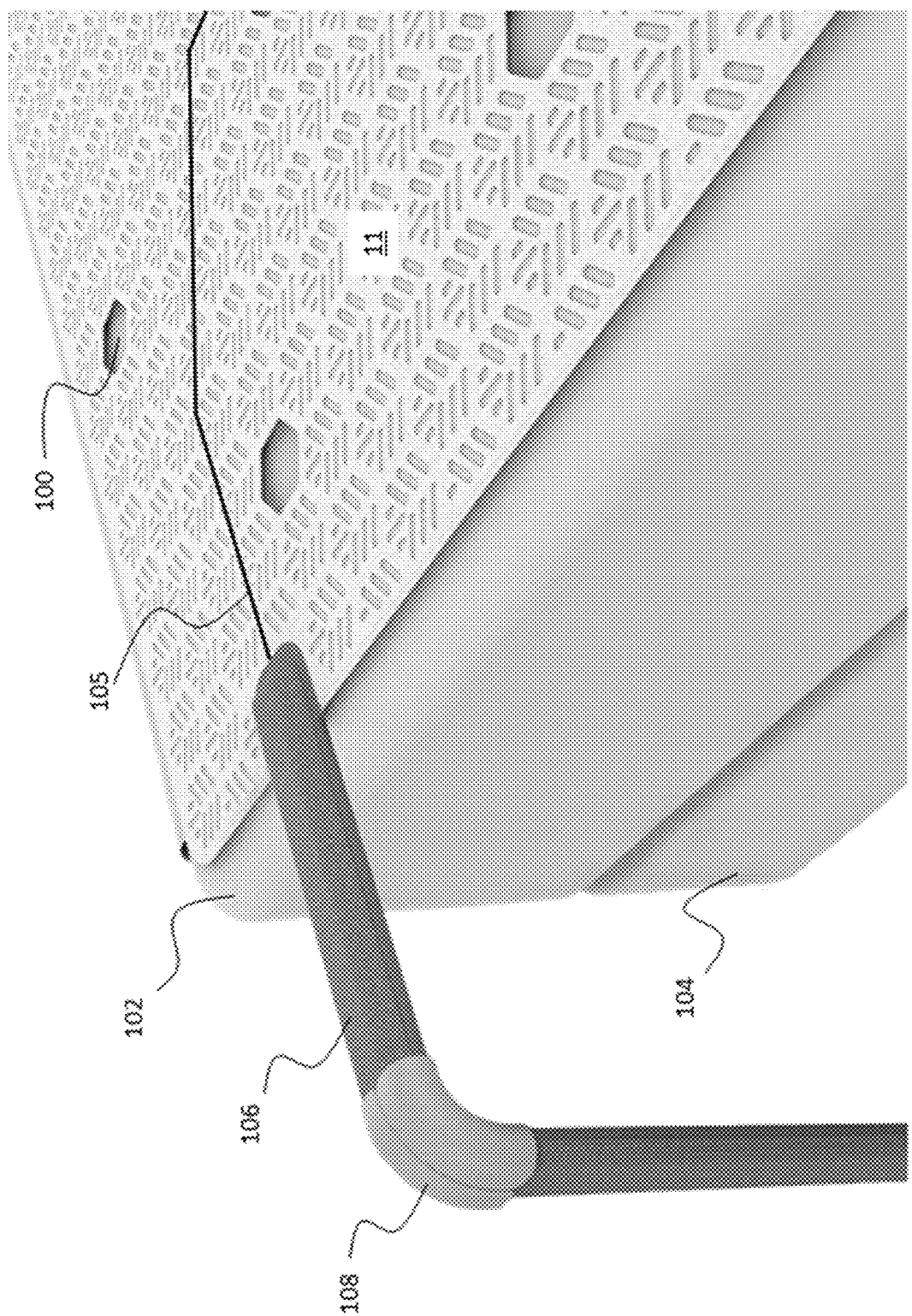
FIG. 10 is a view of a mattress pad hose elbow according to one embodiment.

FIG. 10 is a view of a mattress pad hose elbow according to a preferred embodiment. The mattress pad 11 is placed on top of a mattress 102 and box springs or foundation 104. The mattress pad 11 connects to the control unit (not shown) via a flexible hose 106 containing the flexible supply and return lines. The flexible hose is preferably formed from a polyurethane. Alternatively, the flexible hose is formed from extruded silicone double wall tubing. In one embodiment, the flexible hose has a polyethylene foam or other insulating cover. Additionally or alternatively, the flexible hose is covered with a fabric (e.g., nylon, polyester, rayon).

A mattress pad hose elbow 108 is concentric around the flexible hose 106. The mattress pad hose elbow 108 secures the flexible hose 106 to the side of the mattress 102 and box springs or foundation 104, which provides structural support to the flexible hose 106. The mattress pad hose elbow 108 is sized to fit tightly around the flexible hose 106. In a preferred embodiment, the mattress pad hose elbow 108 is formed with silicone or rubber. Alternatively, the mattress pad hose elbow 108 is formed from plastic (e.g., ethylene-vinyl acetate (EVA) foam, polyethylene foam). In a preferred embodiment, the mattress pad hose elbow 108 is operable to slide on the flexible hose 106. In one embodiment, the mattress pad hose elbow 108 is adjustable.

The mattress pad 11 preferably contains a plurality of holes or openings 100 in the surface of the mattress pad 11. The plurality of holes or openings 100 direct the movement of the fluid in the pad. In a preferred embodiment, the plurality of holes or openings 100 is in a pre-selected pattern to help manufacturing efficiency. Alternatively, the plurality of holes or openings 100 is in a random pattern. The plurality of holes or openings 100 is shown in a hexagon shape in FIG. 10. Alternatively, the shape of each of the plurality of holes or openings 100 is in the shape of a triangle, a circle, a rectangle, a square, an oval, a diamond, a pentagon, a heptagon, an octagon, a nonagon, a decagon, a trapezium, a parallelogram, a rhombus, a cross, a semicircle, a crescent, a heart, a star, a snowflake, or any other polygon. In one embodiment, the voids created by the plurality of holes or openings 100 include at least 80% of the surface area of the mattress pad. In other embodiments, the voids created by the plurality of holes or openings 100 include at least 5%, at least 10%, at least 15%, at least 20%, at least 25%, at least 30%, at least 40%, at least 50%, at least 60%, at least 70%, at least 75%, at least 85%, at least 90%, or at least 95% of the surface area of the mattress pad.

The spacing and number of the plurality of holes or openings 100 are varied to adjust the thermal properties of the mattress pad. For example, in one embodiment, the density of the holes or openings is higher near the torso region than in the head and leg regions, for providing more exposure to the torso region of the user for managing body temperature in that region, and less exposure to the extremities of the user. In one embodiment, the spacing between each of the plurality of holes or openings is at least 5 mm (0.2 inches).

Alternatively, the mattress pad includes a first layer having a plurality of shapes and a second layer having a corresponding plurality of shapes. The second layer is permanently affixed to the first layer along a periphery of the article and a periphery of each of the shapes. This embodiment differs from the one shown including the plurality of holes and openings in that the first layer and the second layer do not contain holes. However, this embodiment is functionally equivalent to the one with the plurality of holes and openings because the fluid does not travel through the shapes.

In a preferred embodiment, the mattress pad 11 contains at least one weld line 105 to help manage the flow of the fluid in the interior chamber. The at least one weld line 105 preferably directs the fluid flow through the pad from head to foot, and returns the fluid to the control unit via the return line. The at least one weld line 105 allows the fluid to flow across all areas of the mattress pad 11 to provide a substantially uniform temperature within the pad. In one embodiment, the at least one weld line is formed from the permanent attachment of the first layer of the waterproof material and the second layer of the waterproof layer along the periphery of the plurality of holes or openings.

Figure 11:
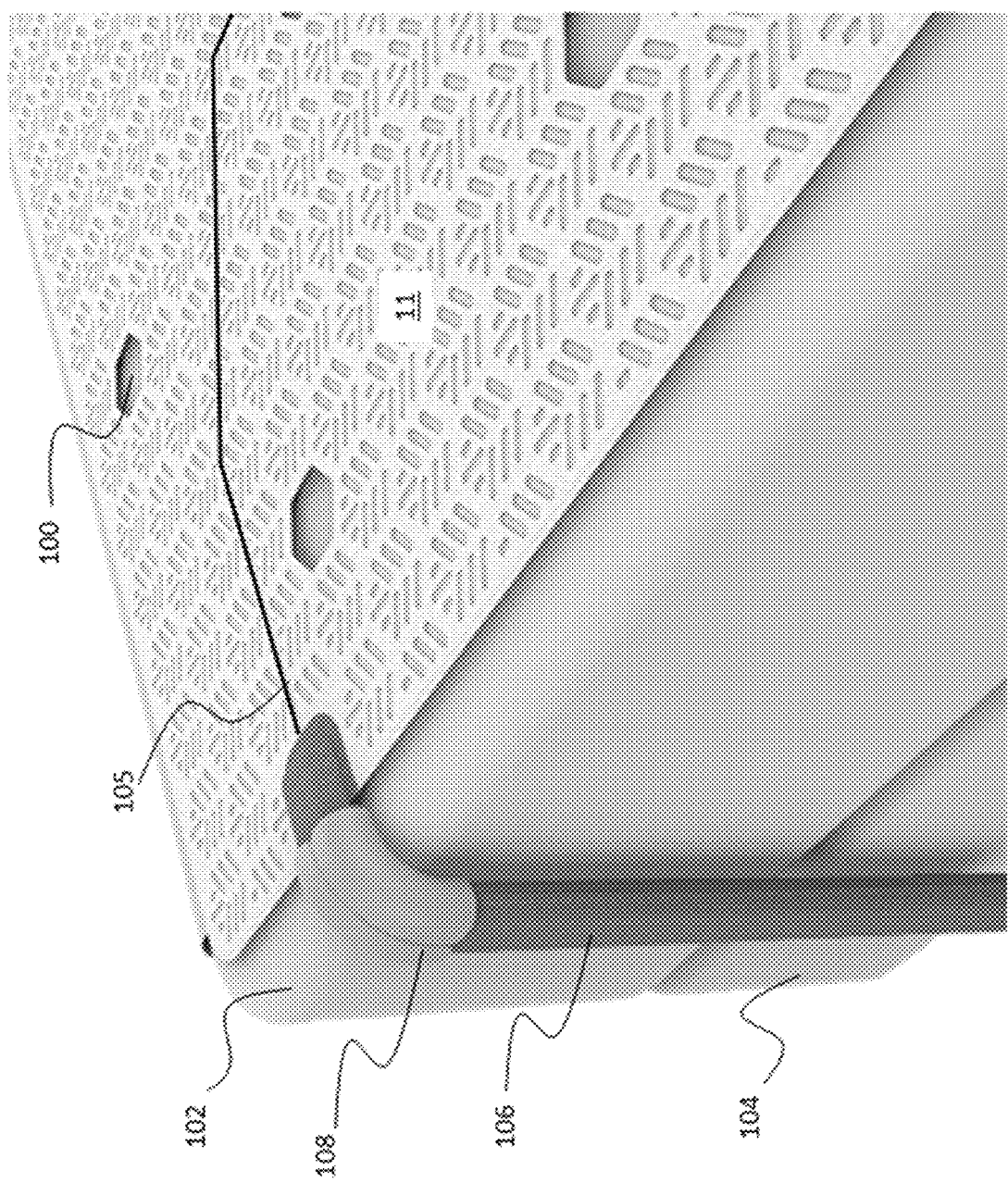
FIG. 11 is another view of the mattress pad hose elbow of FIG. 10.

FIG. 11 is another view of the mattress pad hose elbow of FIG. 10. The flexible hose 106 is positioned next to the mattress 102 and the box springs or foundation 104 using the mattress pad hose elbow 108. Advantageously, the mattress pad hose elbow 108 secures the flexible hose 106 to the side of the mattress 102 and box springs or foundation 104, providing structural support for the flexible hose 106. Further, the total height of a mattress, box springs or foundation, and/or a bed frame is not uniform. The mattress pad hose elbow 108 provides customization for the height of the mattress, the box springs or foundation, and/or the bed frame.

In another embodiment, the flexible hose is positioned next to the mattress using hook and loop tape. In yet another embodiment, the flexible hose is positioned next to the mattress using elastic. In still another embodiment, the flexible hose is positioned next to the mattress using at least one snap. Alternatively, the flexible hose is positioned next to the mattress using at least one buckle.

Figure 12:
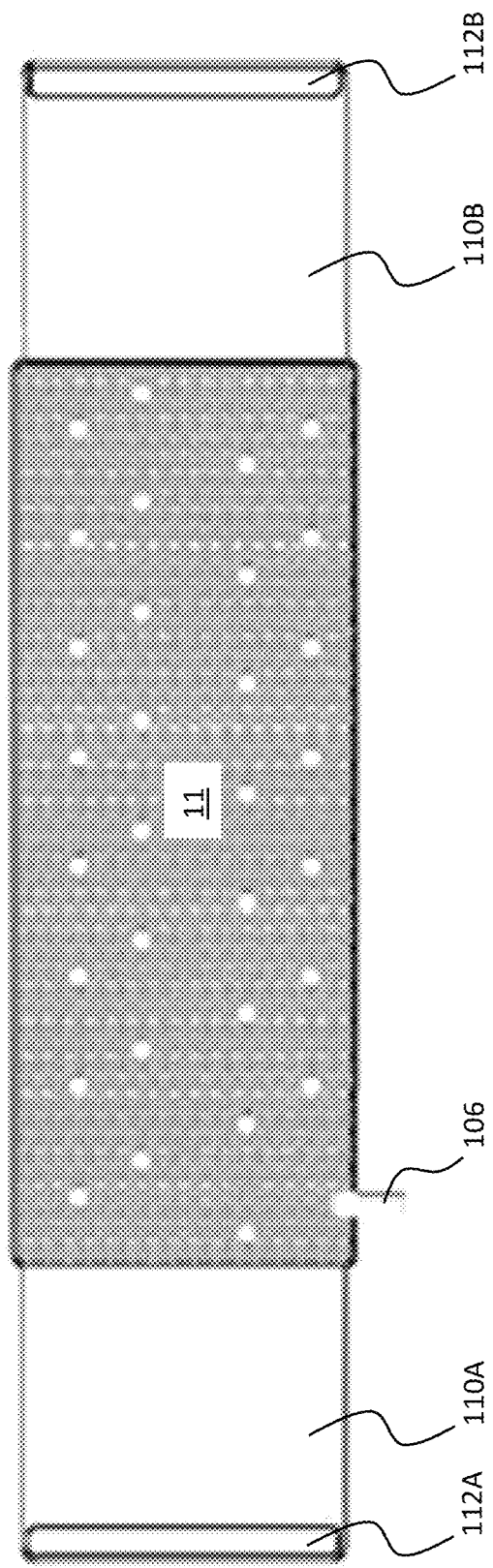
FIG. 12 is an exploded view of a single mattress pad.

FIG. 12 is a top perspective view of a single mattress pad. A top panel 110A is attached (e.g., sewn, adhered, welded) to the top of the mattress pad 11 at an attachment point 114A. A bottom panel 110B is attached (e.g., sewn, adhered, welded) to the bottom of the mattress pad 11 at an attachment point 114B. A non-slip piece 112A is attached (e.g., sewn, adhered, welded) to the top panel 110A on a side opposite the attachment point 114A. A non-slip piece 112B is attached (e.g., sewn, adhered, welded) to the bottom panel 110B on a side opposite the attachment point 114B. Preferably, the top panel 110A and the bottom panel 110B are formed from the same material as the second material (e.g., a knit or interlock fabric) on the exterior surface of the mattress pad. In a preferred embodiment, the non-slip pieces 112A, 112B are formed from foam. Alternatively, the non-slip pieces 112A, 112B are formed from latex, silicon, or rubber. The non-slip pieces 112A, 112B are preferably moisture wicking and/or antimicrobial. In one embodiment, the non-slip pieces 112A, 112B are printed onto the top panel 110A and the bottom panel 110B. In one embodiment, the top panel 110A and the bottom panel 110B are between about 18 cm (about 7 inches) and about 76 cm (about 30 inches) in length. In a preferred embodiment, top panel 110A and the bottom panel 110B are about 66 cm (about 26 inches) in length.

In another embodiment, the top panel 110A and the bottom panel 110B act as a non-slip surface. In one embodiment, the top panel 110A and the bottom panel 110B are made of gripper or anti-slip fabric. In this embodiment, the non-slip pieces 112A and 112B are not needed because the top panel 110A and the bottom panel 110B act as the non-slip surface.

The single mattress pad is preferably reversible, such that the mattress pad is operable when either exposed surface is facing upward. Advantageously, this allows the flexible hose to exit on either the left or the right side of the bed. This reversibility eliminates the need to manufacture single mattress pads with a "left" configuration or a "right" configuration for single users of a full, queen, or king size bed and/or single users where a bed is positioned such that a particular configuration is required (e.g., a bed positioned against a wall).

Figure 13:
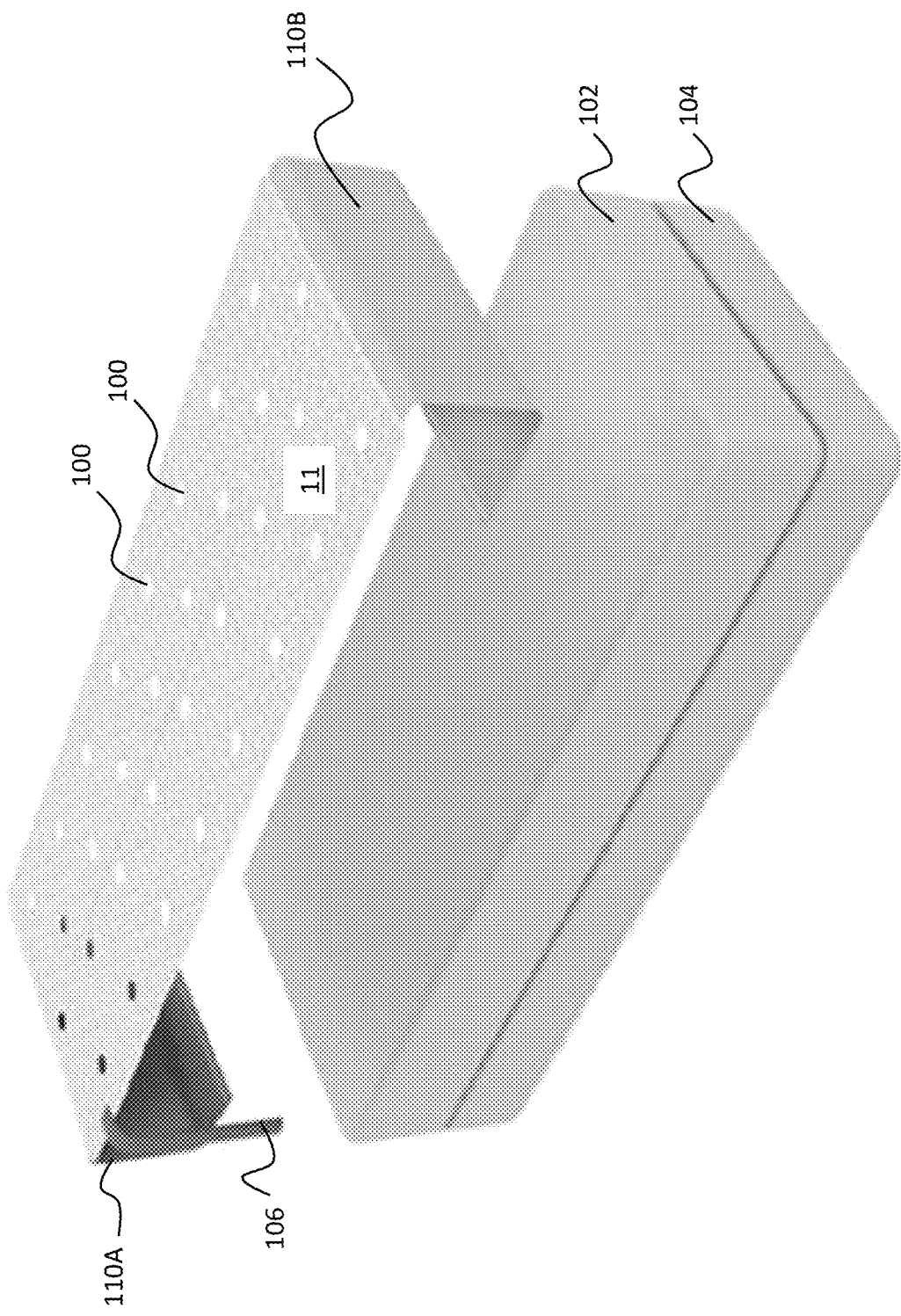
FIG. 13 is a top perspective view of a single mattress pad.

FIG. 13 is an exploded view of a single mattress pad. The mattress pad 11 is shown above the mattress 102 and the box springs or foundation 104. While in use, the mattress pad 11 is placed on top of the mattress 102. The ends of the mattress pad 11 are attached to panels 110A, 110B. Panels 110A, 110B are placed over the head and foot ends of the mattress 102, with the ends of the panels 110A, 110B sandwiched between the mattress 102 and box springs or foundation 104.

As previously described, the mattress pad 11 preferably contains a plurality of holes or openings 100 in the surface of the mattress pad 11. A first layer having a plurality of holes or openings is permanently affixed to a second layer having a plurality of holes or openings along a periphery of the mattress pad and a periphery of each of the plurality of holes or openings. At least one interior chamber is defined between an interior surface of the first layer and an interior surface of the second layer. The at least one interior chamber is constructed and configured to retain a fluid without leaking. The interior surface of the first layer and the interior surface of the second layer are made of at least one layer of a waterproof material.

In an alternative embodiment, the mattress pad does not contain a plurality of holes or openings in the surface in the mattress pad. A first layer is permanently affixed to a second layer along a periphery of the mattress pad. In one embodiment, the waterproof material is stretchable. In a preferred embodiment, the stretch rate of the waterproof material is equal to or greater than the stretch rate of surrounding materials (e.g., a mattress). Advantageously, this prevents the mattress pad from gathering and bunching underneath a user.

Figure 14:
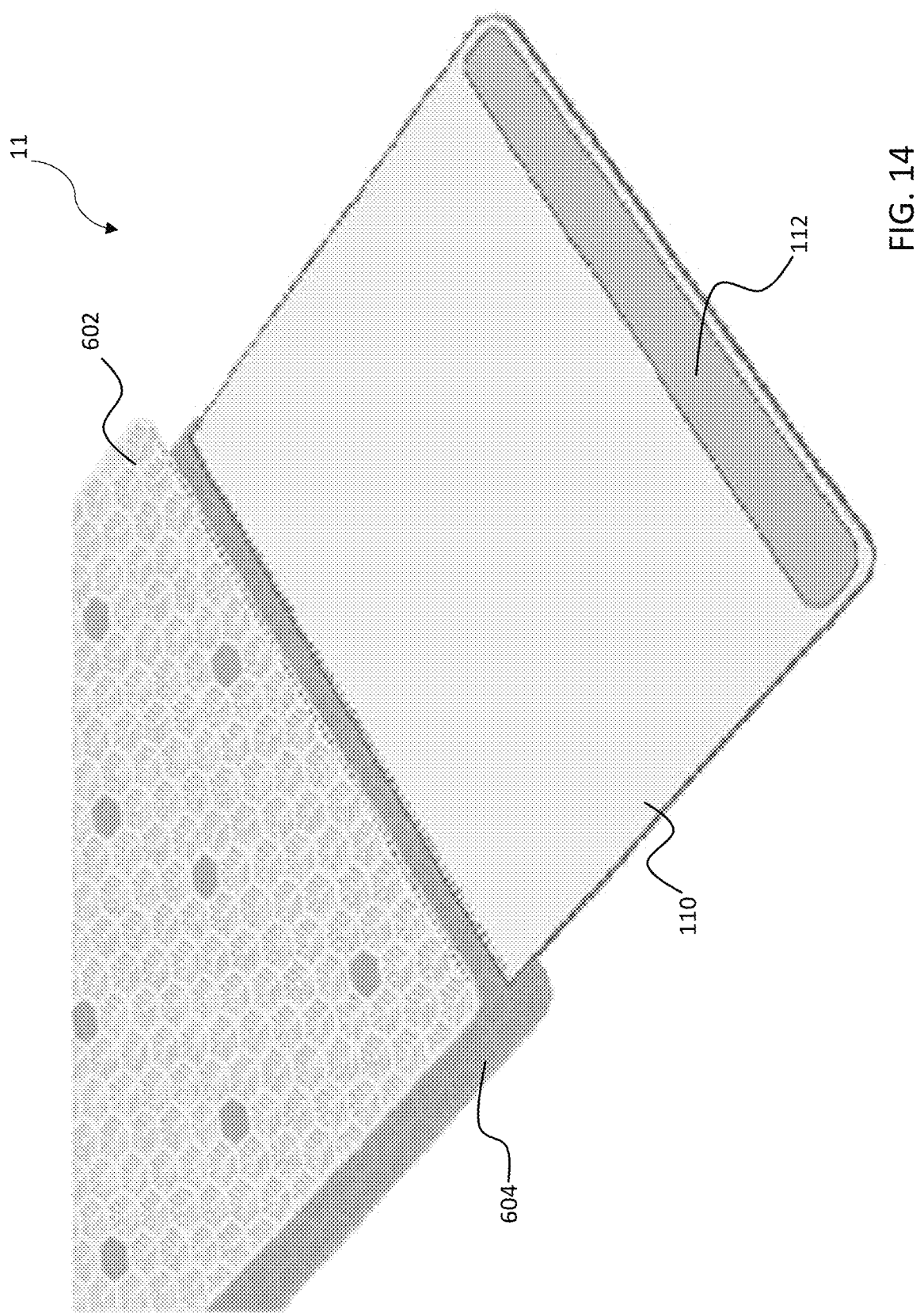
FIG. 14 is a top perspective view of an end of a single mattress pad.

FIG. 14 is an exploded view of an end of a single mattress pad. The mattress pad 11 is formed of at least two layers of waterproof material as shown in FIGS. 9A-9D. In one embodiment, the panel 110 is permanently affixed (e.g., sewn, adhered, welded) between a first layer of a waterproof material 602 and a second layer of a waterproof material 604. On the opposite end from where the panel 110 is attached to the mattress pad 11, a non-slip piece 112 is permanently affixed (e.g., sewn, adhered, welded) to the panel. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

Figure 15:
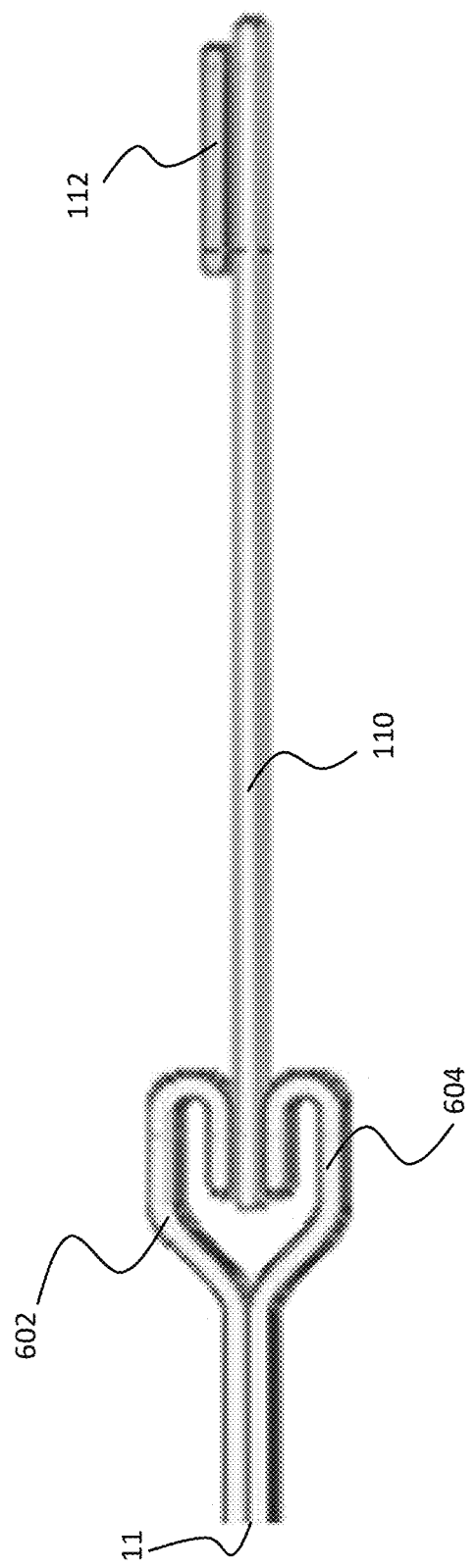
FIG. 15 is a side perspective view of an end of a single mattress pad.

FIG. 15 is a side perspective view of an end of a single mattress pad. The mattress pad 11 has a first layer of waterproof material 602 and a second layer of waterproof material 604. A first end of panel 110 is attached to the first layer of waterproof material 602 and the second layer of waterproof material 604. The panel 110 is permanently affixed (e.g., sewn, adhered, welded) between the first layer of waterproof material 602 and the second layer of waterproof material 604. In a preferred embodiment, the external surface of the first layer of waterproof material 602 and the second layer of waterproof material 604 are folded over to attach to the first end of panel 110. A non-slip piece 112 is permanently affixed (e.g., sewn, adhered, welded) to the end opposite of the first end of panel 110. In a preferred embodiment, the non-slip piece 112 is formed from foam. Alternatively, the non-slip pieces 112 are formed from latex, silicon, or rubber. The non-slip pieces 112 are preferably moisture wicking and/or antimicrobial.

In alternative embodiments, the mattress pad includes interlock or knit fabric on exterior surfaces of the mattress pad. In other embodiments, the exterior surfaces of the mattress pad are covered with a woven fabric, a non-woven fabric, or a polymer film (e.g., urethane or thermoplastic polyurethane (TPU)). Additionally or alternatively, the mattress pad includes a spacer layer between an interior surface of the first layer of waterproof material 602 and an interior surface of the second layer of waterproof material 604.

Figure 16:
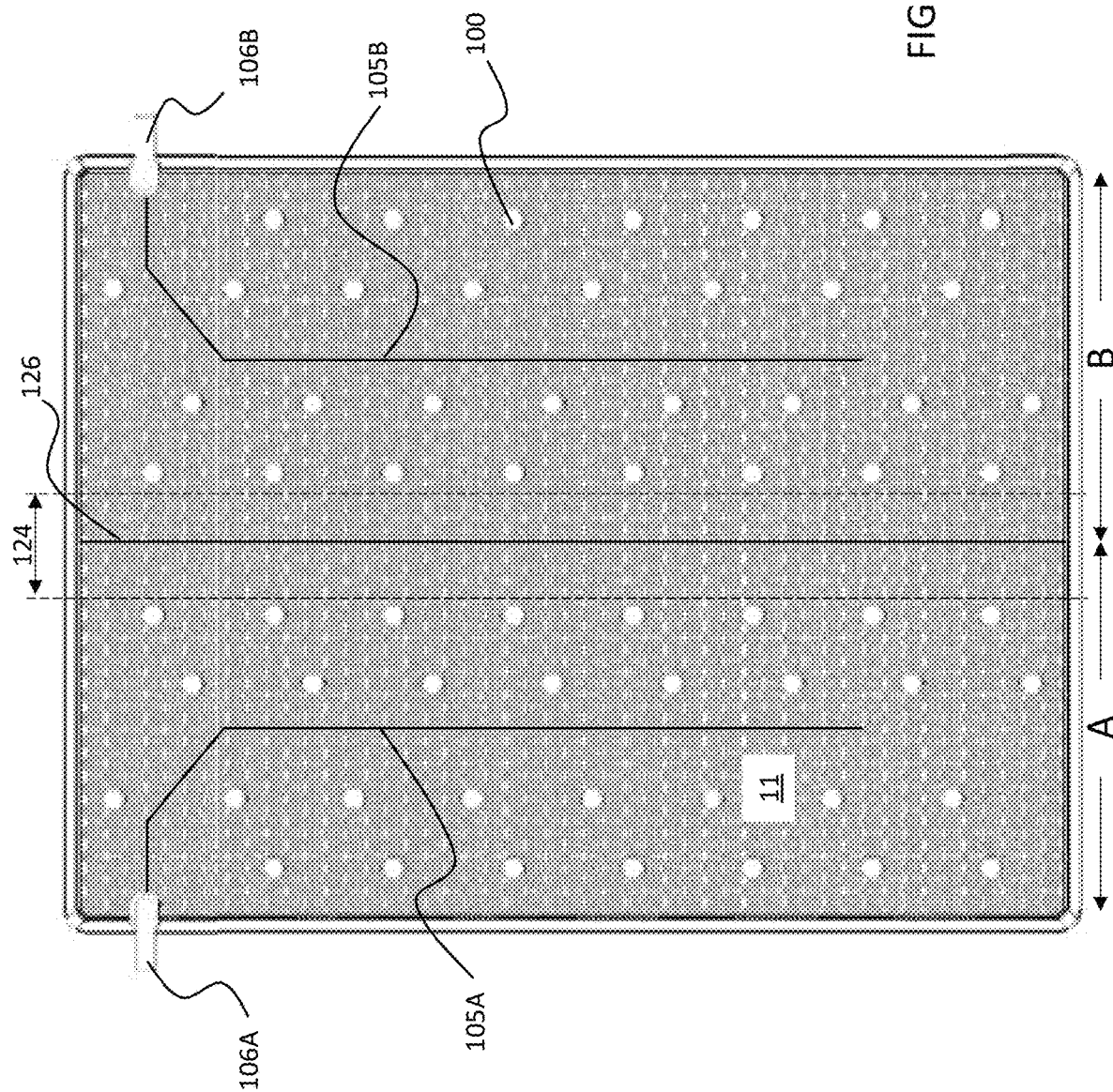
FIG. 16 is a top perspective view of a double mattress pad.

FIG. 16 is a top perspective view of a double mattress pad. The mattress pad 11 has two independent thermally regulated surface zones "A" and "B". The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). In a preferred embodiment, the center of the mattress pad 11 contains an area free of holes or openings 124. The area free of holes or openings 124 contains a welded separator 126, which provides a boundary between the two independent thermally regulated surface zones "A" and "B".

Figure 17:
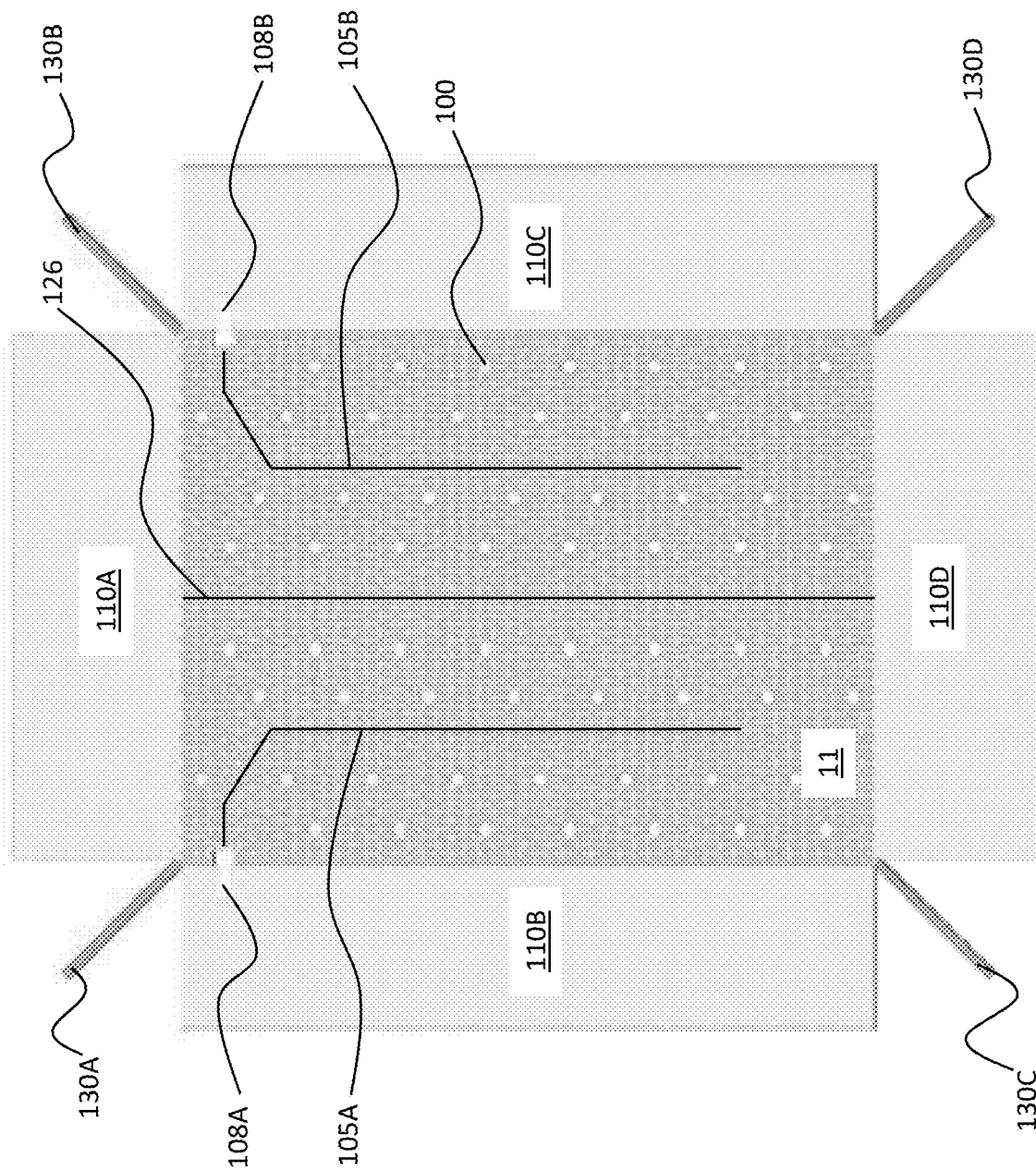
FIG. 17 is an exploded view of a double mattress pad.

FIG. 17 is another top perspective view of a double mattress pad. The mattress pad 11 has a top end panel 110A, a left side panel 110B, a right side panel 110C, and a bottom end panel 110D. The top end panel 110A, the left side panel 110B, the right side panel 110C, and the bottom end panel 110D are preferably formed from a material with stretch (e.g., interlock or knit). In a preferred embodiment, each corner of the mattress pad 11 contains at least one non-slip piece. In one embodiment, a top non-slip piece and a bottom non-slip piece are attached to each corner of the mattress pad 11. In the embodiment shown in FIG. 17, the corner between the top end panel 110A and the left side panel 110B has a non-slip piece 130A, the corner between the top end panel 110A and the right side panel 110C has a non-slip piece 130B, the corner between the left side panel 110B and the bottom end panel 110D has a non-slip piece 130C, and the corner between the right side panel 110C and the bottom end panel 110D has a non-slip piece 130D.

The mattress pad 11 preferably contains at least one weld line or other separation to help manage the flow of fluid in the at least one interior chamber. The at least one weld line 105 directs the fluid flow through the pad from head to foot, and returns the fluid to the control unit via the return line. In FIG. 17, the mattress pad has a first weld line 105A to help manage the flow of fluid in the interior chamber of zone "A" and a second weld line 105B to help manage the flow of fluid in the interior chamber of zone "B". Although only one weld line is shown for each independent temperature zone, it is equally possible to have two or more weld lines for each independent temperature zone.

Figure 18:
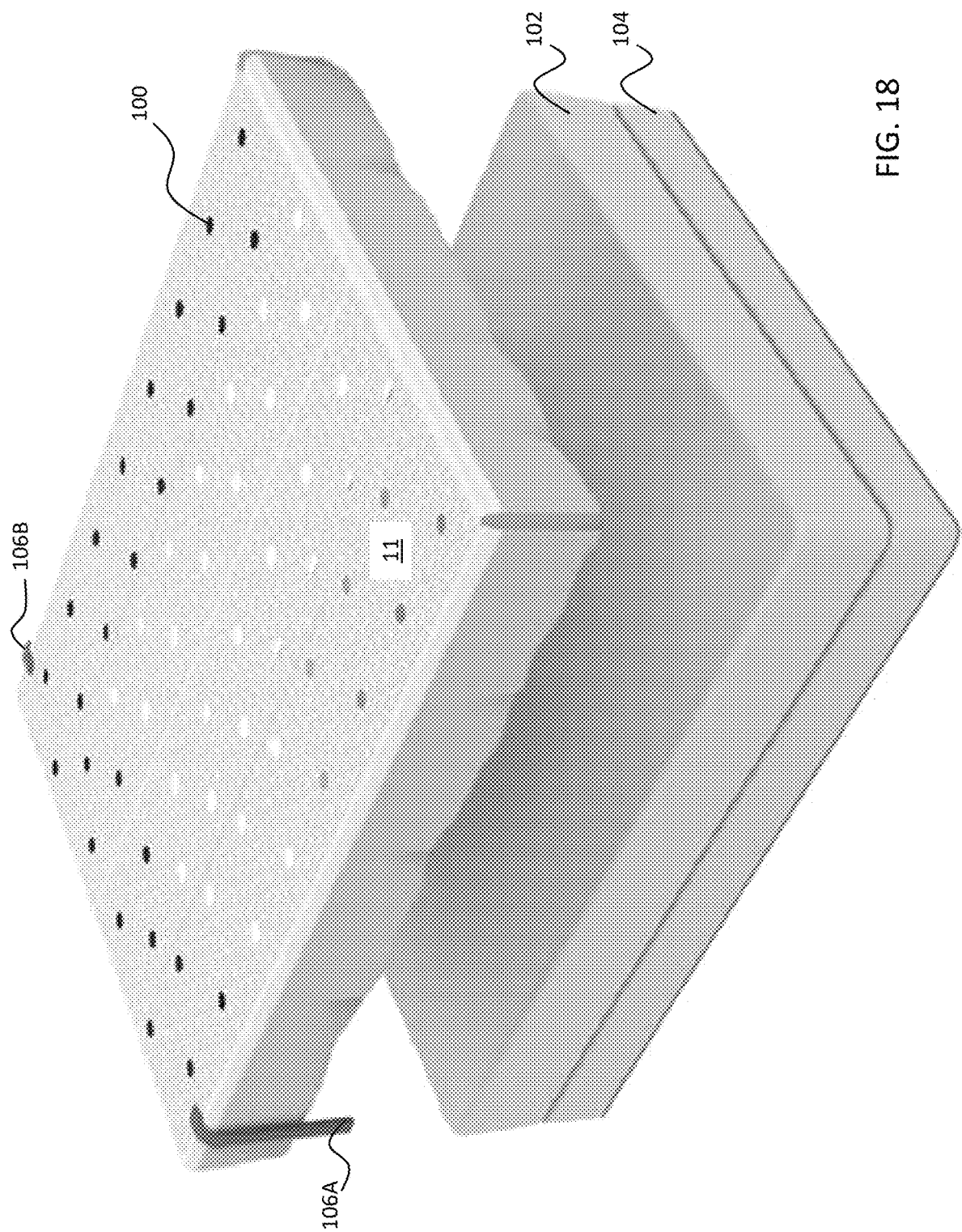
FIG. 18 is another top perspective view of a double mattress pad.

FIG. 18 is an exploded view of a double mattress pad. The mattress pad 11 is shown above the mattress 102 and the box springs or foundation 104. The mattress pad 11 has a first flexible hose 106A and a second flexible hose 106B. In a preferred embodiment, the first flexible hose 106A attaches to a first control unit (not shown) and the second flexible hose 106B attaches to a second control unit (not shown). Alternatively, the first flexible hose 106A and the second flexible hose 106B attach to the same control unit. The surface of the mattress pad 11 contains a plurality of holes or openings 100 in the surface of the mattress pad 11.

Figure 19:
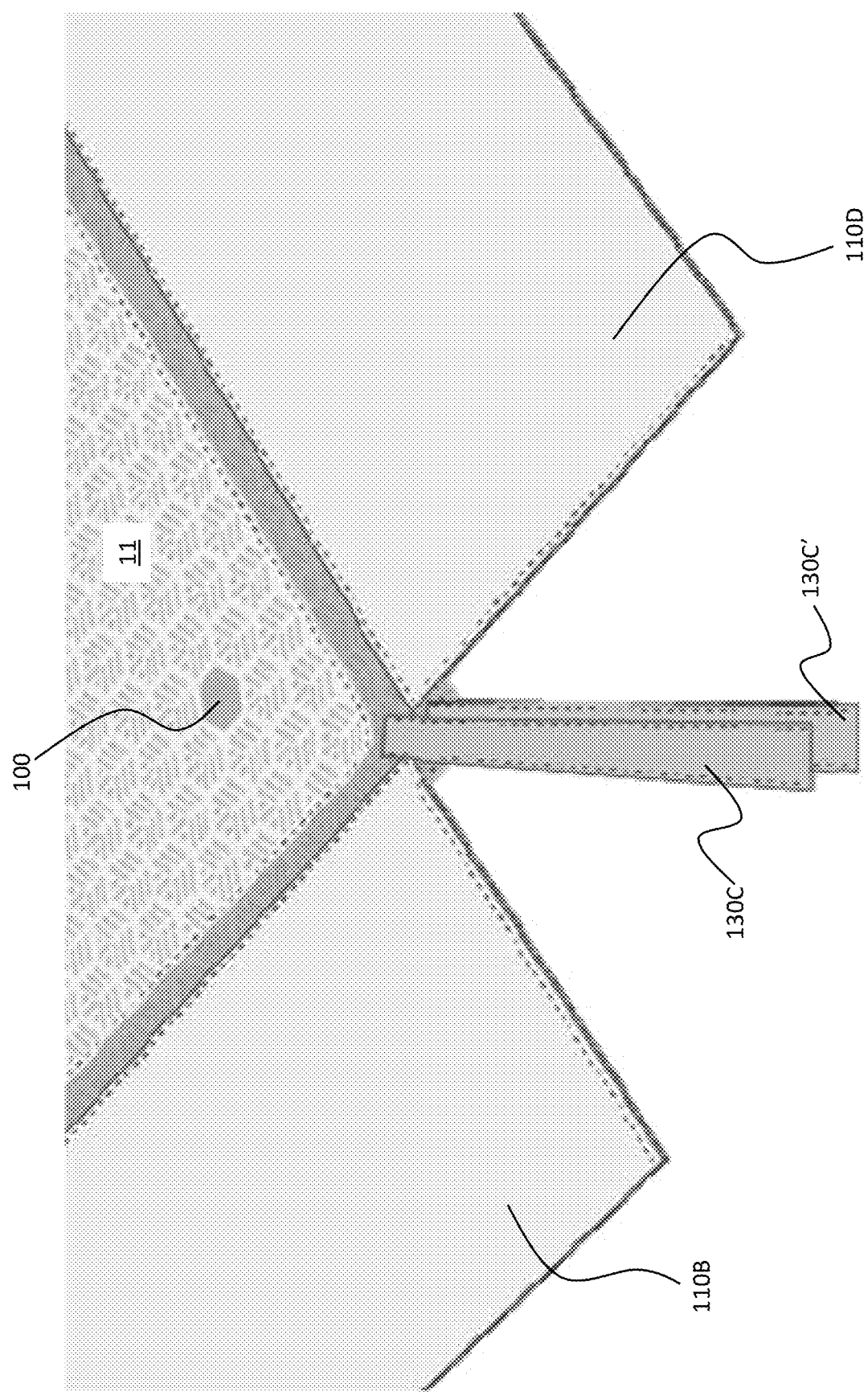
FIG. 19 is a view of the corner of a double mattress pad.

FIG. 19 is an exploded view of the bottom left corner of one embodiment of a double mattress pad before the mattress pad is secured to the bed. In a preferred embodiment, each corner of the mattress pad 11 contains a top non-slip piece 130C and a bottom non-slip piece 130C'. In FIG. 19, the top non-slip piece 130C and the bottom non-slip piece 130C' are shown attached (e.g., sewn, adhered, welded) to the corner formed between the left side panel 110B and the bottom end panel 110D. The left side panel 110B and the bottom end panel 110D are preferably formed from a material with stretch (e.g., interlock or knit). In one embodiment, elastic is attached (e.g., sewn, adhered, welded) to a bottom edge of the left side panel 110B and a bottom edge of the bottom end panel 110D. Alternatively, elastic is encased at the bottom edge of the left side panel 110B and the bottom edge of the bottom end panel 110D.

To secure the mattress pad 11 to the bed, the edge of the left side panel 110B and the edge of the bottom panel 110D are placed on top of the bottom non-slip piece 130C'. The top non-slip piece 130C is then placed on top the left side panel 110B, bottom panel 110D, and the bottom non-slip piece 130C'. The top non-slip piece 130C and bottom non-slip piece 130C' are preferably formed from non-slip foam. Alternatively, the top non-slip piece 130C and bottom non-slip piece 130C' are formed from silicone, rubber, or latex. In one embodiment, the left side panel 110B and the bottom panel 110D are formed from a material with stretch (e.g., interlock or knit). The top non-slip piece 130C and bottom non-slip piece 130C' provide friction to keep the mattress pad in place.

Figure 20:
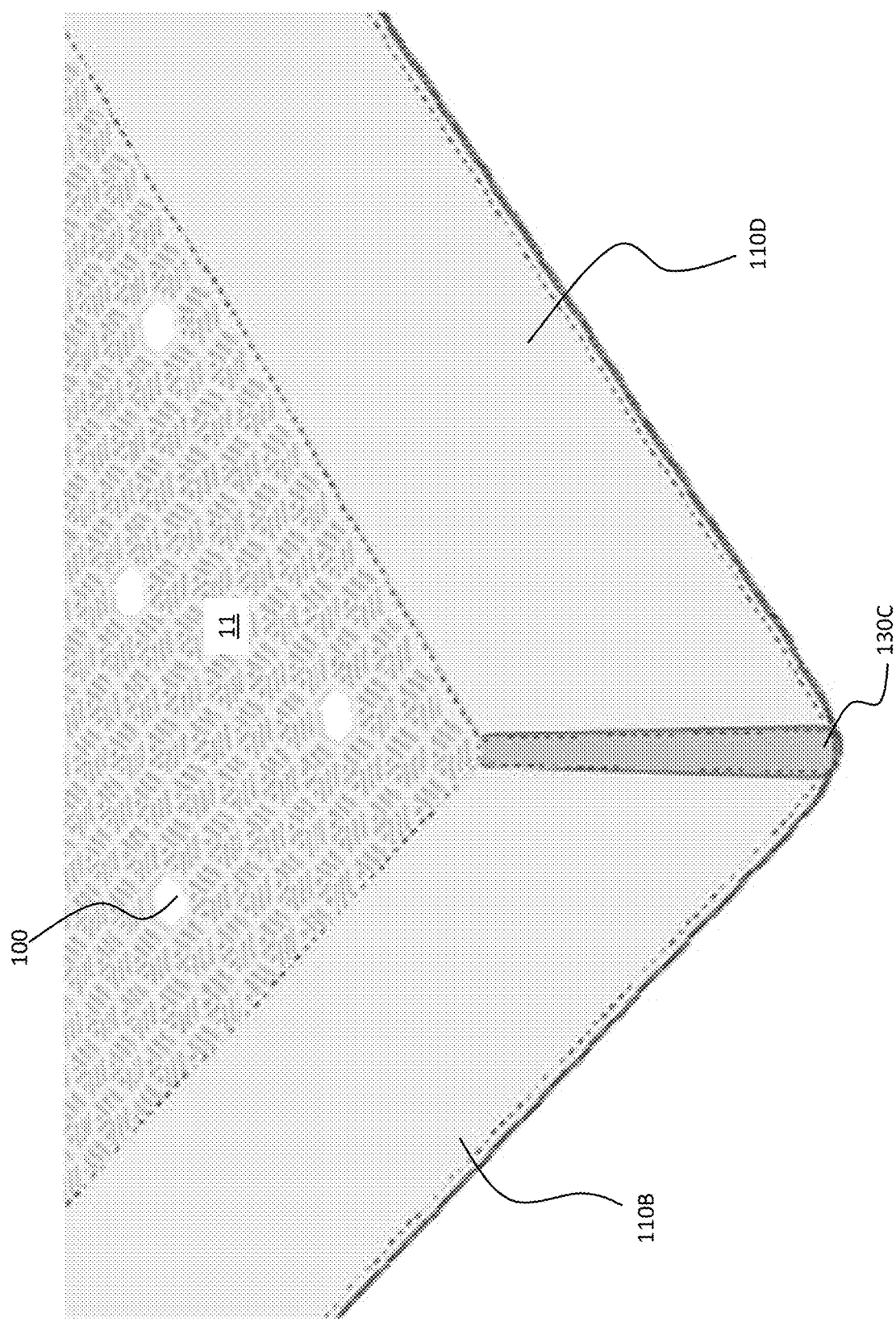
FIG. 20 is another view of the corner of a double mattress pad.

FIG. 20 is a view of the bottom left corner of a double mattress pad after the mattress pad is secured to the bed.

Figure 21:
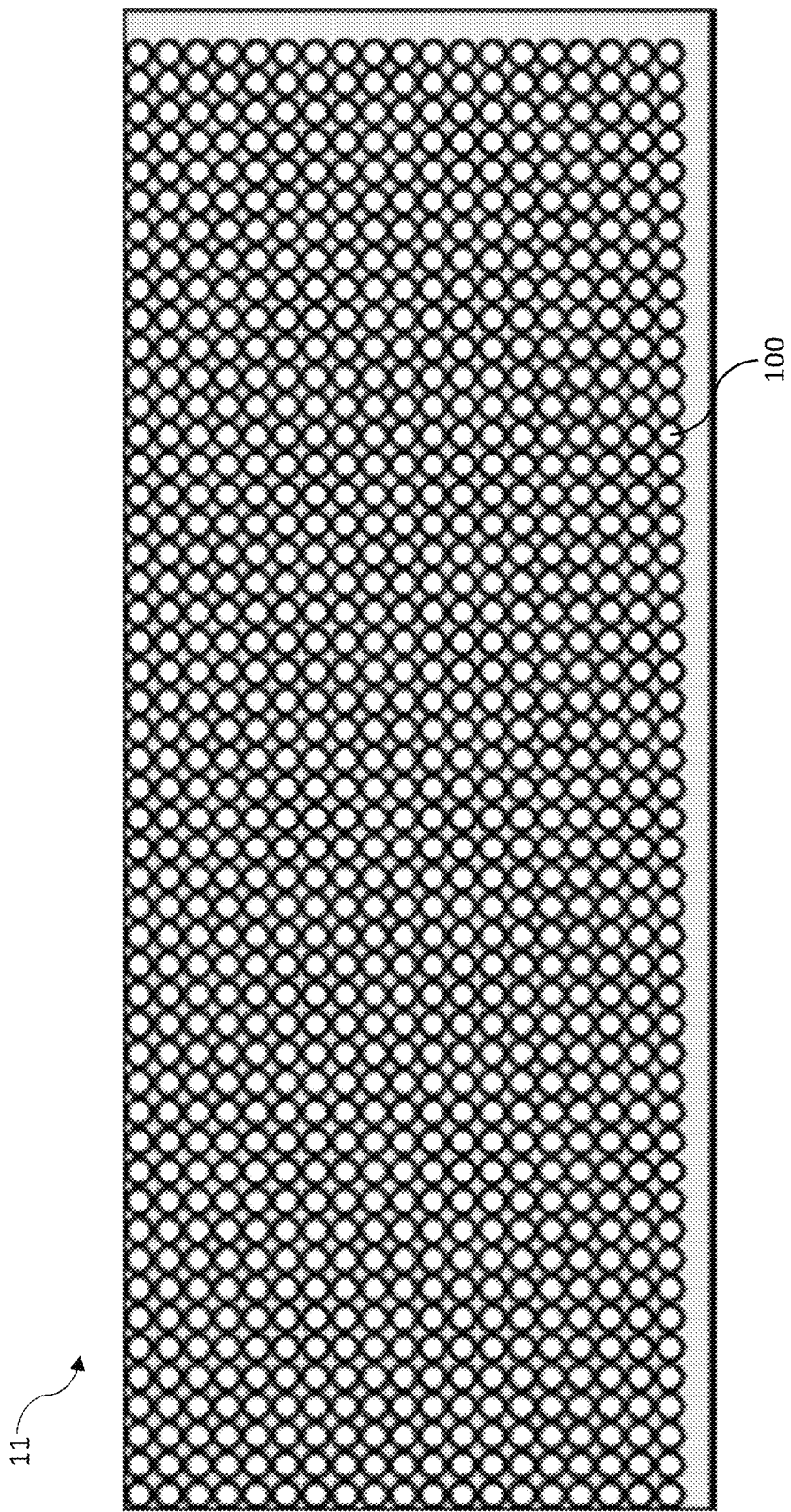
FIG. 21 is a view of another embodiment of a mattress pad.

FIG. 21 is a view of another embodiment of the mattress pad. The plurality of holes or openings 100 is shown in a circle shape in FIG. 21. The voids created by the plurality of holes or openings 100 include at least 80% of the surface area of the mattress pad 11 in this embodiment.

In one embodiment, the control unit is operable to drop a temperature of water from 68° F. to 58° F. in less than 5.3 minutes when in a closed loop (i.e., without the mattress pad attached). In one embodiment, the closed loop consists of 14" long silicone tubing with an outer diameter of ⅜", an inner diameter of ¼", and ⅜" 90° circular plastic connector. The mattress pad preferably has a rate of heat transfer of at least 200 W at a water temperature of 14.4° C. (58° F.). In another embodiment, the mattress pad has a rate of heat transfer of at least 150 W at a water temperature of 14.4° ° C. (58° F.).

Figure 22:
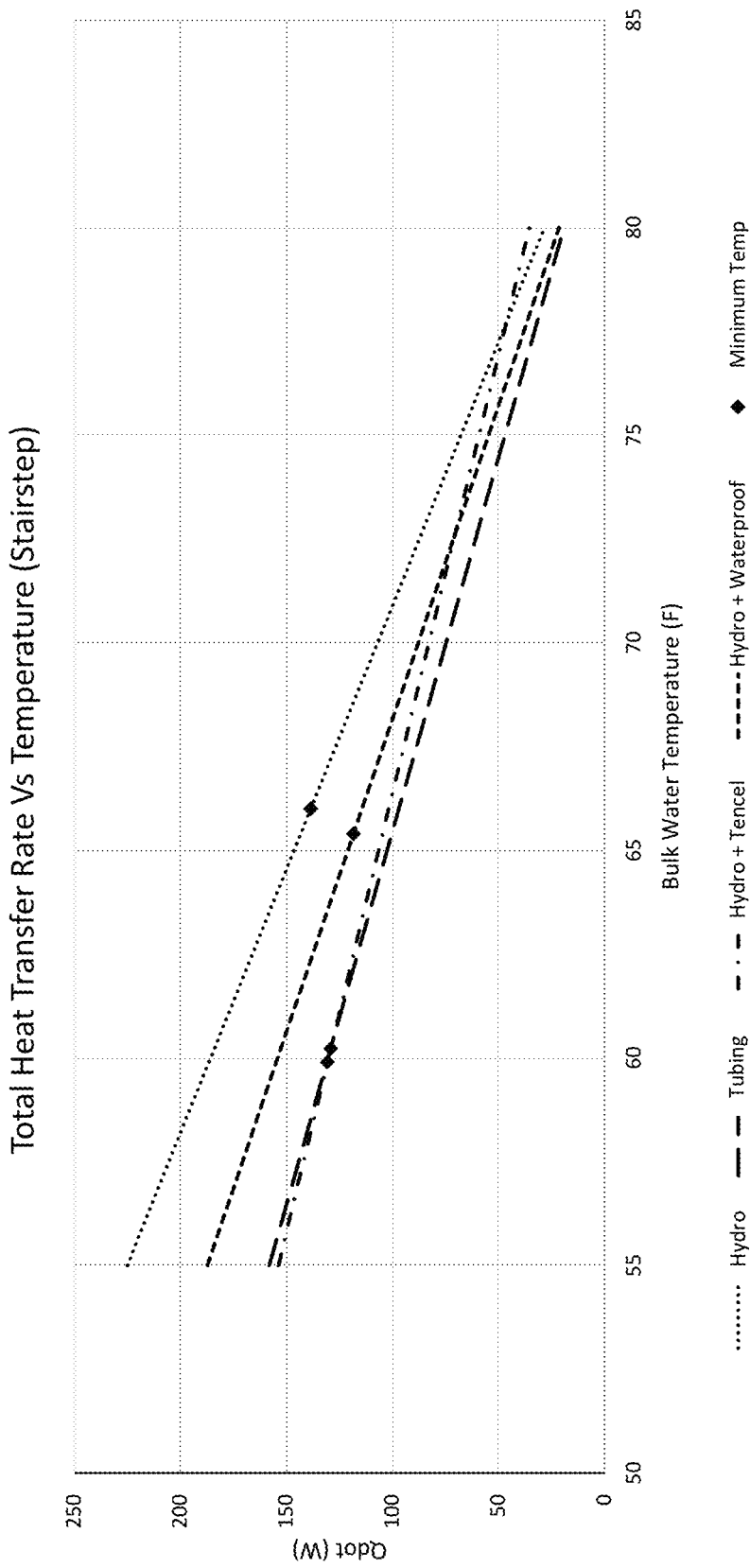
FIG. 22 is a graph of total heat transfer rate vs. bulk water temperature.

FIG. 22 illustrates a total heat transfer rate vs. bulk water temperature for a hydro layer mattress pad without any additional layers of material (e.g., FIG. 9A), a tubing mattress pad (e.g., FIG. 3), a hydro layer mattress pad with a layer of TENCEL between the pad and the mattress (e.g., FIG. 9B), a hydro layer mattress pad with an additional layer of waterproof material, such as polyester with urethane laminate (e.g., FIG. 9B). As is seen in FIG. 22, the layer of TENCEL between the pad and the mattress significantly decreases the heat transfer rate.

Figure 23:
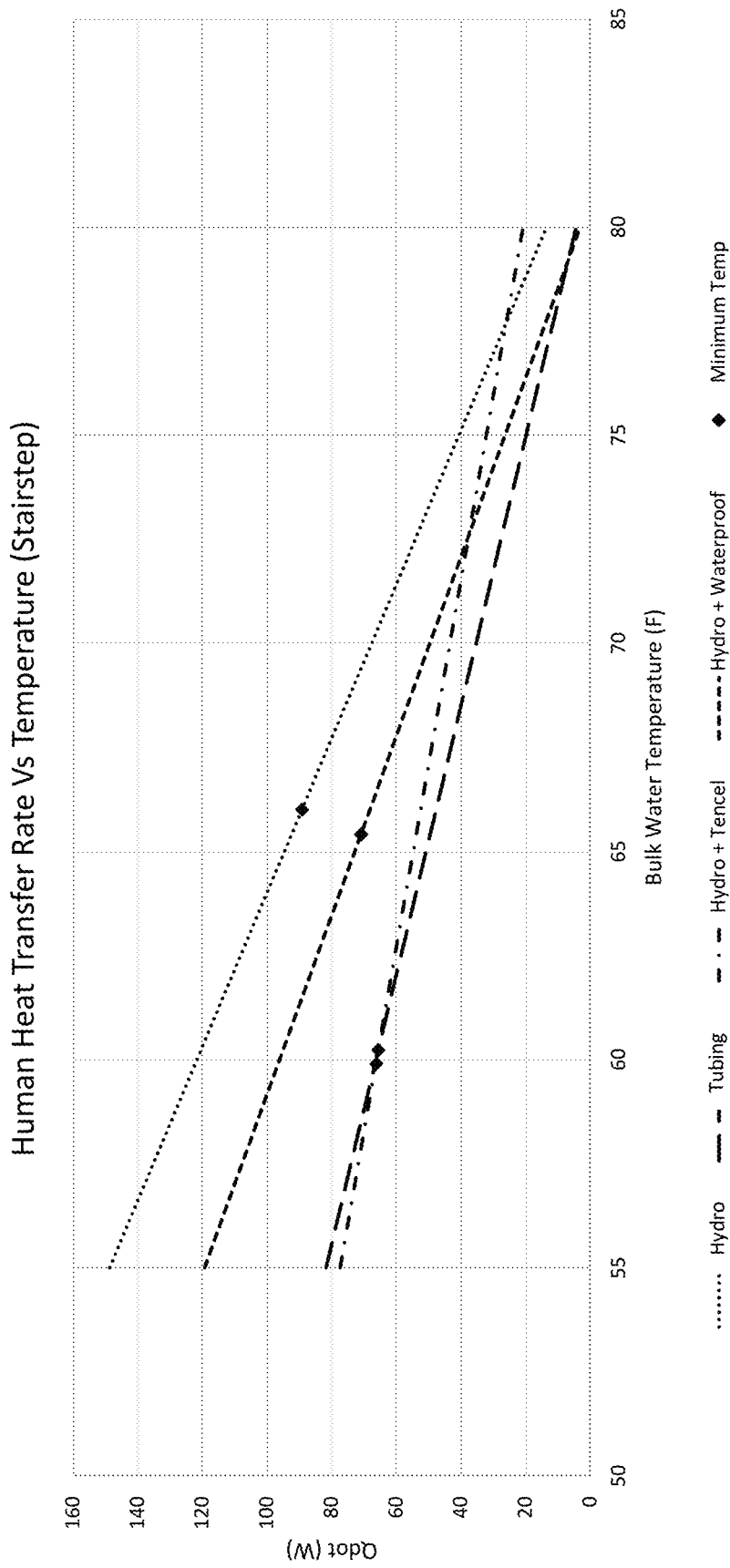
FIG. 23 is a graph of a human heat transfer rate vs. bulk water temperature.

FIG. 23 illustrates a human heat transfer rate vs. bulk water temperature for a hydro layer mattress pad without any additional layers of material (e.g., FIG. 9A), a tubing mattress pad (e.g., FIG. 3), a hydro layer mattress pad with a layer of TENCEL between the pad and the mattress (e.g., FIG. 9B), a hydro layer mattress pad with an additional layer of waterproof material, such as polyester with urethane laminate (e.g., FIG. 9B). As is seen in FIG. 23, the layer of TENCEL between the pad and the mattress reduces the thermal demand without impacting the rate of heat transfer from the user.

In an alternative embodiment, the mattress pad includes tubing (e.g., FIG. 3) with a layer of insulating fabric (e.g., TENCEL) positioned between the tubing and the mattress.

Figure 24:
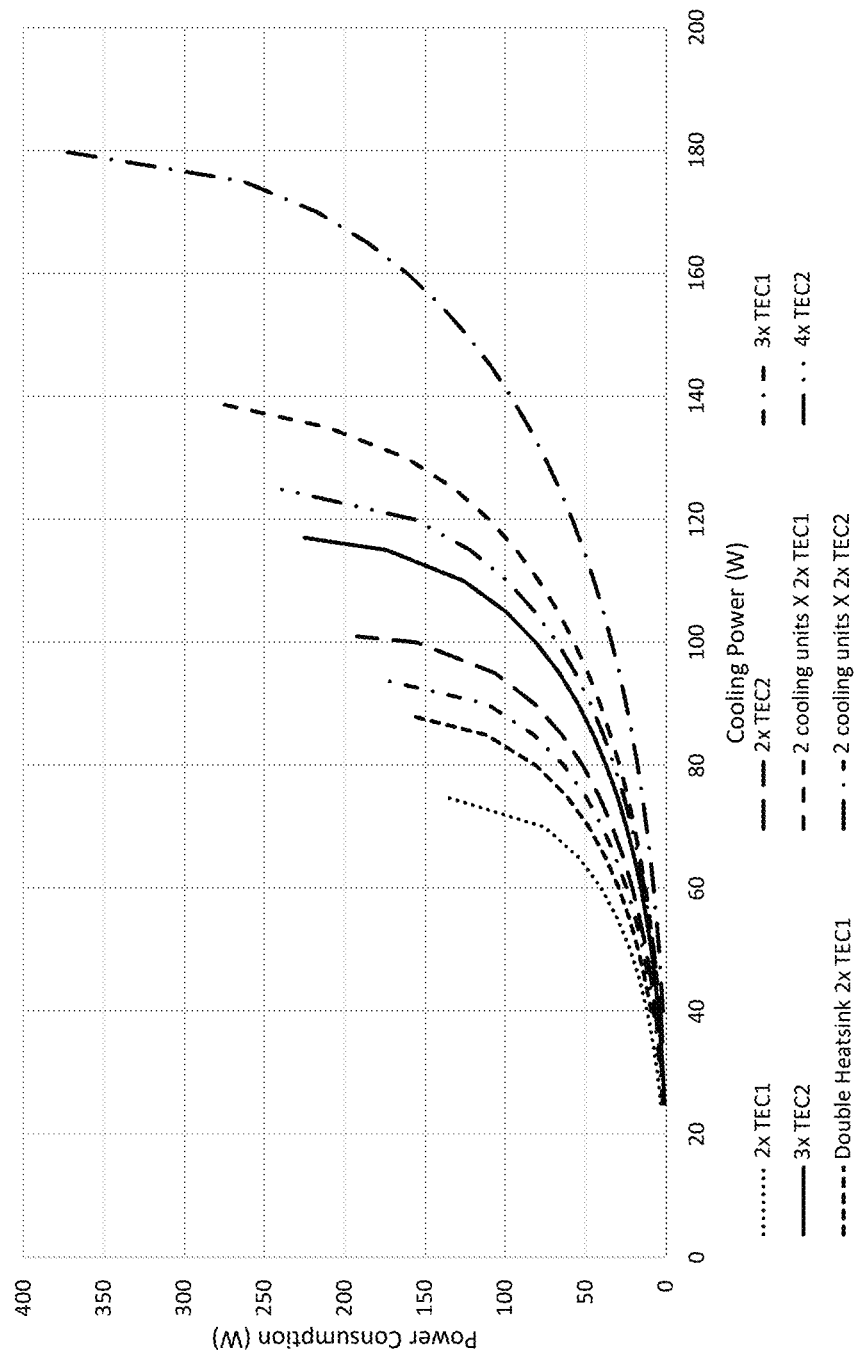
FIG. 24 illustrates a comparison between several different thermoelectric cooler (TEC) configurations.

FIG. 24 illustrates a comparison between several different thermoelectric cooler (TEC) configurations. The graph shows cooling power vs. power consumption. TEC 1 has 127 couples and a maximum amperage of 6A. TEC2 has 161 couples and a maximum amperage of 9A. The graph compares multiple configurations, including two 127 couple, 6A TECs (2× TEC1); two 161 couple, 9A TECs (2× TEC2); three 127 couple, 6A TECs (3× TEC1); three 161 couple, 9A TECs (3× TEC2); two cooling units each containing two 127 couple, 6A TECs (2 cooling units X 2× TEC1); four 161 couple, 9A TECs (4× TEC); double heatsinks and two 127 couple, 6A TECs (double heatsink 2× TEC1); and two cooling units each containing two 161 couple couple, 9A TECs (2 cooling units X 2× TEC2). As is seen by the graph, efficiency degrades as the maximum cooling capacity is approached.

Figure 25:
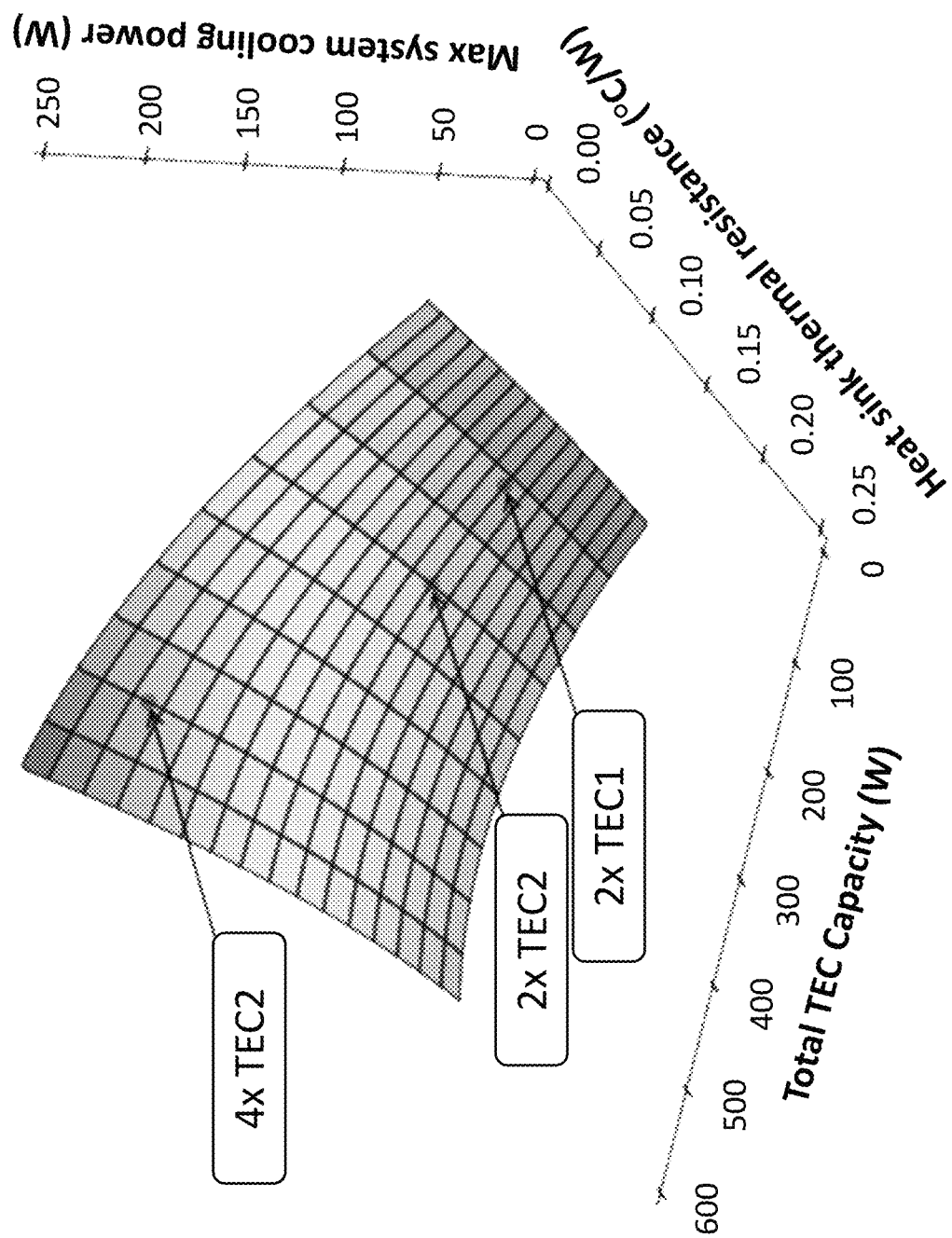
FIG. 25 is three-dimensional graph showing the total thermoelectric cooler (TEC) capacity vs. the heat sink thermal resistance vs. the maximum system cooling power for three configurations.

FIG. 25 is three-dimensional graph showing the total thermoelectric cooler (TEC) capacity vs. the heat sink thermal resistance vs. the maximum system cooling power for two 127 couple, 6A TECs (2× TEC1); two 161 couple, 9A TECs (2× TEC2); and four 161 couple, 9A TECs (4× TEC2). TEC capacity and heat sink capacity are increased together for best power increase.

Figure 26:
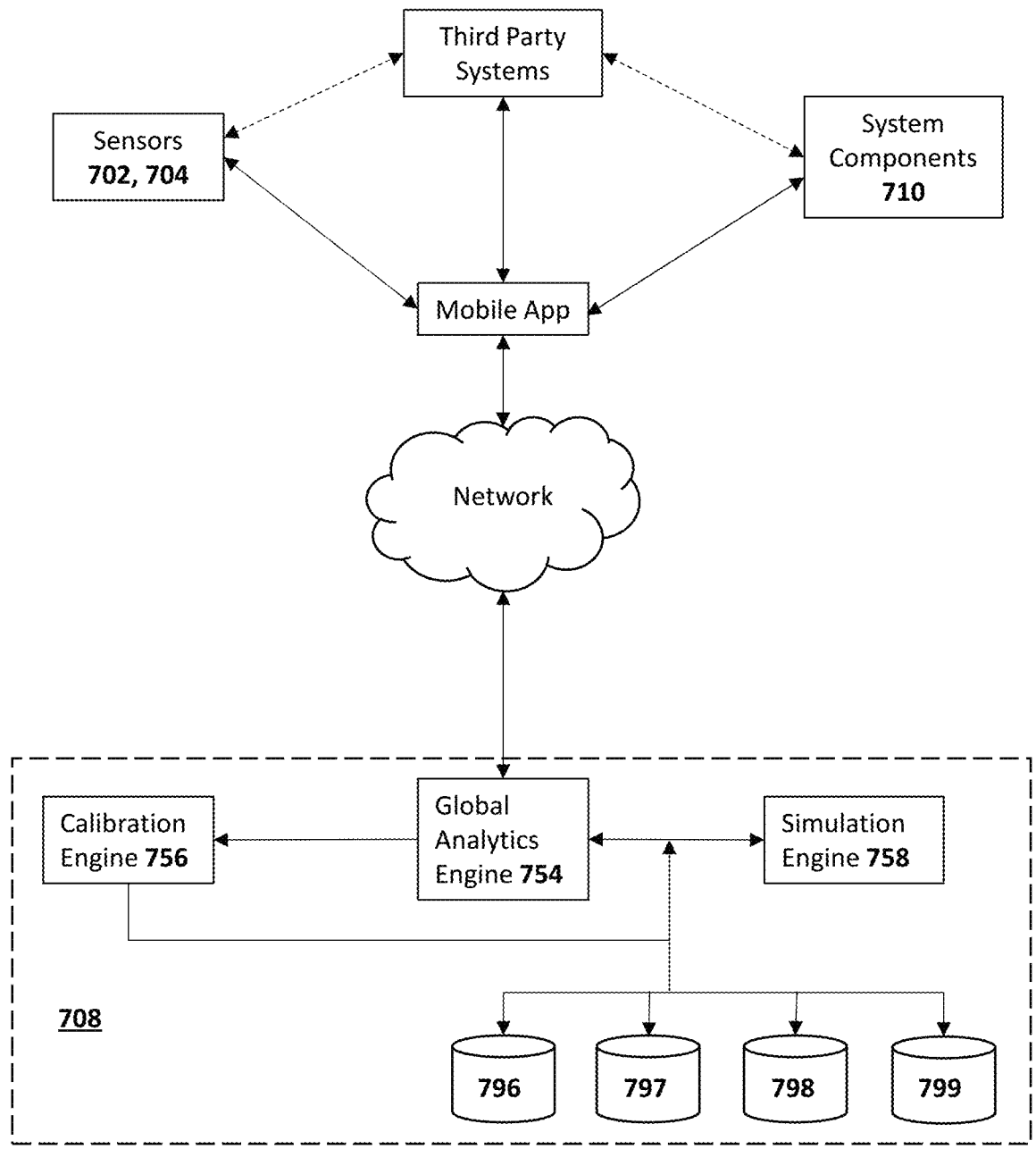
FIG. 26 is a block diagram of one embodiment of the system architecture.

As shown in FIG. 26, in one embodiment, the remote server 708 hosts a global analytics engine 754, a calibration engine 756, a simulation engine 758, a reasoning engine 759, and databases 796, 797, 798, and 799. Although four databases are shown, it is equally possible to have any number of databases greater than one. The global analytics engine 754 generates predicted values for a monitored stress reduction and sleep promotion system using a virtual model of the stress reduction and sleep promotion system based on real-time data. The calibration engine 756 modifies and updates the virtual model based on the real-time data. Any operational parameter of the virtual model is modified by the calibration engine 756 as long as the resulting modification is operable to be processed by the virtual model.

The global analytics engine 754 analyzes differences between the predicted values and optimized values. If the difference between the optimized values and the predicted values is greater than a threshold, then the simulation engine 758 determines optimized values of the monitored stress reduction and sleep promotion system based on the real-time data and user preferences. In one embodiment, the global analytics engine 754 determines whether a change in parameters of the system components 710 is necessary to optimize sleep based on the output of the simulation engine 758. If a change in parameters is necessary, the new parameters are transmitted to a mobile application on the remote device and then to the system components 710. The calibration engine 756 then updates the virtual model with the new parameters. Thus, the system autonomously optimizes the stress reduction and sleep promotion system (e.g., surface temperature) without requiring input from a user.

In another embodiment, the remote server 708 includes a reasoning engine 759 built with artificial intelligence (AI) algorithms. The reasoning engine 759 is operable to generate a reasoning model based on multiple sets of training data. The multiple sets of training data are a subset of global historical subjective data, global historical objective data, global historical environmental data, and global profile data. For example, a user's stress level and/or sleep efficiency significantly improve after engaging in an activity over a period of time, which is then included in the training data. The training data includes context data (e.g., baseline data, body sensor data) and action data (e.g., activity data, system component use). The reasoning model is updated periodically when there is an anomaly indicated in the action data produced by the reasoning data based on the context data. Each of U.S. Pat. No. 9,922,286 titled "Detecting and Correcting Anomalies in Computer-Based Reasoning Systems" and U.S. application Ser. No. 15/900,398 is incorporated herein by reference in its entirety.

Figure 27:
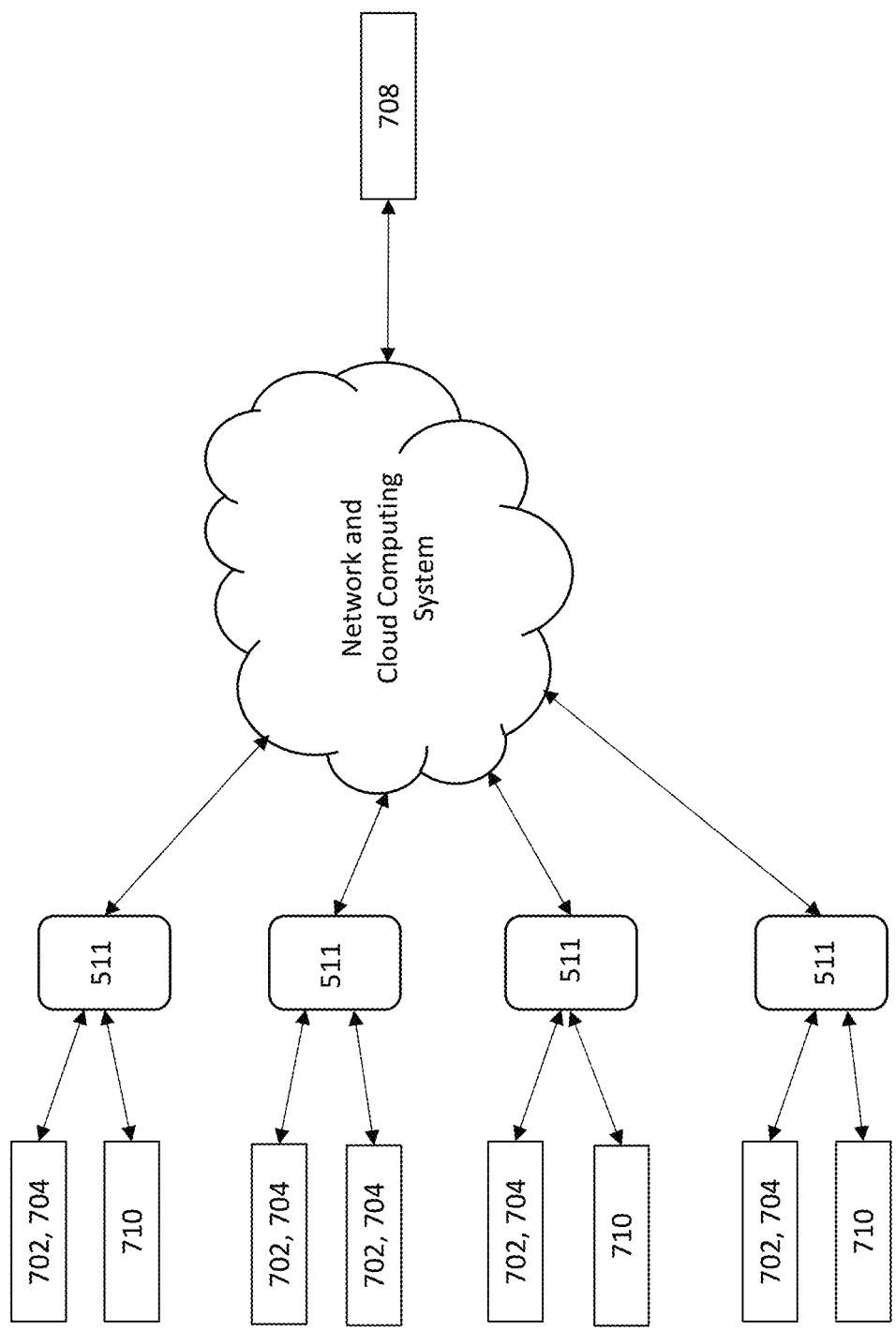
FIG. 27 is an illustration of a network of stress reduction and sleep promotion systems.

FIG. 27 is an illustration of a network of stress reduction and sleep promotion systems. Data from multiple users is stored on a remote server 708. The remote server 708 is connected through a network and cloud computing system to a plurality of remote devices 511. Each of the plurality of remote devices 511 is connected to body sensors 702 and/or environmental sensors 704, as well as system components 710. Although one remote server is shown, it is equally possible to have any number of remote servers greater than one. A user opts into sending their data to the remote server 708, which is stored in at least one database on the remote server 708. The simulation engine on the remote server 708 is operable to use data from the multiple users to determine customized and optimized sleep settings for the user based on personal preferences (e.g., a target number of hours of sleep, a preferred bed time, a preferred wake time, a faster time to fall asleep, fewer awakenings during the sleeping period, more REM sleep, more deep sleep, and/or a higher sleep efficiency) or physical condition (e.g., weight loss, comfort, athletic recovery, hot flashes, bed sores, depression). In one example, the temperature settings for a temperature-conditioned mattress pad for a user with hot flashes are automatically determined by the simulation engine examining data obtained from other users with hot flashes and a temperature-conditioned mattress pad stored in databases on the remote server. The simulation engine is also operable to use data from the multiple users to provide recommendations (e.g., activities, system components) to users with a similar background (e.g., gender, age, health condition).

The stress reduction and sleep promotion system includes a virtual model of the stress reduction and sleep promotion system. The virtual model is initialized based on the program selected. The virtual model of the stress reduction and sleep promotion system is dynamic, changing to reflect the status of the stress reduction and sleep promotion system in real time or near-real time. The virtual model includes information from the body sensors and the environmental sensors. Based on the data from the body sensors and the environmental sensors, the virtual model generates predicted values for the stress reduction and sleep promotion system. A sleep stage (e.g., awake, Stage N1, Stage N2, Stage N3, REM sleep) for the user is determined from the data from the body sensors.

The stress reduction and sleep promotion system is monitored to determine if there is a change in status of the body sensors (e.g., change in body temperature), the environmental sensors (e.g., change in room temperature), the system components (e.g., change in temperature of mattress pad), or sleep stage of the user. If there is a change in status, the virtual model is updated to reflect the change in status. Predicted values are generated for the stress reduction and sleep promotion system. If a difference between the optimized values and the predicted values is greater than a threshold, a simulation is run on the simulation engine to optimize the stress reduction and sleep promotion system based on the real-time data. The simulation engine uses information including, but not limited to, global historical subjective data, global historical objective data, global historical environmental data, and/or global profile data to determine if a change in parameters is necessary to optimize the stress reduction and sleep promotion system. In one example, the temperature of the mattress pad is lowered to keep a user in Stage N3 sleep for a longer period of time. In another example, the mobile application provides recommendations of an activity to a user.

Figure 28:
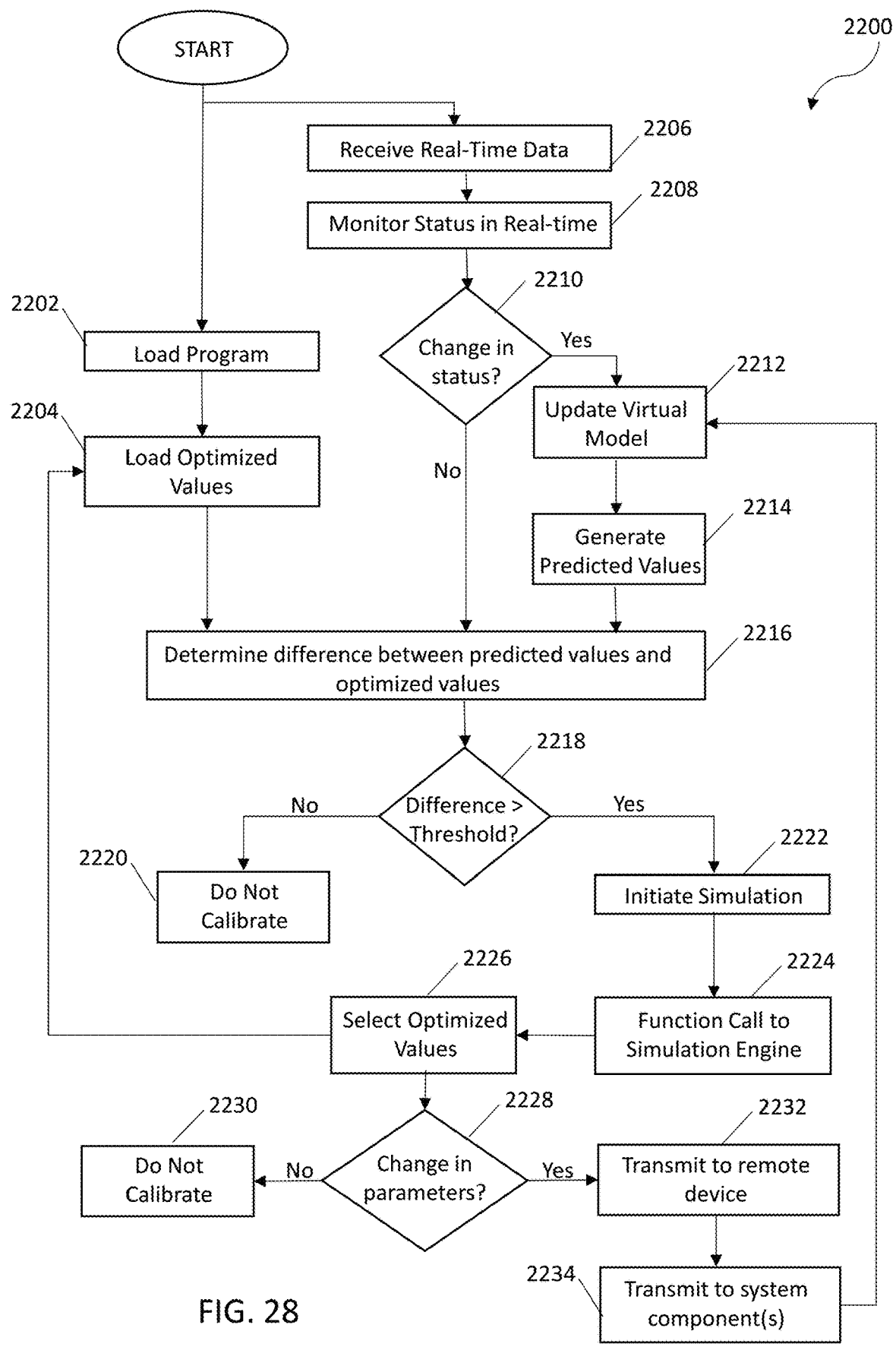
FIG. 28 is a diagram illustrating an example process for monitoring a stress reduction and sleep promotion system and updating a virtual model based on monitored data.

FIG. 28 is a diagram illustrating an example process for monitoring a stress reduction and sleep promotion system and updating a virtual model based on monitored data. First, in step 2202, a program to control the stress reduction and sleep promotion system is loaded onto a remote device. In a preferred embodiment, the program is a predefined program or customized program based on user preferences. Optimized values including, but not limited to, the sleep status, parameters for system components, and/or times for changes, from the program are loaded onto the global analytics engine in step 2204. Real-time data is received by the remote server via the remote device in step 2206. The real-time data is used to monitor the status of the stress reduction and sleep promotion system in step 2208. As described above, the stress reduction and sleep promotion system includes body sensors, environmental sensors, a remote device with local storage, a remote server, and system components. Accordingly, the status of the body sensors, the environmental sensors, and the system components are monitored in step 2208, as well as the sleep status of a user. In step 2210, a determination is made regarding whether there is a change in the status of the monitored devices and/or the sleep state. If there is a change, then the virtual model is updated in step 2212 by the calibration engine to reflect the status change, i.e., the corresponding virtual components data is updated to reflect the actual status of the various monitored devices.

In step 2214, predicted values for the monitored stress reduction and sleep promotion system are generated based on the current, real-time status of the monitored system. In one embodiment, the predicted values include, but are not limited to, sleep stage (e.g., awake, Stage N1, Stage N2, Stage N3, REM Sleep). In step 2216, the optimized values loaded in step 2204 are compared with the predicted values obtained in step 2214.

Accordingly, meaningful predicted values based on the actual condition of monitored stress reduction and sleep promotion system are generated in step 2214. These predicted values are then used to determine if further action should be taken based on the results of the comparison in step 2216. For example, if it is determined in step 2218 that the difference between the predicted values and the optimized values is less than or equal to a threshold, then a do not calibrate instruction is issued in step 2220. If the difference between the real-time data and the predicted values is greater than the threshold, as determined in step 2218, then an initiate simulation command is generated in step 2222.

In step 2224, a function call to the simulation engine is generated in response to the initiate simulation command. The simulation engine selects optimized values for the stress reduction and sleep promotion system in step 2226. These optimized values are updated on the global analytics engine in step 2204. Based on the output of the simulation engine, the global analytics engine determines if the optimized values require a change in parameters of the stress reduction and sleep promotion system (e.g., temperature of mattress pad, room temperature, lighting, mattress firmness, mattress elevation) in step 2228. In a preferred embodiment, the simulation engine uses the global historical subjective data, the global historical objective data, the global historical environmental data, and the global profile data to determine if the change in parameters is necessary. If a change in parameters is not necessary, a do not calibrate instruction is issued in step 2230. If a change in parameters is necessary, the new parameters are transmitted to the remote device in step 2232. The remote device transmits the new parameters to the system components in step 2234.

The calibration engine updates the virtual model in step 2212 based on the real-time data and the new parameters. Predicted values are then generated in step 2214. In this manner, the predicted values generated in step 2214 are not only updated to reflect the actual status of monitored stress reduction and sleep promotion system, but they are also updated to reflect natural changes in monitored system as the user moves through the sleep cycle. Accordingly, realistic predicted values are generated in step 2214.

As previously mentioned, the at least one remote device preferably has a user interface (e.g., a mobile application for a smartphone or tablet) that allows the stress reduction and sleep promotion system to adjust the parameters of the stress reduction and sleep promotion system. The parameters of the stress reduction and sleep promotion system (e.g., target temperatures of a mattress pad) are manipulated through the sleeping period using a predefined program or a customized program based on user preferences to produce a deeper, more restful sleep.

Because the target temperatures are able to be set at any time, those target temperatures are able to be manipulated through the sleeping period in order to match user preferences or a program to correlate with user sleep cycles to produce a deeper, more restful sleep.

In one embodiment, the mobile application measures a time when a user began attempting to sleep (TATS), a TATS start time, a TATS end time, a time in bed (TIB), a TIB start time, and/or a TIB end time. The mobile application calculates a total TATS duration based on the TATS start time and the TATS end time. The mobile application also calculates a total TIB duration based on the TIB start time and the TIB end time. In one embodiment, the TATS start time, the TATS end time, the TIB start time, and/or the TIB end time are indicated by the user (e.g., by pressing a button in the mobile application). Alternatively, the TATS start time, the TATS end time, the TIB start time, and/or the TIB end time are determined by sensors. In one example, the TATS start time is determined by a user's eyes closing while in bed. In another example, the TATS end time is determined by increased motion as measured by a movement sensor and/or opening of the eyes. In yet another example, the TIB start time is determined by sensors indicating a user is horizontal and/or bed or room sensors indicating the user is in bed. In still another example, the TIB end time is determined by sensors indicating a user is not horizonal and/or bed or room sensors indicating the user is not in bed.

The mobile application is operable to determine whether a user is awake or asleep. The state of wakefulness (i.e., "awake") is characterized by cognitive awareness and/or consciousness, responsiveness to environmental cues, sustained movement detected by a movement sensor, beta and/or alpha waves as detected by EEG, increased heart rate, increased respiration, increased blood pressure, increased electrodermal activity, increased body temperature, open eyes, voluntary eye movements, and/or increased EMG on the chin. The state of sleep (i.e., "asleep") is characterized by loss of alertness and/or consciousness, lack of response to environmental cues, lack of movement, reduction in alpha waves as detected by EEG, increased theta and delta waves as detected by EEG, decreased heart rate, decreased respiration, decreased blood pressure, decreased body temperature, closed eyes, eye twitches, and/or decreased oxygen saturation.

In a preferred embodiment, the mobile application is operable to measure an initial sleep onset time and/or a final awakening time. The initial sleep onset time is a first occurrence of sleep after the TATS start time. The final awakening time is a time immediately after the last occurrence of sleep before the TATS end time. In one embodiment, the mobile application calculates a latency to sleep onset as the duration of a time interval between the TATS start time to the initial sleep onset time. In another embodiment, the mobile application calculates a latency to arising as the duration of a time interval between the final awakening time to the TATS end time. In a preferred embodiment, the mobile application is operable to calculate a sleep efficiency percentage. In one embodiment, the sleep efficiency percentage is defined as the total sleep time divided by the total TATS duration. In an alternative embodiment, the sleep efficiency percentage is defined as the total sleep time divided by the total TIB duration.

In one embodiment, the mobile application is operable to determine a total sleep period duration, a total sleep time, a sleep maintenance percentage, a total wakefulness duration, a wakefulness duration after initial sleep onset, a total number of awakenings, an awakening rate per hour, and/or a sleep fragmentation rate.

In another embodiment, the mobile application is operable to determine REM sleep, N1 sleep, N2 sleep, and/or N3 sleep. REM sleep is characterized by low-voltage, mixed-frequency EEG activity with less than 15 seconds of alpha activity, saw-tooth theta EEG activity, rapid eye movements, and/or decreased or absent EMG activity on the chin. N1 sleep is characterized by low-voltage, mixed-frequency EEG activity with less than 15 seconds of alpha activity in a 30-second epoch, no sleep spindles or K complexes, possible slow rolling eye movements, and/or diminished EMG activity on the chin. N2 sleep is characterized by sleep spindle and/or K complex activity, absence of eye movements, and/or diminished EMG activity on the chin. N3 sleep is characterized by high amplitude (e.g., greater than 75u V peak-to-peak), slow wave (e.g., frequency of 4 Hz or less) EEG activity. In yet another embodiment, the mobile application is operable to calculate REM sleep duration, percentage, and latency from sleep onset; N1 sleep duration, percentage, and latency from sleep onset; N2 sleep duration, percentage, and latency from sleep onset; and/or N3 sleep duration, percentage, and latency from sleep onset.

Alternatively, the calculations and determining of sleep states described above are determined over the network on a remote server. In one embodiment, the calculations and determining of sleep states are then transmitted to at least one remote device. In yet another embodiment, the calculations and determining of sleep states described above are determined using third party software and transmitted to the mobile application.

The mobile application preferably serves as a hub to interface with the system components, the body sensors, the environmental sensors, and/or at least one third-party application (e.g., Apple® Health, MyFitnessPal®, nutrition tracker). The mobile application is operable to obtain data from a mattress pad (e.g., OOLER) and/or a wearable (e.g., OURA, Apple Watch®, Fitbit®).

Sleep Density vs. Sleep Efficiency

There are numerous sleep tracking algorithms. However, generally many sleep tracking algorithms focus on sleep efficiency. Sleep efficiency is based on total time sleeping versus time in bed. Therefore, the focus becomes on sleep latency, wake-ups, and time spent sleeping in an optimal sleep window rather than whether a user feels recovered and well rested.

In contrast, deep sleep or slow wave sleep (SWS) is the most effective way for an average user to feel recovered from sleep. As a result, the present invention is directed to increasing a total time and/or a percentage of time in deep sleep. In one embodiment, a sleep density is defined as the percentage of time in deep sleep. To increase the total time and/or the percentage of time in deep sleep, a core body temperature of the user is cooled within a window of non-shivering thermogenesis.

One of the unfortunate effects of aging is that less time is spent in deep sleep. Healthy people in their 20s spend about 20% of a sleeping period in Stage 3, while a typical 40- or 50-year-old spends about 10% of a sleeping period in Stage 3. By age 70 or 80, an average of about 5% of a sleeping period is spent in Stage 3, and sometimes about 2%. One way to approximate an age of an individual is to measure an amount of Stage 3 sleep (e.g., using EEG).

FIG. 29 is an average deep sleep percentage by age. In one embodiment, the stress reduction and sleep promotion system includes a target percentage of deep sleep by age. An example of target percentages of deep sleep by age is shown in FIG. 30. In another embodiment, the target percentage of deep sleep by age is equal to the average deep percentage by age. In yet another embodiment, the target percentage of deep sleep for an obese person is equal to the average deep sleep percentage by age of the next highest age group. For example, the target deep sleep of a 36-year old obese user is equal to the average deep sleep percentage by age of 46-55-year-old users (e.g., 12-16%).

Temperature Regulation

As previously described, humans are homeothermic and require a nearly constant internal body temperature for maintaining normal physiological functions. Body temperature increases during exercise and fever, and varies with temperature extremes of the surrounding environment. The homeostatic mechanisms for regulating body temperature represent the thermoregulatory system. Body temperature is controlled by balancing heat production against heat loss.

As shown in PRIOR ART FIG. 31, the body is divided into a warm internal core and a cooler outer shell. The internal body temperature is the temperature of the vital organs inside the head and trunk, which, together with a variable amount of other tissue, comprise the warm internal core. The temperature of the internal core of the body remains very constant, within ±1.1° C. (2° F.). The temperature of the outer shell is strongly influenced by the environment, and is not regulated within narrow limits like the internal body temperature. The thermoregulatory responses strongly affect the temperature of the shell, especially its outermost layer, the skin. Heat is transferred within the body both from the core to the skin and from major sites of heat production to the rest of the body. The shell lies between the core and the environment. All heat leaving the body core, except heat lost through the respiratory tract, must pass through the shell before being lost to the environment. Thus, the shell insulates the core from the environment.

Heat production is a principal by-product of metabolism. The rate of heat production (i.e., metabolic rate) is determined by factors including, but not limited to, basal metabolic rate of all the cells of the body, muscle activity, hormones (e.g., thyroxine, growth hormone, testosterone, epinephrine, norepinephrine), sympathetic stimulation on the cells, and/or metabolism needed for digestion, absorption, and storage of food.

Heat is transported within the body by two means: conduction through the tissues and convection by the blood. Heat flow by conduction varies directly with the thermal conductivity of the tissues. Heat flow by convection depends on the rate of blood flow, which is controlled by the degree of vasoconstriction of the arterioles and the arteriovenous anastomoses that supply blood to the skin. This vasoconstriction is controlled almost entirely by the sympathetic nervous system in response to changes in core body temperature and changes in environmental temperature.

PRIOR ART FIG. 32 illustrates heat loss of the body. Heat loss occurs through a variety of mechanisms, including radiation (e.g., infrared heat rays), conduction, convection, evaporation, and respiration. When the body temperature is greater than the environmental temperature, a larger quantity of heat is radiated from the body than is radiated to the body. Conduction to air accounts for approximately 15% and direct conduction from the body surface to solid objects accounts for approximately 3%. Convection is the removal of heat from the body by convection air currents. Evaporation is heat loss from the body via sweat. Respiration accounts for approximately 10% of heat loss.

Temperature Changes Using Cold Therapy

As previously described, cold therapy is used to treat insomnia and/or provide more restful sleep. The core body temperature naturally decreases by 0.56-1.1° C. (1-2° F.) during a sleep period as shown in PRIOR ART FIG. 33.

Deep sleep is Stage 3 sleep, which shows up on an EEG as delta waves. It is more difficult to wake up people in deep sleep than light sleep. Additionally, sleep inertia results from being woken up during deep sleep. Further, individuals in deep sleep are less likely to waken in response to external stimuli than those in light sleep. As previously stated, deep sleep is the most refreshing sleep, as subjectively described by individuals after waking up. However, aging results in less deep sleep.

Deep sleep provides many benefits. The pituitary gland secretes human growth hormone in the first deep sleep episode of the night. Deep sleep is also associated with repairing and regrowing tissues, building bone and muscle, and strengthening the immune system. If an individual does not get enough deep sleep to feel refreshed and is allowed to sleep for an extra amount of time the following night, almost all of the missed deep sleep is recovered, while the amount of REM and light sleep are lower.

By decreasing a temperature of the mattress pad following sleep onset, it is possible to increase an amount of deep sleep. In a preferred embodiment, a total time and/or a percentage of time in deep sleep is increased by decreasing the temperature of the mattress pad. In one embodiment, an amount of deep sleep in a first sleep cycle is increased by decreasing the temperature of the mattress pad. The temperature of the mattress pad is cooler in the first half of the sleeping period and warmer in the second half of the sleeping period. Advantageously, this keeps the user cool to thermally neutral as the user progresses in the circadian rhythm to the second half of the sleeping period where the user's core body temperature increases. In a last quarter of the sleeping period, the mattress pad maintains thermal neutrality, which allows the user to maintain sleep and permits REM-heavy sleep cycles. Humans are in the thermal neutral zone (i.e., thermally neutral) when the rate of heat production equals the rate of heat loss to the environment. The thermal neutral zone is shown in PRIOR ART FIG. 34.

Chronic insomniacs and commuters who chronically sleep 6 hours or less are able to improve to 2 hours of deep sleep without increasing the total time spent sleeping. Using temperature modified sleep (e.g., cooling), improvements in deep sleep, heart rate variability, and resting heart rate are possible without adding additional sleep time. This is improved sleep density. The amount of light sleep becomes shorter, with only a small change in the amount of REM sleep.

Non-Shivering Thermogenesis

Non-shivering thermogenesis increases metabolic heat production without producing mechanical work. Skeletal muscle and brown adipose tissue (BAT) are the major sources of heat produced by non-shivering thermogenesis in adults. The metabolic rate of skeletal muscle and BAT is controlled by norepinephrine released from adrenergic nerve terminals and is further mediated locally by an uncoupling protein, UCP-1. Additional information regarding non-shivering thermogenesis is found in Cannon, Barbara, and Jan Nedergaard. "Nonshivering thermogenesis and its adequate measurement in metabolic studies." Journal of Experimental Biology 214.2 (2011): 242-253, which is incorporated herein by reference in its entirety. Benefits of non-shivering thermogenesis include increased fat loss, less inflammation, increased lifespan, strengthened nervous system, increased healing and recovery, regulated blood sugar levels, improved sleep quality, strengthened immune system, enhanced detoxification, reduced pain, and increased bone health.

Heart Rate

Heart rate (i.e., pulse) is dependent on many factors including, but not limited to, age, health, gender, and fitness level. Generally, a lower resting heart rate indicates a higher level of cardiovascular health, while a higher resting heart rate indicates a higher risk of cardiac events (e.g., stroke, heart attack). PRIOR ART FIG. 35 includes a table of resting heart rates for men and women with a rating (i.e., athletes, excellent, good, above average, average, below average, and poor) for different age groups. Therefore, a high resting heart rate is an indicator of a lack of activity, overtraining, mental stress, emotional stress, sleep deprivation, dehydration, and/or development of a medical condition (e.g., Type 2 diabetes). Further, medications impact resting heart rate. For example, medications that treat asthma, attention deficit disorder, depression, and obesity often increase resting heart rate, while medications that treat hypertension and heart conditions (e.g., beta blockers, calcium channel blockers) often decrease resting heart rate. Additionally, resting heart rate sometimes indicates an impending illness. For example, resting heart rate will generally increase a few days before the onset of flu systems.

Heart rate varies throughout the day. An optimal heart rate curve during sleep is a hammock-shaped curve as shown in PRIOR ART FIG. 36. The body relaxes and blood pressure and heart rate drop during the first sleep cycles. Heart rate is lowest during the middle of a sleep period when the amount of melatonin is highest. Heart rate then increases in preparation to wake.

Heart Rate Variability

Heart rate variability is dependent on many factors including, but not limited to, age, health, gender, and fitness level. PRIOR ART FIG. 37 is a graph of HRV normal values vs. age and sex. HRV, like deep sleep, declines with age. This decline in HRV indicates decreased parasympathetic activation with respect to age. Higher HRV is correlated with increased fitness and health, while lower HRV indicates a higher biological age. As seen in PRIOR ART FIG. 37, gender differences in HRV decrease after the age of 55 years, due to age-related hormone effects in women (i.e., menopause). In a preferred embodiment, HRV is based on a room mean square of the successive differences (RMSSD). Alternatively, HRV is based on a standard deviation of NN intervals (SDNN), a standard deviation of RR intervals (SDRR), a number of pairs of successive NN intervals that differ by more than 50 ms (NN50), a proportion of NN50 divided by a total number of NN intervals, a natural log of the RMSSD (ln(RMSSD)), or a ratio of low frequency to high frequency power (LF/HF). Low frequency power is measured in a frequency band of 0.04-0.15 Hz. High frequency power is measured in a frequency band of 0.15-0.4 Hz.

In one embodiment, a normalized LF value and a normalized HF value are utilized to determine a balance between the sympathetic nervous system and the parasympathetic nervous system. The normalized LF value and the normalized HF value are expressed as a percentage of the sum of LF and HF (e.g., normalized HF=HF/(LF+HF)). Ideally, the normalized LF value and the normalized HF value are equal, which indicates optimal body function. If the ratio is larger than 0.75:0.25 (e.g., 0.8:0.2) or smaller than 0.25:0.75 (e.g., 0.2:0.8), this is an indication of inadequate recovery, high stress, chronic stress, fatigue, and/or malfunction within the body.

Heart rate variability is also an indication of recovery during a sleep period. An HRV value at sleep onset (e.g., night) shows stress accumulated during a waking period (e.g., day). An HRV value at waking (e.g., morning) shows recovery status (e.g., during night) and readiness for activity during the waking period (e.g., day). Therefore, HRV is used to optimize a training and/or an exercise schedule. A high HRV at the start of a sleeping period corresponds to a stressful or heavy training day, while a low HRV at the start of a sleeping period corresponds to an easy or light training day. A high HRV at waking corresponds to a good recovery during the sleeping period, while a low HRV at waking corresponds to an incomplete recovery during the sleeping period.

In one embodiment, RMSSD is used to determine recovery during a sleeping period. In another embodiment, HRV is measured in intervals (e.g., 3-minute intervals) throughout the sleeping period. In yet another embodiment, a linear fit of RMSSD is completed for HRV values obtained throughout the sleeping period. A positive slope of the linear fit of RMSSD indicates a good recovery, a slope of about 0 of the linear fit of RMSSD indicates an easy or light training day with little need for recovery, and a negative slope of the linear fit of RMSSD indicates a stressful or heavy training day with incomplete recovery. In still another embodiment, at least one historical RMSSD value is compared to an RMSSD value during a most recent sleeping period. For example, the at least one historical RMSSD value is an average RMSSD value and/or a histogram obtained over a period of time (e.g., over a 7-day period, over a 30-day period, over a 6-week period, over all RMSSD values). In one embodiment, an HRV at the start of a sleeping period is obtained by averaging all HRV values obtained in a time period (e.g., 30 minutes, 60 minutes, 90 minutes) following sleep onset and an HRV at waking is obtained by averaging all HRV values obtained in a time period (e.g., 30 minutes, 60 minutes, 90 minutes) prior to waking.

Manipulating Sleep

In a preferred embodiment, the stress reduction and sleep promotion system includes AI algorithms and/or machine learning to promote recovery in sleep by combining deep sleep, HRV, and resting heart rate. In another embodiment, the stress reduction and sleep promotion system also incorporates REM sleep, sleep onset, movement, respiration rate, and/or body temperature (e.g., core body temperature) into the AI algorithms and/or the machine learning. In yet another embodiment, the stress reduction and sleep promotion system incorporates at least one waking period, a time of the at least one waking period, and/or a duration of the at least one waking period.

In one embodiment, core body temperature (CBT) is set as relative to an individual CBT minimum (set at 0°). Each 30 second interval is assigned a circadian phase between 0° to 359.9°. Each 360° period is equivalent to a 24-hour day (i.e., circadian rhythm). In one embodiment, the data is processed using a nonlinear mixed model. Additional information regarding the nonlinear mixed model is available in Boudreau, Philippe et al., "Circadian variation of heart rate variability across sleep stages" Sleep vol. 36,12 1919-28. 1 Dec. 2013, doi: 10.5665/sleep.3230, which is incorporated herein by reference in its entirety. A CBT minimum generally occurs around 5 am on average, but an early riser frequently hits the CBT minimum earlier.

After a user's normal circadian rhythm is defined as described above, an average minimum CBT, a baseline of HRV, and sleep stage data are used to create a baseline. In a preferred embodiment, real-time data from body sensors (e.g., heart sensor, body temperature sensor, movement sensor) is used to modify a temperature of the mattress pad. However, some current sensors and wearables do not give accurate real-time information. Therefore, in one embodiment, data averages and/or baselines are analyzed with a rolling 7 days of data. Advantageously, this allows programmed temperature changes to modify sleep without real-time data from body sensors.

In one embodiment, the stress reduction and sleep promotion system is programmed for a deep sleep recovery focus. A deep sleep percentage has a 65% weighting, an HRV has a 20% weighting, and a resting heart rate has a 15% weighting. In another embodiment, a deep sleep percentage has a 50% weighting, an HRV has a 25% weighting, and a resting heart rate has a 25% weighting.

The stress reduction and sleep promotion system preferably incorporates data including, but not limited to, weight, age, gender, medications, sleep onset, desired wake time, sleep wake zone, sleep stage, pivot points for sleep cycles, athletic performance, heart rate, heart rate variability, body temperature, and/or stress. This data is obtained through the body sensors, the user input, the historical objective data, and/or the historical subjective data. The stress reduction and sleep promotion system analyzes the data to determine a core body temperature throughout a sleeping period, resting heart rate, heart rate variability, sleep cycles (including pivot points), deep sleep percentage, deep sleep timing, a number of sleep cycles containing deep sleep, a time of a minimum core body temperature, a bedtime core body temperature, and/or a morning core body temperature. The data is used to control core body temperature, sleep cycles, deep sleep percentage, pivot points, a number of wake times in a sleep period, a wake time, and/or sleep onset by varying the temperature of the mattress pad. Advantageously, this allows improvement in deep sleep, recovery, resting heart rate, metabolism, immune system function, stress levels, and/or athletic performance.

Figure 38A:
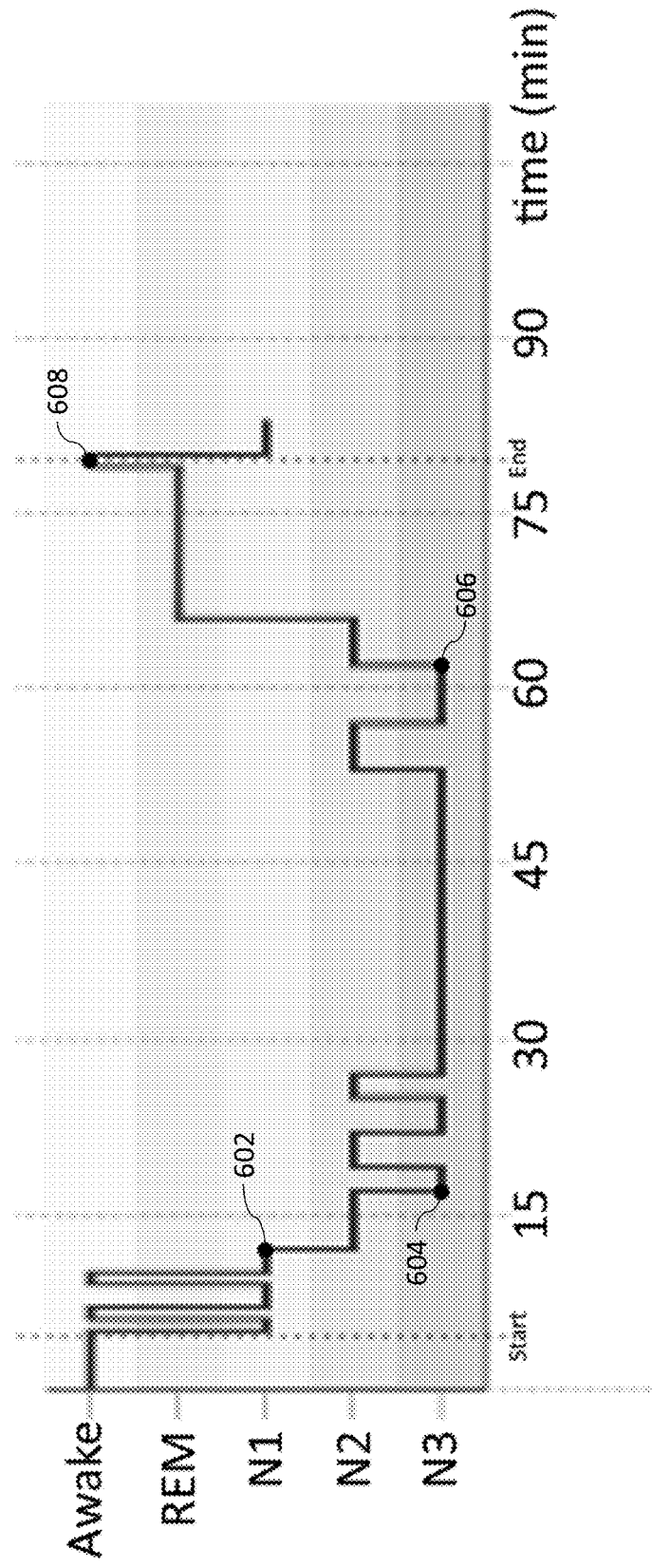
FIG. 38A illustrates a hypnogram of one sleep cycle prior to cooling.

FIG. 38A illustrates a hypnogram of one sleep cycle prior to cooling. The hypnogram includes four major pivot points 602, 604, 606, and 608. The first pivot point 602 is the point where the stress reduction and sleep promotion system begins to decrease the temperature of the mattress pad. The second pivot point 604 is the point where the temperature of the mattress pad has reached peak cooling. The third pivot point 606 is the point of movement out of deep sleep. The fourth pivot point 608 is the end of the sleep cycle. In one example, if a user wakes at the fourth pivot point 608 consistently, the stress reduction and sleep promotion system further lowers the temperature of the mattress pad by 0.56-1.1° C. (1-2° F.) at the third pivot point 606 to prevent waking at the end of the sleep cycle. In another example, the stress reduction and sleep promotion system raises the temperature of the mattress pad at the third pivot point 606 by 0.56-1.1° C. (1-2° F.) to encourage more REM sleep for a user who desires additional cognitive and/or emotional recovery. The pivot points are obtained from body sensors including, but not limited to, the body temperature sensor, the movement sensor, and/or the heart sensor.

Figure 38B:
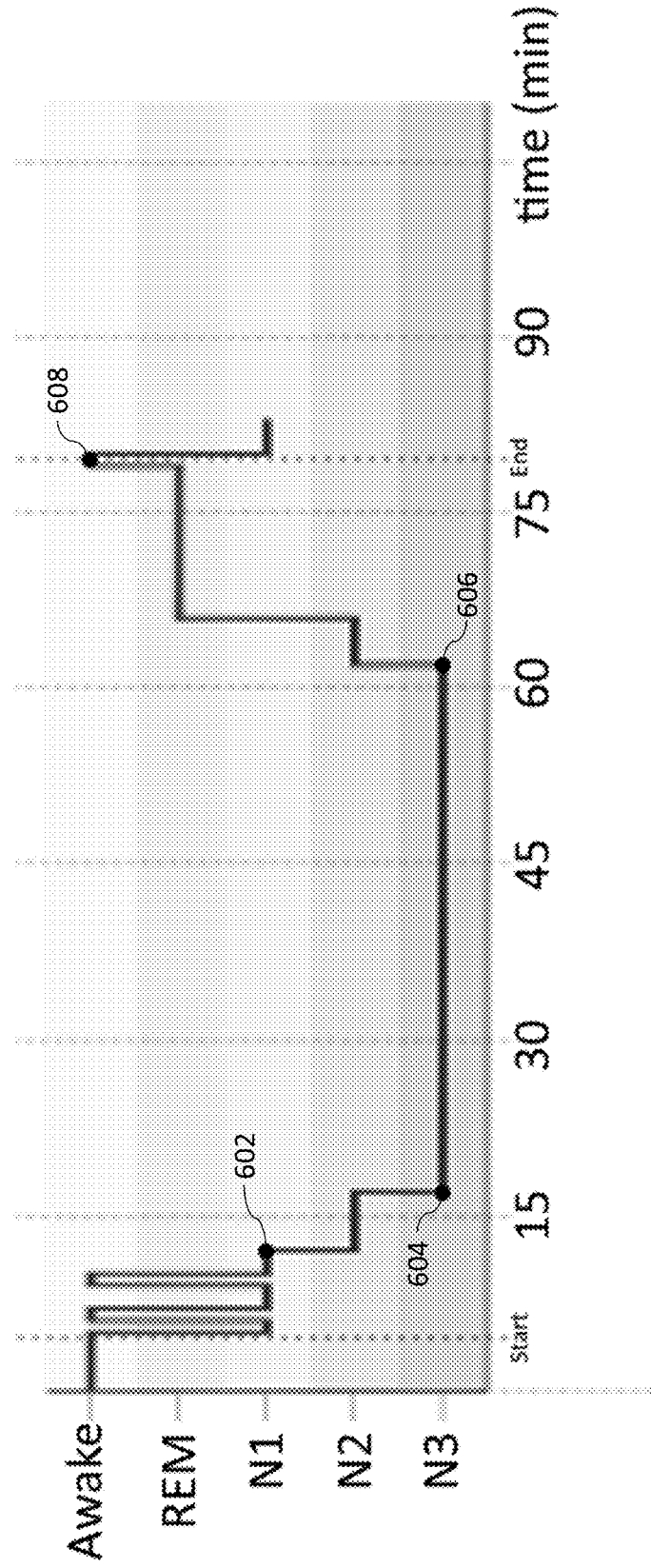
FIG. 38B illustrates a hypnogram of one sleep cycle after cooling.

FIG. 38B illustrates a hypnogram of one sleep cycle after cooling. The fluctuations between N2 and N3 sleep seen in the hypnogram of FIG. 38A diminish with cooling as seen in FIG. 38B.

Figure 39:
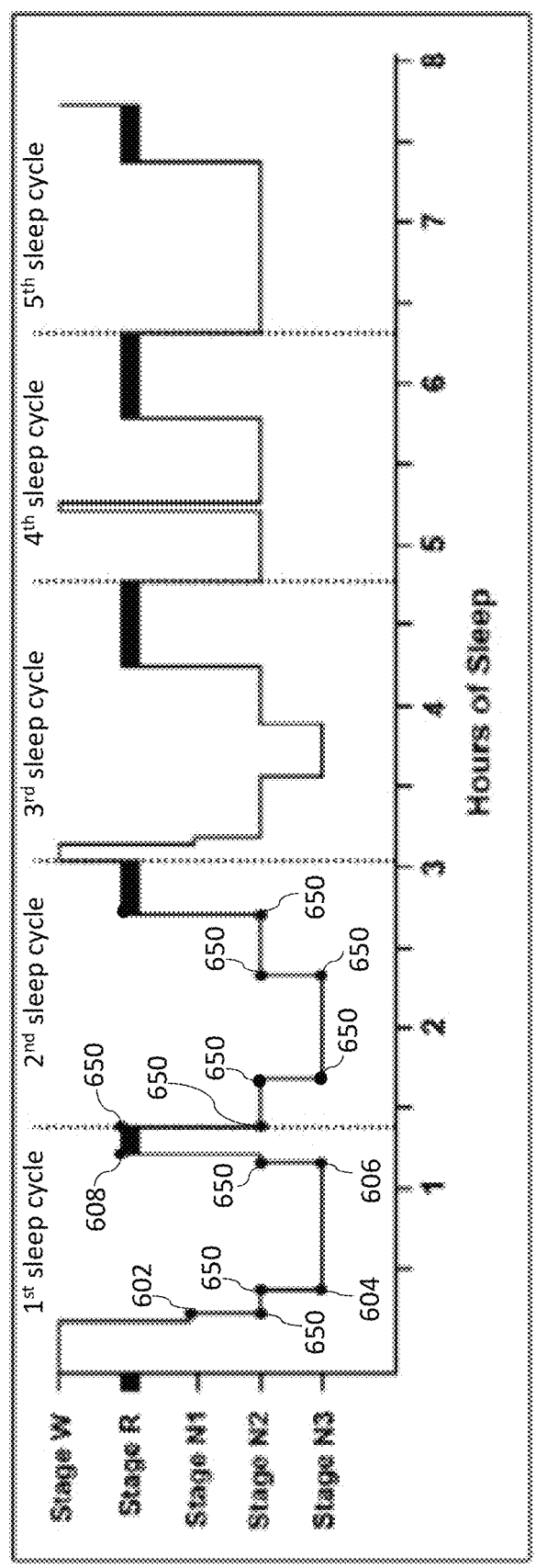
FIG. 39 illustrates a hypnogram of a sleeping period.

FIG. 39 illustrates a hypnogram of a sleeping period. The hypnogram includes a first sleep cycle, a second sleep cycle, a third sleep cycle, a fourth sleep cycle, and a fifth sleep cycle. The first sleep cycle preferably has at least 30 minutes of deep sleep and more preferably has about 40 minutes of deep sleep. The second sleep cycle preferably has at least 25 minutes of deep sleep. The third sleep cycle preferably has at least 20 minutes of deep sleep. The fourth sleep cycle preferably has at least 15 minutes of deep sleep. The fifth sleep cycle preferably has at least 5 minutes of deep sleep. For sleeping periods of less than 6 hours, it is likely that there are only four sleep cycles. The hypnogram includes the four major pivot points 602, 604, 606, and 608 and a plurality of minor pivot points 650.

In a first example, the stress reduction and sleep promotion system is used to increase deep sleep for a 40 year old user. The user has a starting baseline as follows: a core body temperature (CBT) of 36.8° C. (98.2° F.) at 5:30 AM, a sleep onset time of 10:00 PM, a wake time of 6:00 AM, a total deep sleep percentage of 11%, a total deep sleep amount of 56 minutes, an HRV average of 28, and a resting heart rate of 72 bpm. When the user attempts to go to sleep, the mattress pad is set at ambient temperature (i.e., room temperature). At sleep onset, the temperature of the mattress pad drops per a schedule to 15.6° C. (60° F.). In one example, the schedule is a decrease of 4.44° C. (8° F.) in 30 minutes after the user is in light sleep is a pivot point in the sleep cycle.

The user will no longer notice that the temperature of the mattress pad is cooler than might be comfortable for the user. The change to the above set points is clear on a sleep tracker, but the first sleep cycle is longer (e.g., double) and is often "deeper" than before temperature manipulated sleep. Additionally, a resting heart rate and a respiratory rate of the user drops. An HRV value also changes, but requires 3-7 sleeping periods (e.g., nights) of temperature manipulated sleep before showing a change. Over a period of 3 months, the user has a new baseline as follows: a core body temperature (CBT) of 36.6° ° C. (97.8° F.) at 4:05 AM, a sleep onset time of 10:00 PM, a wake time of 6:00 AM, a total deep sleep percentage of 19%, a total deep sleep amount of 1 hour 56 minutes, an HRV average of 54, and a resting heart rate of 66 bpm. Further, before blood work of the user indicated Hashimoto's disease with thyroid problems eventually leading to thyroid failure. Blood work of the user following temperature modified sleep indicated a complete reversal of symptoms and signs of disease in 6 months.

As previously described, in one embodiment, the mattress pad includes a warm awake feature. After the user reaches the minimum CBT, the body needs to warm up. The mattress pad needs to be thermally neutral to warm instead of cool. In one example, a warm awake feature increases the temperature of the mattress pad 4.44° C. (8° F.) in 30 minutes. In another example, a warm awake feature increases the temperature of the mattress pad 4.44° C. (8° F.) in 15 minutes. Advantageously, using a faster rate of warming allows a user who gets less than 7 hours of sleep (e.g., 6 hours) to maximize the amount of sleep obtained in a sleeping period.

In another example, the stress reduction and sleep promotion system is used to treat depression or other similarly presenting mental disorders from a sleep cycle perspective. Extensive evidence suggests that depression is closely related to difficulty sleeping. Insomnia is a disorder of excessive wakefulness during the night. This hyperarousal often masks sleepiness during the day. Depressed individuals often have a higher core body temperature than non-depressed individuals and a blunted core body temperature rhythm. Some depressed individuals have hyperthermia (e.g., a core body temperature of 0.83-1.1° C. (1.5-2° F.) greater than normal). Hyperthermia is linked to chronic inflammation, fatigue, and stress. Insomnia in combination with depression is also marked by disrupted REM sleep. REM sleep is hypothesized to control emotional regulation. Less REM sleep leads to less emotional processing, which contributes to depression.

In the example of treating depression, the user has a starting baseline as follows: a sleep onset time of 10:00 PM, a wake time of 6:00 AM, a total deep sleep percentage of 3%, a total deep sleep amount of 16 minutes, an HRV average of 22, and a resting heart rate of 74 bpm. The user reported regular night terrors, restless dreams, and frequent wake-ups. Over a period of 6 months, the user has a new baseline as follows: a sleep onset time of 10:00 PM, a wake time of 6:00 AM, a total deep sleep percentage of 12%, a total deep sleep amount of 1 hour 7 minutes, an HRV average of 78, and a resting heart rate of 63 bpm. Further, the user reported that the night terrors almost completely stopped and very few wake-ups at night.

In yet another example, the stress reduction and sleep promotion system is used to treat difficulty sleeping related to cancer treatment. Between a third and a half of all cancer patients have difficulty sleeping through the night according to the National Institutes of Health. Insomnia negatively impacts both the health and stamina of the patient both during and after cancer treatment. During the treatment process, CBT highs and lows of the circadian rhythm are disrupted. Often cold and warm therapy is needed to sleep and maintain the circadian rhythm. Immune system fluctuations due to the cancer treatment makes it difficult to maintain a consistent CBT.

In still another example, the stress reduction and sleep promotion system is used to assist athletes (e.g., professional athletes) with recovery. Athletes have a better trained thermoregulation system in comparison to non-athletes. For example, athletes have a faster sweat production and produce a larger amount of sweat. During physical activity, athletes have a CBT of up to 40° C. (104° F.). These differences in the thermoregulation system often cause athletes to suffer from hyperthermia at night, which leads to poor quality sleep. Athletes are also sometimes more sensitive to environmental and physical conditions than non-athletes including, but not limited to, bed temperature, changes in bedding and/or mattresses, ambient temperature, poor room circulation, dehydration, and/or stress from activities earlier in the day. As a result, athletes have difficulty obtaining deep sleep later in the sleeping period (e.g., after the 4th hour of sleep). For an athlete, HRV is naturally high as long as the athlete stays asleep. The mattress pad aids in managing the user's natural metabolism that causes the user's body to heat up quickly and start sweating during deep sleep. By dropping the temperature of the mattress pad, the user is able to obtain more deep sleep.

In one example, a user has a starting amount of deep sleep of less than one hour, a starting HRV equal to 80% of average relative to the user's age, and a starting resting heart rate with a lowest value before waking. The stress reduction and sleep promotion system is programmed with the goals of increasing the amount of deep sleep to 2 hours of total sleep time, improving the HRV to be within an average range for the user's age, and moving the resting heart rate lowest value to the middle of the night to create a hammock-shaped curve. To accomplish these goals, the stress reduction and sleep promotion system decreases the temperature of the mattress pad by 1.1-5.6° C. (2-10° F.). The amount of cooling depends on the starting deep sleep value, the starting HRV, the starting resting heart rate, body mass, and/or thermogenesis history.

The hypothalamus is responsible for maintaining homeostasis, which includes maintaining core body temperature. Temperature influences sleep stages and circadian rhythms through the autonomic nervous system (ANS). HRV is one way to measure how the autonomic nervous system is functioning and the balance between the sympathetic nervous system (SNS) and the parasympathetic nervous system (PNS). At the start of the sleep period, the SNS is dominant. As core body temperature drops, the PNS, which is responsible for recovery and digestion, becomes dominant. When the PNS is dominant, heart rate is reduced. Finally, the SNS becomes dominant again as the individual wakes, resulting in an increased heart rate. This is what produces the hammock-shaped curve in PRIOR ART FIG. 36. If the core body temperature does not drop enough for the PNS to become dominant until closer to wakening, the curve is not a hammock shape.

In one embodiment, sensors provide feedback to the stress reduction and sleep promotion system regarding sleep environment versus core body temperature to determine a number of watts of heat generated during an average sleep session. An average adult generates 60-100 W of heat per average sleep session.

An individual generates power that is measured in watts. Power is calculated by measuring energy per time. An average human generates approximately 100 W in a typical day. The power generated by the individual depends on several factors including, but not limited to, an activity level, a weight, and/or a metabolic rate. Further, an amount of power obtained from a diet is calculated by converting kilocalories into watts. For example, 2500 kcal is equivalent to a power of 121.5 W.

In another embodiment, body temperature is used to track a menstrual cycle of a user. Examples of tracking a menstrual cycle using body temperature are found in U.S. Pat. Nos. 8,834,389 and 9,861,344, each of which is incorporated herein by reference in its entirety.

In yet another embodiment, body temperature is used to determine how a user is responding to a training and/or an exercise program. A decreased body temperature during the training and/or the exercise program indicates that the user needs to decrease an intensity level of the training and/or the exercise program. Recent studies indicate that women should restrict high intensity training during the second half of their menstrual cycle. For further discussion of the effects of menstrual cycle on training, see Julian, Ross et al. "The effects of menstrual cycle phase on physical performance in female soccer players" PloS one vol. 12,3 e0173951. 13 Mar. 2017, doi: 10.1371/journal.pone.0173951, which is incorporated herein by reference in its entirety.

In another embodiment, the stress reduction and sleep promotion system is used to reset a circadian rhythm. In one embodiment, the circadian rhythm reset aids in managing shift work, seasonal circadian disorder, and/or jet lag. To reset a circadian rhythm, a lowest CBT is determined. If an average sleeping period is less or equal to seven hours, the lowest CBT is generally around 2 hours before waking. If an average sleeping period is greater than seven hours, the lowest CBT is generally around 3 hours before waking. For a user traveling east, the circadian rhythm is advanced. To advance the circadian rhythm, a user cools the body (e.g., using a mattress pad) and/or avoids light for three hours before the lowest CBT and warms the body (e.g., using a mattress pad) and/or is exposed to light for three hours after the lowest CBT. For a user traveling west, the circadian rhythm is delayed. To delay the circadian rhythm, a user warms the body (e.g., using a mattress pad) and/or is exposed to light for three hours before the lowest CBT and cools the body (e.g., using a mattress pad) and/or avoids light for three hours after the lowest CBT. In one embodiment, a change of up to 1 hour in either direction (i.e., delay or advance) is used to shift the lowest CBT. In another embodiment, a change of up to 2 hours in either direction (i.e., delay or advance) is used to shift the lowest CBT.

Figure 40:
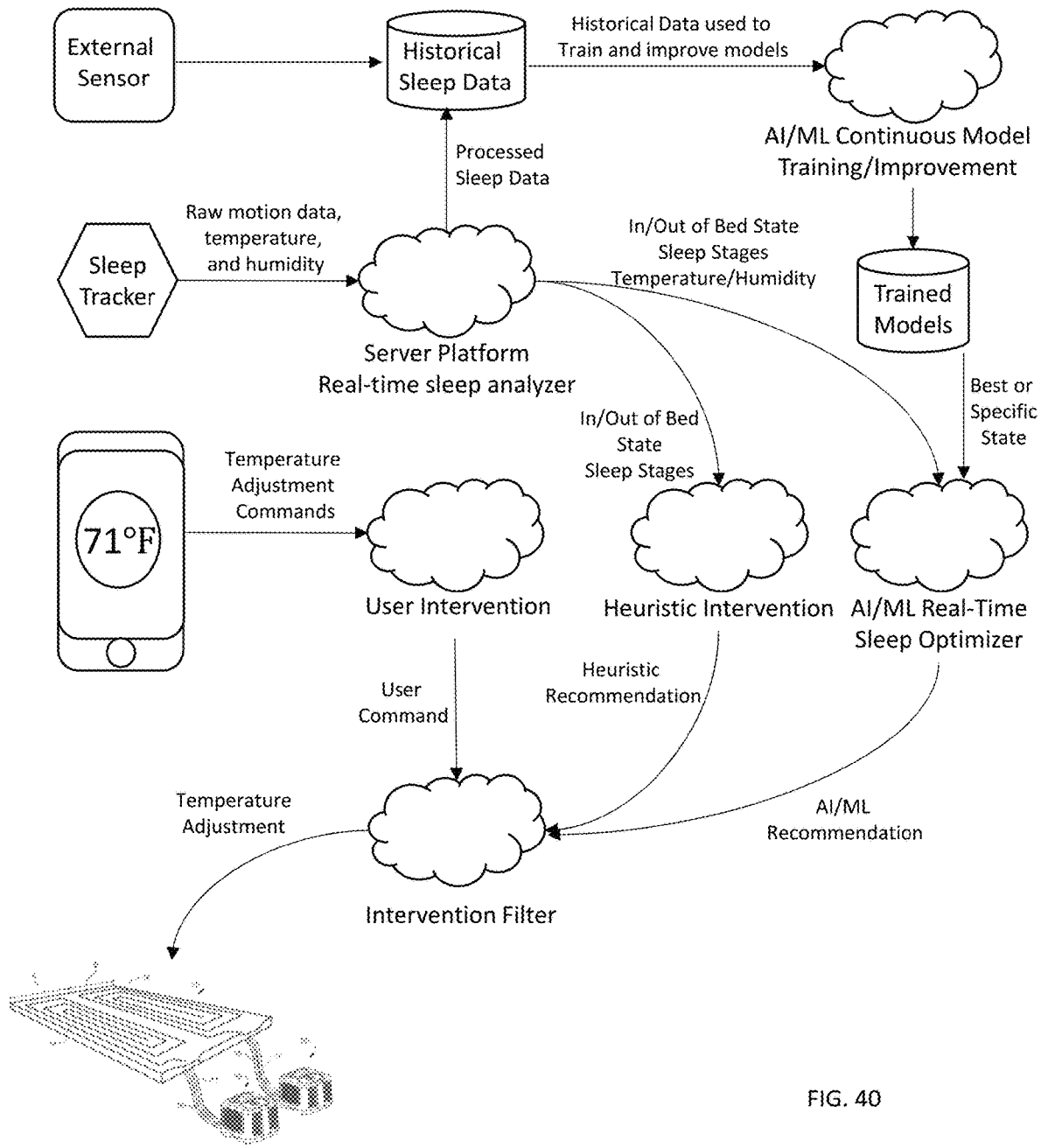
FIG. 40 shows a schematic diagram for adjusting temperature of an article based on user intervention and machine learning algorithms.

FIG. 40 shows a schematic diagram for adjusting temperature of an article based on user intervention and machine learning algorithms. In one embodiment, temperature adjustments (or adjustments to other parameters such as lighting, sound, PEMF, etc.) are made based on user interventions and/or adjustments recommended by at least one artificial intelligence model. By way of example and not of limitation, in one embodiment, a server platform receives raw sensor data from at least one sensor associated with a first user. In one embodiment, the raw sensor data includes heart rate data, heart rate variability data, respiration data, electroencephalogram (EEG) data, blood pressure data, movement data, humidity data, body temperature data, skin temperature data, room temperature data, galvanic skin activity data, and/or analyte data. In one embodiment, the server platform receives the raw sensor data in real time. In one embodiment, the server platform stores historical sleep data for the first user over time in at least one database.

In one embodiment, the server platform aggregates historical sleep data by gathering sleep data from a plurality of sensors, from a plurality of users and feeds the sleep data into an artificial intelligence model. The sleep data is used to train the model to adjust one or more parameters. By way of example and not limitation, in one embodiment, the sleep data is used to train the intervals between adjustments, the timing of adjustments relative to sleep stages of a user, the magnitude of such adjustments (e.g., how many degrees temperature changes) over time, and/or the directionality of adjustments (e.g., turning temperature up or down). In one embodiment, sleep data from a first user is used to first automatically develop a customized sleep schedule for the individual user. The customized sleep schedule includes parameters such as, by way of example and not limitation, a typical length of sleep, a preferred average temperature, a preferred low temperature, a preferred high temperature, relative ease in transitions between different sleep stages, and/or other parameters. By way of example and not limitation, global data from a plurality of users is instead used to fine tune parameters such as the correlation between magnitude of adjustments and transitions between different sleep stages, the relative amount of time between adjustment and transition, and/or other universally knowable or semi-universally knowable parameters. In one embodiment, the server platform includes a plurality of machine learning models. In one embodiment, based on the real-time sensor data and/or user selection, the server platform automatically selects one or more of the models that best fit each individual user.

After selection of a particular machine learning model, the artificial intelligence module receives state data from the server platform (or from the at least one sensor). State data includes real-time information regarding the status of the individual user, such as whether the user is currently in bed or out of bed, what sleep stage the user is in, the temperature of the room, and/or the humidity of the room, among other factors. This state information helps to inform the machine learning model of one or more initial variables needed to seed the machine learning model. In one embodiment, based on the state data, the machine learning model then automatically adjusts a parameter of the article (e.g., temperature, sound, light, PEMF, etc.).

In one embodiment, recommended adjustments from the machine learning model are not used to adjust parameters of the article if a heuristic intervention or a user intervention contradicts the adjustment. Heuristic interventions are automatic adjustments or adjustment preventions based on sensor data received from the at least one sensor. By way of example and not limitation, if a user is detected to no longer be in bed, then a heuristic intervention prevents large changes in temperature or automatically stops regulating the article (e.g., stops thermoregulating the article) after a user has been detected to be out of bed for a predetermined amount of time. A user intervention, on the other hand, is a command received from a user device (e.g., a smartphone, a tablet, a computer, a smart watch, etc.). For example, if the server platform receives a selection to increase temperature by 5 degrees even though the machine learning model recommends a decrease of 1 degree, then the user selection automatically overrides the recommended adjustment. In one embodiment, an intervention filter automatically checks for user commands and/or heuristic recommendations in determining whether to accept or deny machine learning suggestions.

In one embodiment, the server computer automatically determines a chronotype of each user based on the sensor data. A chronotype is often defined as a behavioral variation in a circadian rhythm of an individual. For example, a person might be described as a night owl if they tend to be awake until relatively late hours and also wake up at relatively late hours, while an early bird might go to bed early and wake up early. Chronotypes affect what parameters should be adjusted and how each parameter should be adjusted for each user at different times. Therefore, in one embodiment, the artificial intelligence module takes into account the chronotype of each user when selecting an optimal machine learning model.

Figure 41:
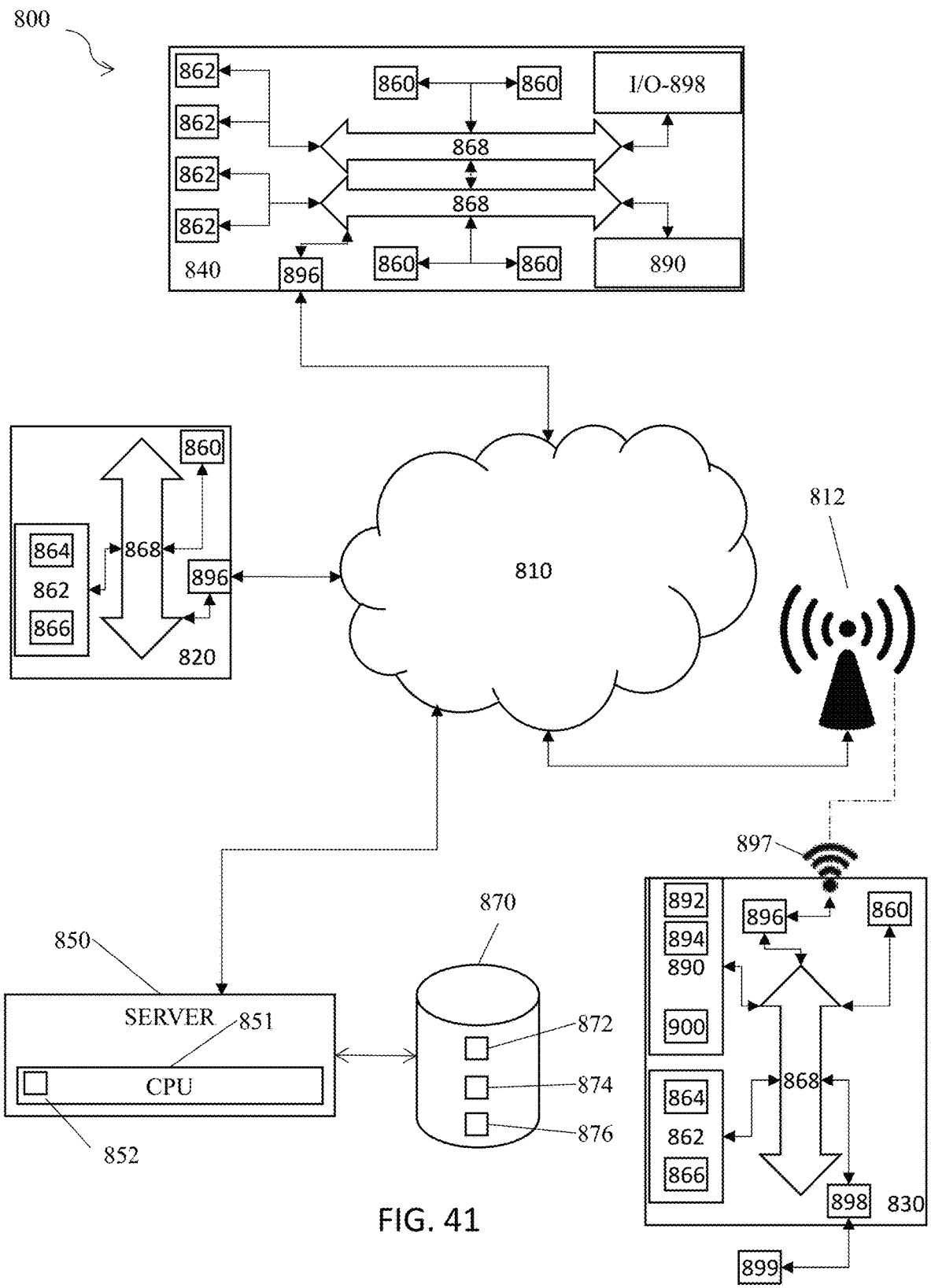
FIG. 41 shows a schematic diagram illustrating general components of a cloud-based computer system.

FIG. 41 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 may house an operating system 872, memory 874, and programs 876.

In one embodiment of the invention, the system 800 includes a cloud-based network 810 for distributed communication via a wireless communication antenna 812 and processing by at least one mobile communication computing device 830. In another embodiment of the invention, the system 800 is a virtualized computing system capable of executing any or all aspects of software and/or application components presented herein on the computing devices 820, 830, 840. In certain aspects, the computer system 800 may be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of digital computers 820, 840, 850 and mobile devices 830, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in this document In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 may additionally include components such as a storage device 890 for storing the operating system 892 and one or more application programs 894, a network interface unit 896, and/or an input/output controller 898. Each of the components may be coupled to each other through at least one bus 868. The input/output controller 898 may receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 may be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 41, multiple processors 860 and/or multiple buses 868 may be used, as appropriate, along with multiple memories 862 of multiple types (e.g., a combination of a DSP and a microprocessor, a plurality of microprocessors, one or more microprocessors in conjunction with a DSP core).

Also, multiple computing devices may be connected, with each device providing portions of the necessary operations (e.g., a server bank, a group of blade servers, or a multiprocessor system). Alternatively, some steps or methods may be performed by circuitry that is specific to a given function.

According to various embodiments, the computer system 800 may operate in a networked environment using logical connections to local and/or remote computing devices 820, 830, 840, 850 through a network 810. A computing device 830 may connect to a network 810 through a network interface unit 896 connected to a bus 868. Computing devices may communicate communication media through wired networks, direct-wired connections or wirelessly, such as acoustic, RF, or infrared, through an antenna 897 in communication with the network antenna 812 and the network interface unit 896, which may include digital signal processing circuitry when necessary. The network interface unit 896 may provide for communications under various modes or protocols.

In one or more exemplary aspects, the instructions may be implemented in hardware, software, firmware, or any combinations thereof. A computer readable medium may provide volatile or non-volatile storage for one or more sets of instructions, such as operating systems, data structures, program modules, applications, or other data embodying any one or more of the methodologies or functions described herein. The computer readable medium may include the memory 862, the processor 860, and/or the storage media 890 and may be a single medium or multiple media (e.g., a centralized or distributed computer system) that store the one or more sets of instructions 900. Non-transitory computer readable media includes all computer readable media, with the sole exception being a transitory, propagating signal per se. The instructions 900 may further be transmitted or received over the network 810 via the network interface unit 896 as communication media, which may include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

It is also contemplated that the computer system 800 may not include all of the components shown in FIG. 41, may include other components that are not explicitly shown in FIG. 41, or may utilize an architecture completely different than that shown in FIG. 41. The various illustrative logical blocks, modules, elements, circuits, and algorithms described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By way of example, the temperature regulating article can be a mattress pad, a sleeping bag, a cushion, or a blanket. The above-mentioned examples are just some of the many configurations that the mentioned components can take on. All modifications and improvements have been deleted herein for the sake of conciseness and readability but are properly within the scope of the present invention.

The invention claimed is:

1. A system for improving sleep, comprising:
a server platform in network communication with at least one regulating device and at least one sensor;
wherein the at least one regulating device is operable to adjust parameters of at least one sleeping article;
wherein the at least one sleeping article includes at least one mattress, at least one mattress pad, and/or at least one blanket;
wherein the server platform receives sensor data from the at least one sensor;
wherein the server platform includes an artificial intelligence module and wherein the artificial intelligence module is operable to recommend an adjustment to parameters of the at least one sleeping article by the at least one regulating device based on the sensor data;
wherein the server platform is operable to automatically transmit commands to the at least one regulating device to execute the recommended adjustments;
wherein the at least one regulating device adjusts parameters of the at least one sleeping article based on the commands from the server platform;
wherein the server platform determines a status of a user based on the sensor data and determines a heuristic-based adjustment for the at least one sleeping article based on the status of the user; and
wherein the heuristic-based adjustment automatically overrides the recommended adjustments by the artificial intelligence module.

2. The system of claim 1, wherein the at least one regulating device includes at least one fluid reservoir including thermoelectric modules for heating and/or cooling fluid, and wherein the at least one regulating device is operable to circulate the fluid into and out of the at least one sleeping article.

3. The system of claim 1, wherein the at least one sensor includes at least one heart rate sensor, at least one respiration sensor, at least one microphone, at least one analyte sensor, at least one pressure sensor, and/or at least one movement sensor.

4. The system of claim 1, wherein the server platform is operable to receive commands to adjust parameters of the at least one sleeping article from at least one user device, and wherein the received commands are operable to override the heuristic-based adjustment.

5. The system of claim 1, wherein the parameters include a temperature of the at least one sleeping article.

6. The system of claim 1, wherein the artificial intelligence module selects a machine learning model for each individual user based on historical sensor data associated with each individual user and real-time sensor data from each individual user.

7. The system of claim 6, wherein the artificial intelligence module automatically determines a chronotype for each individual user and selects the machine learning model for each individual user based on the chronotype of each individual user.

8. The system of claim 6, wherein the historical sensor data includes previous sleep stages for each individual user.

9. The system of claim 1, wherein the magnitude of the recommended adjustments, the timing between the recommended adjustments, and/or the relative timing between the recommended adjustments are based on historical sleep stage information for one or more users.

10. The system of claim 1, wherein the status of the user includes whether the user is currently in bed or out of bed and/or a sleep stage of the user.

11. A system for improving sleep, comprising:
a server platform in network communication with at least one regulating device and at least one sensor;
wherein the at least one regulating device is operable to adjust a temperature of at least one sleeping article;
wherein the server platform receives sensor data from the at least one sensor;
wherein the server platform includes an artificial intelligence module and wherein the artificial intelligence module is operable to recommend an adjustment to the temperature of the at least one sleeping article by the at least one regulating device based on the sensor data;
wherein the artificial intelligence module selects a machine learning model for each individual user based on historical sensor data associated with each individual user and sensor data from each individual user;
wherein the server platform automatically transmits commands to the at least one regulating device to execute the recommended adjustments;
wherein the at least one regulating device adjusts parameters of the at least one sleeping article based on the commands from the server platform;
wherein the server platform determines a heuristic-based adjustment for the at least one sleeping article based on a status of the user; and
wherein the heuristic-based adjustment automatically overrides the recommended adjustments by the artificial intelligence module.

12. The system of claim 11, wherein the at least one sensor includes at least one heart rate sensor, at least one respiration sensor, at least one microphone, at least one analyte sensor, at least one pressure sensor, and/or at least one movement sensor.

13. The system of claim 11, wherein the server platform is operable to receive commands to adjust parameters of the at least one sleeping article from at least one user device.

14. The system of claim 11, wherein the historical sensor data includes previous sleep stages of each individual user.

15. The system of claim 11, wherein the magnitude of the recommended adjustments, the timing between the recommended adjustments, and/or the relative timing between the recommended adjustments are based on historical sleep stage information for one or more users.

16. The system of claim 11, wherein server platform receives the sensor data from the at least one sensor in real time.

17. The system of claim 11, wherein the status of the user includes whether the user is currently in bed or out of bed and/or a sleep stage of the user.

18. A system for improving sleep, comprising:
a server platform in network communication with at least one regulating device and at least one sensor;
wherein the at least one regulating device is operable to adjust a temperature of at least one sleeping article;
wherein the at least one sleeping article includes at least one mattress, at least one mattress pad, and/or at least one blanket;
wherein the server platform receives sensor data from the at least one sensor;
wherein the server platform includes an artificial intelligence module and wherein the artificial intelligence module is operable to recommend an adjustment to the temperature of the at least one sleeping article by the at least one regulating device based on the sensor data;
wherein the server platform automatically transmits commands to the at least one regulating device to execute the recommended adjustments;
wherein the at least one regulating device adjusts parameters of the at least one sleeping article based on the commands from the server platform; and
wherein the magnitude of the recommended adjustments, the timing between the recommended adjustments, and/or the relative timing between the recommended adjustments are based on historical sleep stage information for one or more users.

19. The system of claim 18, wherein the at least one sensor includes at least one heart rate sensor, at least one respiration sensor, at least one microphone, at least one analyte sensor, at least one pressure sensor, and/or at least one movement sensor.

20. The system of claim 18, wherein server platform receives the sensor data from the at least one sensor in real time.

* * * * *